United States Patent
Chhipa et al.

(10) Patent No.: US 8,143,424 B2
(45) Date of Patent: Mar. 27, 2012

(54) THYROID LIKE COMPOUNDS

(75) Inventors: Laxmikant Chhipa, Gujarat (IN); Shitalkumar Pukharaj Zambad, Gujarat (IN); Ramesh Gupta, Gujarat (IN); Davinder Tuli, Gujarat (IN); Ashok Kasundra, Gujarat (IN); Siralee Munshi, Gujarat (IN); M. Amir Siddiqui, Gujarat (IN); Subrat Kumar Bhattamisra, Gujarat (IN); Chaitanya Dutt, Gujarat (IN); Vijay Chauthaiwale, Gujarat (IN)

(73) Assignee: Torrent Pharmaceuticals Ltd., Gujarat State (IN)

(*) Notice: Subject to any disclaimer, the term of this patent is extended or adjusted under 35 U.S.C. 154(b) by 330 days.

(21) Appl. No.: 12/224,168

(22) PCT Filed: Jun. 2, 2008

(86) PCT No.: PCT/IN2008/000345
§ 371 (c)(1),
(2), (4) Date: Aug. 20, 2008

(87) PCT Pub. No.: WO2008/149379
PCT Pub. Date: Dec. 11, 2008

(65) Prior Publication Data
US 2010/0168110 A1    Jul. 1, 2010

(30) Foreign Application Priority Data
Jun. 6, 2007 (IN) .............................. 857/KOL/2007

(51) Int. Cl.
| | |
|---|---|
| A61K 31/5377 | (2006.01) |
| A61K 31/415 | (2006.01) |
| A61K 31/4155 | (2006.01) |
| A61K 31/4245 | (2006.01) |
| A61K 31/506 | (2006.01) |
| C07D 231/20 | (2006.01) |
| C07D 403/06 | (2006.01) |
| C07D 403/04 | (2006.01) |
| C07D 413/04 | (2006.01) |
| A61P 3/04 | (2006.01) |
| A61P 3/06 | (2006.01) |
| A61P 3/10 | (2006.01) |
| A61P 3/00 | (2006.01) |
| A61P 5/14 | (2006.01) |
| A61P 17/00 | (2006.01) |
| A61P 9/00 | (2006.01) |
| A61P 25/24 | (2006.01) |

(52) U.S. Cl. ..................... 548/370.4; 514/404; 514/381; 514/364; 514/269; 514/236.5; 548/144; 548/364.7; 548/253; 544/319; 544/140

(58) Field of Classification Search ........................ None
See application file for complete search history.

(56) References Cited

U.S. PATENT DOCUMENTS

| | | |
|---|---|---|
| 2001/0051645 A1 | 12/2001 | Chiang |
| 2002/0040016 A1 | 4/2002 | Leysen et al. |
| 2002/0049226 A1 | 4/2002 | Chiang et al. |
| 2003/0040535 A1 | 2/2003 | Aspnes et al. |
| 2004/0039028 A1 | 2/2004 | Zhang et al. |
| 2004/0110816 A1 | 6/2004 | Barba et al. |
| 2005/0037925 A1 | 2/2005 | Tsukamoto et al. |
| 2005/0085541 A1 | 4/2005 | Shiohara et al. |

FOREIGN PATENT DOCUMENTS

| | | |
|---|---|---|
| WO | WO 97/16422 | 5/1997 |
| WO | WO 99/43647 | 9/1999 |
| WO | WO 00/02810 | 12/2000 |
| WO | WO 00/72811 | 12/2000 |
| WO | WO 2005/009433 | 2/2005 |
| WO | WO 2006/128056 | 11/2006 |
| WO | WO 2007/003419 | 1/2007 |
| WO | WO 2007/009913 | 1/2007 |
| WO | WO 2007/027842 | 3/2007 |

OTHER PUBLICATIONS

Testa in Biochemical Pharmacology 68, (2004) 2097-2106.*
Burger's Medicinal Chemistry and Drug Discovery (5th Edition, vol. I: Principles and Practice).*
Vippagunta et al., Crystalline solids, Advanced Drug Delivery Reviews, 48 (2001) 3-26.*
Morissette et al. In Advanced Drug Delivery Reviews 56 (2004) 275-300.*
"Obesity and Overweight." World Health Organization Fact Sheet, Sep. 2006.

(Continued)

*Primary Examiner* — Timothy Thomas
*Assistant Examiner* — Dennis Heyer
(74) *Attorney, Agent, or Firm* — Jacobson Holman PLLC

(57) ABSTRACT

A novel thyroid like compounds of formula (I), wherein $R^1$, $R^2$, $R^3$, $R^4$ and Z are as defined in the specification, method for its preparation, composition and use thereof. Further, compounds of formula (I) has significantly low binding affinity to thyroid receptors and thus considerably devoid of thyrotoxic effects. The invention also relates to the use of the compound of formula (I) for the preparation of a medicament for treating various disease conditions including obesity, dyslipidemia, metabolic syndrome and co-morbidities associated with metabolic syndrome.

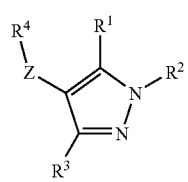

14 Claims, 1 Drawing Sheet

OTHER PUBLICATIONS

Melnikova et al. "Anti-Obesity Therapies." Nature Reviews, Drug Discovery vol. 5, May 2006, pp. 369-370. Ritz. "Total Cardiovascular Risk Management." The American Journal of Cardiology, vol. 100 (3A), Aug. 6, 2007, pp. 53J-60J.

Park et al. "The Metabolic Syndrome." Arch Intern Med. vol. 163, Feb. 24, 2003, pp. 427-436.

Ceska. "Clinical Implications of the Metabolic Syndrome." Diabetes and Vascular Disease Research, vol. 4, Suppl. 3, Sep. 2007, pp. S2-S4.

Kelly. "Peripheral Metabolism of Thyroid Hormones: A Review." Alternative Medicine Review, vol. 4, No. 4, 2000, pp. 306-333.

Burger 6$^{th}$ Edition, vol. 3, pp. S64-S68.

Ye et al. "Thyroid Receptor Ligands.1. Agonist Ligands Selective for the Thyroid Receptor $\beta_1$." Journal of Medicinal Chemistry, vol. 46, No. 9, 2003, pp. 1580-1588.

Abrams et al. "Cholesterol Metabolism in Hypothyroidism and Hyperthyroidism in Man." Journal of Lipid Research, vol. 22, 1981, pp. 323-338.

Aviram et al. "Lipid and Lipoprotein Pattern in Thyroid Dysfunction and the Effect of Therapy." Clin. Biochem. vol. 15, No. 1, Feb. 1982, pp. 62-66. http://www.ncbi.nlm.nih.gov/sites/entrez.

Ness et al. "Effects of L-triiodothyronine and the Thyromimetic L-94901 on Serum Lipoprotein Levels and Hepatic Low-Density Lipoprotein receptor, 3-hydroxy-3-methylglutaryl coenzymes A reductase, and apo A-I gene expression." Biochem Pharmacol. vol. 56, No. 1, Jul. 1, 1998, pp. 121-129. http://www.ncbi.nlm.nih.gov/sites/entrez.

Grover et al. "Effects of the Thyroid Hormone Receptor Agonist GC-1 on Metabolic Rate and Cholesterol in Rats and Primates: Selective Actions Relative to 3,5,3'-Triiodo-L-Thyronine." Endocrinology, vol. 145, No. 4, 2004, pp. 1656-1661.

Grover et al. "Selective Thyroid Hormone Receptor-β activation: A Strategy for Reduction of Weight, Cholesterol, and Lipoprotein (a) with Reduced Cardiovascular Liability." Proc. Natl. Acad Sci. USA, vol. 100, No. 17, Aug. 19, 2003, pp. 10067-10072.

Webb P. "Selective Activators of Thyroid Hormone Receptors." Expert Opinion Investigation Drugs. vol. 13, No. 5, May 2004. pp. 489-500.

Bruin et al. "Lipoprotein and Apolipoprotein B Plasma Concentrations in Hypothroid, Euthyroid, and Hyperthyroid Subjects." Journal of Clinical Endocrinology and Metabolism. vol. 76, No. 1, 1993, pp. 121-126.

Horst et al. "Rapid Stimulation of Hepatic Oxygen Consumption by 3,5-di-iodo-L-thyronine." Biochem. J. vol. 261, 1989, pp. 945-950.

Lombardi et al. "3, 5-Diiodothyronine: Biological Actions and Therapeutic Perspectives." Immuno. Endo. & Metab. Agents in Med Chem. vol. 6, 2006, pp. 255-265.

Columbano et al. "The Thyroid Hormone Receptor-β Agonist GC-1 Induces Cell Proliferation in Rat Liver and Pancreas." Endocrinology. vol. 147, No. 7, 2006, pp. 3211-3218.

Kong et al. "Triiodothyronine Stimulates Food Intake Via the Hypothalamic Ventromedial Nucleus Independent of Changes in Energy Expenditure." Endocrinology vol. 145, No. 11, 2004, pp. 5252-5258.

Horst et al. "3,5-Di-iodo-L-thyronine suppresses TSH in rats in vivo and in rat pituitary fragments in vitro." Journal of Endocrinology. Vo. 145, 1995, pp. 291-297.

Fu et al. "Fibroblast Growth Factor 19 Increase Metabolic Rate and Reverses Dietary and Leptin-Deficient Diabetes." Endocrinology. vol. 145, No. 6, 2004, pp. 2594-2603.

\* cited by examiner

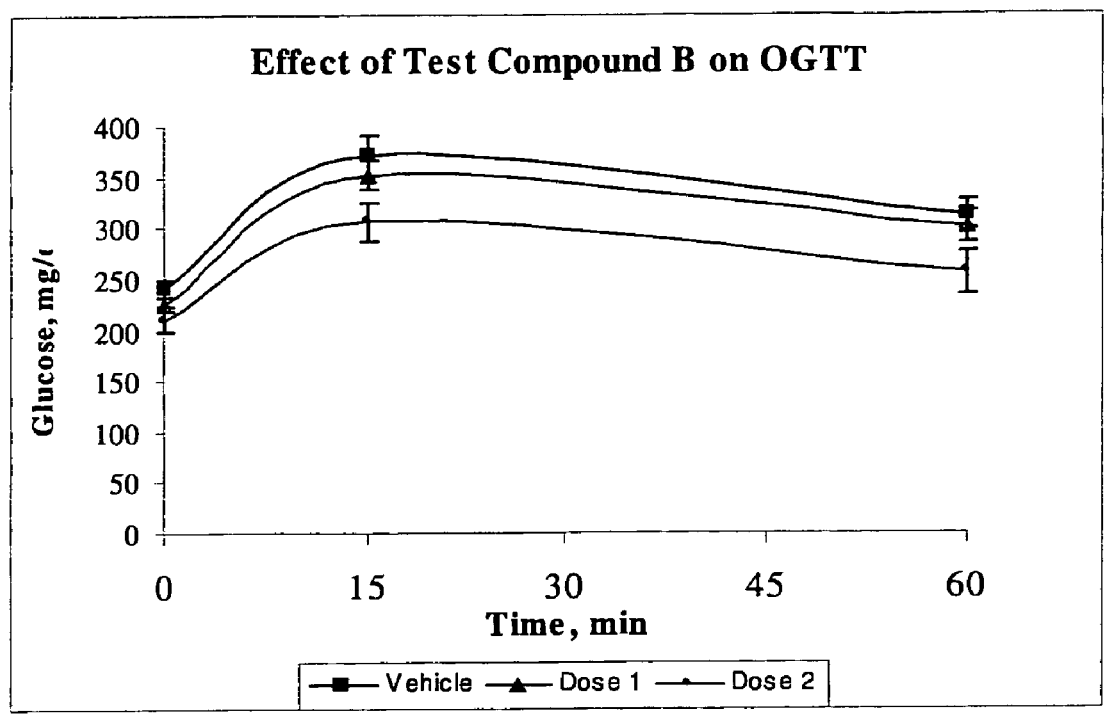

THYROID LIKE COMPOUNDS

This is a national stage of PCT/IN08/000345 filed Jun. 2, 2008 and published in English.

FIELD OF THE INVENTION

The present invention relates to the novel thyroid like compounds of formula (I), wherein $R^1$, $R^2$, $R^3$, $R^4$ and Z are as defined hereinafter, method for its preparation, composition containing such compounds and use of such compounds and composition in therapy. Further, compounds of formula (I) has significantly low binding affinity to thyroid receptors and thus considerably devoid of thyrotoxic effects. The invention also relates to the use of the compound of formula (I) for the preparation of a medicament for treating various disease conditions such as obesity, dyslipidemia, metabolic syndrome and co-morbidities associated with metabolic syndrome.

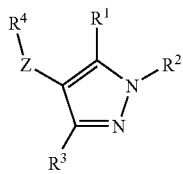

I

BACKGROUND OF THE INVENTION AND PRIOR ART

Obesity is a condition of an excessive accumulation of energy in the body, in which the natural energy reserve, stored in the fatty tissue of humans and other mammals, is increased to a point where it is associated with certain health conditions or increased mortality. Obesity develops from an imbalance between energy expenditure and energy intake, and the physiological approach to obesity treatment is to achieve a negative energy and fat balance. Indeed the weight loss through diet is effective for the majority of patient yet very few manage to maintain their initial weight loss over the long time.

Obesity has reached epidemic proportions globally, with more than 1.6 billion adults overweight—at least 400 million of them clinically obese—and is a major contributor to the global burden of chronic disease and disability (WHO fact sheet, 2006). WHO further projects that by 2015, approximately 2.3 billion adults will be overweight and more than 700 million will be obese. At least 20 million children under the age of 5 years are overweight globally in 2005. Obesity and overweight pose a major risk for serious chronic diseases, including type-II diabetes, cardiovascular disease, hypertension, dyslipidemia, metabolic syndrome, stroke, and certain forms of cancer. The health consequences range from increased risk of premature death, to serious chronic conditions that reduce the overall quality of life.

Although obesity has long been associated with serious health issues, it has only recently been regarded as a disease in the sense of being a specific target for medical therapy. Consequently, developing obesity treatments that target novel pathways is a growing focus for both biopharmaceutical and the medical device industries (Melnikova I. & Wages D Nature Reviews Drug Discovery (2006); 5: 369-370).

The available therapies for treatment of obesity have proved to be of limited value either due to inadequate efficacy or due to higher rate of adverse effects and hence there exists a need for better approach with desired efficacy having low side effects.

Many of the compounds using various new therapeutic approaches such as NPY receptor antagonist, beta3 agonist etc. are in early stage of development. Recently selective thyroid receptor ligands are also being explored for the treatment of obesity.

Epidemological evidences clearly reveal the relationship between the altered carbohydrate and lipid metabolism, accumulation of body fat and cholesterol and subsequent risk of cardiovascular diseases such as atherosclerosis, hypertension etc. Atherosclerosis, a disease of the arteries, is considered to be a leading cause of death worldwide. Epidemiological evidence has clearly established hyperlipidemia as a primary risk factor leading to cardiovascular disease due to atherosclerosis. In recent years, medical fraternity have placed renewed emphasis on lowering plasma cholesterol levels, and more particularly low density lipoprotein cholesterol as an essential step for prevention of cardiovascular diseases. The upper limits of "normal" are now known to be significantly lower than heretofore appreciated. As a result, large segments of populations are now realized to be at particularly high risk. Such independent risk factors include glucose intolerance, left ventricular hypertrophy, hypertension, and being of the male sex. Cardiovascular disease is more prevalent among diabetic subjects, at least in part due to the existence of multiple independent risk factors in this population. Successful treatment of dyslipidemia in the general population, and diabetic subjects in particular, is therefore of utmost clinical importance.

Hypertension is a condition that occurs in the human population as a secondary symptom to various other disorders. However, hypertension is also evidenced in many patients in whom the causative factors are unknown. While such "essential" hypertension is often associated with disorders such as obesity, diabetes and hypertriglyceridemia, the relationship between these disorders has not been well established. Many patients also display the symptoms of high blood pressure in the complete absence of any other signs of disease or disorder. It is known that hypertension can directly lead to various complications such as heart failure, renal failure and stroke (brain hemorrhaging). Hypertension can also contribute to the development of atherosclerosis and coronary disease. Hypertension rarely manifests alone but usually clusters with other cardiovascular risk factors, such as insulin resistance, visceral obesity, and dyslipidemia. These conditions gradually weaken a patient and can lead to death. Though effective blood pressure control is generally regarded as the most important intervention to reduce long-term complications of hypertension the treatment guidelines are now beginning to incorporate the concept of global cardiovascular risk management to improve patient outcomes.

Metabolic syndrome, a cluster of metabolic abnormalities is a combination of insulin resistance, dyslipidemia, obesity and hypertension, which leads to increased morbidity and mortality by cardiovascular diseases (CVD). In the general population, metabolic syndrome increases the risk for CVD by a factor of 1.65. The presence of metabolic syndrome predicted an increased risk for total and cardiovascular mortality (Eberhard Ritz, Am. J Cardiol (2007); 100[Suppl]:53-60). In one of the study it is estimated that metabolic syndrome is present in more than 20% of US adult population. (Young-Woo Park et al. Arch intern Med (2003); 163: 427-436)

In type-II diabetes, obesity and dyslipidemia are also highly prevalent and around 70% of people with type 2 diabetes additionally have hypertension once again leading to increased mortality of cardiovascular diseases.

Metabolic disorders that affect glucose and lipid metabolism such as hyperlipidemia, obesity, diabetes, insulin resistance, hyperglycemia, glucose intolerance, and hypertension have long term health consequences leading to chronic conditions including cardiovascular disease and premature morbidity. Such metabolic and cardiovascular disorders may be interrelated, aggravating or triggering each other and generating feedback mechanisms, which is still unclear.

Hence, multifactorial intervention is crucial in the prevention of type-II diabetes and the reduction of global cardiovascular risk associated with metabolic syndrome. (Richard Ceska, Diabetes and Vascular Disease Research (2007); 4(suppl): S2-S4) Moreover, multifactorial intervention has proved more beneficial than reducing individual risk factor for global cardiovascular risk reduction. Currently, there is no single treatment available which simultaneously addresses multiple components of metabolic syndrome.

Thyroid gland in response to stimulation by TSH, produces T4, T3 and rT3. Although T4, T3 and rT3 are generated within the thyroid gland, T4 is quantitatively the major secondary product. Production of T3 & rT3 within the thyroid is regulated to very small quantities and is not considered significant compared to peripheral production. T4 is either converted to T3 or rT3, or eliminated by conjugation, deamination or decarboxylation. It is estimated that more than 70% of T4 produced in thyroid is eventually deiodinated in peripheral tissues to form T3 or rT3. Although some T3 is produced in the thyroid, approximately 80-85% is generated outside the thyroid, primarily by conversion from T4 in liver and kidney. Further degradation of T3 & rT3 results in the formation of several distinct diiodothyronines: 3,5-T2, 3,3'-T2 and 3,5'-T2 (Kelly G S. Altern Med Rev (2000); 5 (4): 306-333). Structurally all thyroid hormones can be divided into two ring i.e. prime ring and non-prime ring and its SAR suggests unpredictable behaviour of the effect of substituents at (3'-, 5'-, 3- and 5-) on the prime and non-prime ring respectively (Burger' $6^{th}$ edition, vol 3, pp. 564-565). T3 is considered to be the most metabolically active thyroid hormone. Various experimental evidences suggest that major effects of thyroid hormone are mediated by T3. Thyroid hormones affect the metabolism of virtually every cell of the body. At normal levels, these hormones maintain body weight, the metabolic rate, body temperature, and mood, and influence serum low density lipoprotein (LDL) levels. Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety (WO200703419). The brain is also an important target of thyroid hormone, mainly during development but also in adult animals. Severe neonatal hypothyroidism is associated with alterations in cerebellum, especially on granular and Purkinje cells, which exhibit impaired differentiation and migration; Purkinje cells are hypoplastic, and the granular cells fail to migrate from the external germinal layer to the internal granular layer adequately.

Interestingly, it is known that the thyroid hormone known as thyroxine ("T4") converts to thyronine ("T3") in human skin by deiodinase I, a selenoprotein.

Selenium deficiency causes a decrease in T3 levels due to a decrease in deiodinase I activity; this reduction in T3 levels is strongly associated with hair loss. Consistent with this observation, hair growth is a reported side effect of administration of T4. Furthermore, T3 and T4 has been the subject of several patent publications relating to treatment of hair loss, including, for example, International Patent Application Publication No. WO 00/72810, and WO00/72811, The use of thyroid hormones is currently limited as a replacement therapy for patients with hypothyroidism. However, replacement therapy, particularly in older individuals is limited by certain adverse effects of thyroid hormones. Some effects of thyroid hormones may be therapeutically useful in non-thyroid disorders, if adverse effects can be minimized or eliminated. These potentially useful features include weight reduction for the treatment of obesity, cholesterol lowering to treat hyperlipidemia, amelioration of depression and stimulation of bone formation in osteoporosis (Liu Ye et al., JMC (2003); 46: 1580-88) It has been found that hyperthyroidism is associated with low total serum cholesterol, which is attributed to thyroid hormone increasing hepatic LDL receptor expression and stimulating the metabolism of cholesterol to bile acids (Abrams J J et. al. J. Lipid Res. (1981); 22: 323-38). Hypothyroidism, in turn, has been associated with hypercholesterolemia and thyroid hormone replacement therapy is known to lower total cholesterol (Aviram M. et. al. CUn. Biochem. (1982); 15: 62-66; Abrams J J et. al. J. Lipid Res. (1981); 22: 323-38). Thyroid hormone has been shown in animal models to have the beneficial effect of increasing HDL cholesterol and improving the ratio of LDL to HDL by increasing the expression of apo A-I, one of the major apolipoproteins of HDL (Ness G C. et. al. Biochemical Pharmacology, (1998); 56: 121-129; Grover G J. et. al. Endocrinology, (2004); 145: 1656-1661; Grover G J. et. al. Proc. Natl. Acad. Sci. USA, (2003); 100:10067-10072). Through its effects on LDL and HDL cholesterol, it is possible that thyroid hormones may also lower the risk of atherosclerosis and other cardiovascular diseases. Additionally, there is evidence that thyroid hormones lower Lipoprotein (a), an important risk factor which is elevated in patients with atherosclerosis (Paul Webb. Expert Open. Investing. Drugs, (2004); 13 (5): 489-500; de Bruin et. al. J. CUn. Endo. Metal., (1993); 76: 121-126).

Prior attempts to utilize thyroid hormones pharmacologically to treat these disorders have been limited by manifestations of hyperthyroidism and in particular by cardiovascular toxicity (Thyrotoxicosis) (Liu Ye et al., JMC (2003); 46: 1580-88).

Thyroid hormone exerts there effects through thyroid receptors. There are two major subtypes of thyroid receptors located within the nucleus (Genomic effect) TRα and TRβ. TR α1, TR β1 and TR β2 isoforms bind thyroid hormone and acts as a ligand regulated transcription factors. The TR α2 isoform is prevalent in pituitary and other parts of the CNS, does not bind thyroid hormones and acts in many context as a transcriptional repressor. TR α1 is also widely distributed. The literature suggests many or most effects of thyroid hormones on the heart, and in particular heart rate and rhythm are mediated through the TR α1 isoform. On the other hand, most actions of the hormones on the liver and other tissues are mediated more through the β forms of receptors (Liu Ye et al., JMC (2003); 46: 1580-88).

Thyroid hormone has been demonstrated to modulate the behavior of many metabolic pathways potentially relevant for the basal metabolic rate. In general terms, the major candidate mechanisms include uncoupling of cellular metabolism from adenosine triphosphate (ATP) synthesis, or changes in the efficiency of metabolic processes downstream from the mitochondria. Therefore efforts have been made to synthesize thyroid hormone beta selective and/or tissue selective compounds for the treatment of metabolic disorders, which are devoid of thyrotoxic sick effects mediated by TR α receptors.

Thus in effort to make specific TR β selective Thyroid ligands many researchers have tried to synthesize Thyroid mimetics wherein the effect of various prime and non-prime rings and the substituents on it are studied as disclosed in US20050085541, US20040039028, WO2007003419, WO2006128056, WO200709913, US20010051645, US20020049226 and US20030040535 all of which are incorporated herein as reference.

Until recently, T3 was found to be more biologically active than T4 and is presently thought to be the predominant activator of the thyroid hormone receptors (Burger' 6$^{th}$ edition, vol 3, pp. 564-565). In the last decade or so, evidence has accumulated that naturally occurring iodothyronines other than T3 exerts biological effects. Among these, 3,5-diiodothyronine appears to be responsible for rapid, short-term effects on cellular oxidative capacity and respiration rate by direct interaction with mitochondrial binding sites. The accumulated evidence permits the conclusion that the action of T2 do not simply mimic those of T3 but instead are specific action exerted through mechanism that are independent of those actuated by T3 through thyroid hormone receptors (A. Lombardi. Immun Endoc and Metal Agents in Med Chem (2006); 6: 255-65; WO200509433).

Growing body of evidences now suggest that, 3,5-diiodothyronine can induce metabolic inefficiency, possibly by stimulating energy loss via mechanism involving the mitochondrial apparatus rather that nuclear receptors. Such an action of T2 can potentially result in a reduced adiposity and less body weight gain without inducing a clinical syndrome related to thyrotoxic state, by increasing fatty acid influx in to mitochondria and fatty acid oxidation (A. Lombardi. Immun Endoc and Metal Agents in Med Chem (2006); 6: 255-65; Horst C., Biochem J. (1989); 261: 945-950). From a clinical point of view a scenario involving high level of fatty acid oxidation, reduced fat storage, reduction in serum triglyceride and cholesterol levels, reduced lever steatosis, reduced body weight gain without a reduction in calorie/fat intake is an attractive prospect for an intractable obesity (A. Lombardi. Immun Endoc and Metal Agents in Med Chem (2006); 6: 255-65).

WO2005/009433 discloses the composition of 3,5 T2 in therapeutically effective doses mainly for use in obesity, hepatic steatosis and dyslipidemia.

In summary, Thyroid hormones and other idothyronine together or individually influence the metabolism of virtually every cell of the body. These hormones has important physiological role such as to maintain body weight, the metabolic rate, body temperature, and mood, and influence serum low density lipoprotein (LDL) levels etc. Thus, thyroid hormones (T4, T3) can cause weight reduction via increased metabolic rate and a LDL cholesterol reduction through both an upregulation of LDL receptors and increased cholesterol metabolism. However thyroid hormone do not have sufficiently broad therapeutic window, particularly with regard to cardiac acceleration, to be useful for treatment of disorders such as obesity and lipid disorders. Very recently it has been reported that TR selective agonists might be exploited as a therapeutically effective means to lower weight and plasma cholesterol without eliciting deleterious cardiac effects. However, recently it has also been found that the TRβ selective agonist induce proliferative response like lead to hepatocyte proliferation and also induced pancreatic acinar cell proliferation (Amedeo columbano. Endocrinology (2006); 147 (7): 3211-8). There are also reports that T3 increases food consumption at low dosage in animal, independent to its nuclear effects (Wing May Kong et al. Endocrinology (2004); 145: 5252-5258) and the increase in energy intake were also displayed by T2, (Horst et al., J Endocrinology (1995); 145: 291-297) which can be compensatory in the treatment of obesity.

Thus, there exists a need for novel thyroid like compounds, which are useful for the treatment of metabolic disorders such as obesity, insulin resistance, diabetes, dyslipidemia, fatty liver, metabolic syndrome, and disorders of altered thyroid function without having undesirable effects such as thyrotoxicosis and increase in food consumption.

Accordingly, inventors of the present invention have found novel thyroid like compounds which are expected to demonstrate a utility for the treatment or prevention of diseases or disorders associated with inappropriate thyroid hormone activity, for example: 1) The condition associated with a disease or disorder associated with excessive fat accumulation, altered mitochondrial function 2) obesity 3) lipid disorders caused by an imbalance of blood or tissue lipid levels such as dyslipidemia, atherosclerosis 4) impaired glucose tolerance 5) type II diabetes 6) replacement therapy 7) depression 8) cardiovascular diseases and 9) skin disorders and significantly devoid of undesirable effects like thyrotoxicosis and increase in food consumption.

WO2007027842 relates to an anilinopyrazole compounds useful for the treatment of diabetes and related disorders. US2004110816 discloses certain reverse transcriptase inhibitors of pyrazole derivatives useful for the treatment of HIV and WO9716422 discloses certain chromanyl and thiochromanyl compounds having retinoid like activity.

BRIEF DESCRIPTION OF ACCOMPANYING DRAWING

FIG. 1 gives a graphical representation of effect of test compound B in OGTT (Oral Glucose Tolerance Test)

SUMMARY OF THE INVENTION

One embodiment of the present invention is a compound of formula (I)

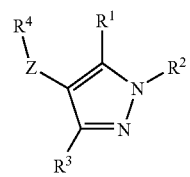

Wherein, $R^1$ and $R^3$ is same or different, and is independently selected from H, $(C_1-C_6)$alkyl, $(C_3-C_7)$ cycloalkyl, halo, CN, $CF_3$, —O—$(C_1-C_6)$alkyl, —$CO_2$—$(C_1-C_6)$alkyl, COOH, —CONH—$(C_1-C_6)$alkyl, —CONH-aryl, —$NH_2$, —CONH—$R^6$, —$CONR^5$, —$C_1$-$C_3$alkyl-aryl, —$(C_1-C_3)$ alkyl-$R^6$, —NH—$(C_1-C_6)$alkyl, —NHaryl, —NH—$SO_2$—$(C_1-C_6)$alkyl, —$CH_2$—NH—$(C_1-C_6)$alkyl, —$CH_2$—O—$(C_1-C_6)$alkyl, —$C_1$-$C_3$alkyl-$NR^5$, $R^6$, $R^7$, wherein $C_1$-$C_6$alkyl and $C_3$-$C_7$ cycloalkyl is optionally substituted with one or more substituents selected from $(C_1-C_6)$alkyl, halo, cyano, —OH, oxo, —COOH, —O—$(C_1-C_6)$alkyl, —O-benzyl, —COO—$(C_1-C_6)$alkyl, —CONH—$(C_1-C_6)$ alkyl, —$CONR^5$, —CONH-aryl, —CONH-heteroaryl or —$CH_2NR^5$;

$R^2$ is selected from $(C_1-C_6)$alkyl, $(C_3-C_6)$cycloalkyl, $(C_3-C_6)$alkenyl, $(C_3-C_6)$ alkynyl, —C(O)—$(C_1-C_3)$alkyl-COOH, —$(C_1-C_3)$alkyl-COOH, —C(O)—$(C_1-C_3)$alkyl-COO-alkyl, —C(O)—C(O)O—$(C_1-C_6)$alkyl, —C(O)—$(C_1-C_3)$alkyl- NH—($C_1$-$C_6$)alkyl, —C(O)—O—($C_1$-$C_6$)alkyl, —C(O) $NR^5$, —C(O)NH—($C_1$-$C_6$)alkyl, —C(O)—($C_1$-$C_3$)alkylaryl, —C(O)—($C_1$-$C_3$)alkyl-$R^6$, $R^6$, $R^7$, wherein said ($C_1$-$C_6$)alkyl, ($C_3$-$C_6$)cycloalkyl, ($C_3$-$C_6$)alkenyl, ($C_3$-$C_6$)alkynyl being optionally substituted with one or more substituents selected from perhaloalkyl, Oxo, —C(O)OH, —C(O)—O—($C_1$-$C_3$)alkyl, —C(O)—O—($C_1$-$C_3$)alky-laryl, —C(O)—O—($C_1$-$C_3$)alkyl-$R^6$, —CONH2, —CONH($C_1$-$C_3$)alkyl, —C(O)NH-aryl, —C(O)NH—$R^6$, —$CONR^5$—CONHNH$_2$, —C(=NH)NH—($C_1$-$C_6$)alkyl, —C(=NH)NH$_2$, C(=NH)NHOH, —C(O)—$R^8$, —C(O)NHSO$_2$($C_1$-$C_6$)alkyl, —C(O)NHSO$_2$-aryl, —C(O)NHOH, —C(O)NHSO$_2$—$R^6$, —C(O)NHNH—($C_1$-$C_6$)alkyl, —C(O)NHNH-aryl, —CONH—($C_1$-$C_2$)alkyl-aryl, —C(O)NH—($C_1$-$C_2$)alkyl-$R^6$, —CH$_2$NR$^5$, —NH$_2$, —NH—($C_1$-$C_6$)alkyl, —NH—C(O)—O—($C_1$-$C_3$)alkyl, —NH—C(O)—($C_1$-$C_3$)alkyl, —NHC(O)-aryl, —NHC(O)—($C_1$-$C_3$)alkylaryl, —NHC(O)—$R^6$, —NH—C(O)NR$^5$, —NH—C(O)NH-aryl, —NHC(O)NH—($C_1$-$C_6$)alkyl, —NHSO$_2$($C_1$-$C_6$)alkyl, —NH—SO$_2$-aryl, —NH—SO$_2$—$R^6$, halo, cyano, —OH, —O—($C_1$-$C_6$)alkyl, —O-aryl, —O-heteroaryl, —O—($C_1$-$C_2$)alkyl-aryl, —SO$_3$H, —SO$_2$NH-aryl, —SO$_2$NH—$R^6$ or —SO$_2$NH—($C_1$-$C_6$)alkyl, $R^6$ or $R^7$;

$R^5$ together with Nitrogen atom to which it is attached form a saturated or unsaturated ($C_3$-$C_6$) membered ring, which may further contain 1-2 heteroatoms selected from O, N or S and which may be optionally substituted with one or more substituents selected from oxo, —COOH, halo, —OH, —O—($C_1$-$C_6$)alkyl, or —($C_1$-$C_6$)alkyl;

$R^6$ is selected from phenyl or 5-8 membered heteroaryl containing 1-4 heteroatoms selected from O, N or S, wherein said heteroaryl or phenyl ring being optionally substituted with one or more substituents selected from halogen, —OH, —O—($C_1$-$C_6$)alkyl, -perhaloalkyl, —($C_1$-$C_6$)alkyl, —($C_3$-$C_6$)cycloalkyl, —SO$_2$($C_1$-$C_6$)alkyl, cyano, —COOH, —C(O)O—($C_1$-$C_6$)alkyl, —C(O)O—CH$_2$-aryl, —C(O)O-aryl, —CONH($C_1$-$C_3$)alkyl, nitro, —NH$_2$, —NH—($C_1$-$C_6$)alkyl, —NHC(O)—($C_1$-$C_6$)alkyl, —NHC(O)-aryl, —NHSO$_2$($C_1$-$C_6$)alkyl, —CONH$_2$, —SO$_2$—($C_1$-$C_6$)alkyl, —NHSO$_2$($C_1$-$C_6$)alkyl or —COR$^8$;

$R^7$ is a 3-6 membered heterocyclic ring containing 1-4 heteroatom selected from O, N or S, and the said heterocyclic ring being optionally substituted with one or more substituents selected from oxo, halogen, —O—($C_1$-$C_6$)alkyl, —OH, —CF$_3$, ($C_1$-$C_6$)alkyl, ($C_3$-$C_6$)cycloalkyl, cyano, —COOH, —C(O)O—($C_1$-$C_6$)alkyl, —C(O)O—CH$_2$-aryl, —C(O)O-aryl, —NH$_2$, —NH—($C_1$-$C_6$)alkyl, —NHC(O)—($C_1$-$C_6$)alkyl, —NHC(O)-aryl, —CONH$_2$, —SO$_2$aryl($C_1$-$C_6$)alkyl, —SO$_2$—($C_1$-$C_6$)alkyl, —NHSO$_2$($C_1$-$C_6$)alkyl or —COR$^8$;

$R^8$ is an amino acid which is linked through its nitrogen atom;

Z=O, CH$_2$ or NH;

$R^4$ is selected from P, Q or T

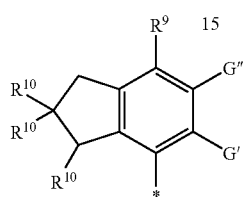

P

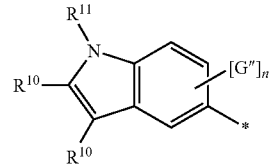

Q

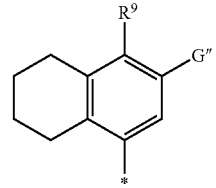

T $R^9$ is selected from —OH, —O-alkyl, —OSO3H, halogen, —C(O)O—($C_1$-$C_6$)alkyl, —C(O)NHR$^8$, —OC(O)—($C_1$-$C_6$)alkyl, —O-perhaloalkyl, —OC(O)O—($C_1$-$C_6$)alkyl, —CONR$^5$, —NHCO—($C_1$-$C_6$)alkyl, —NHC(O)—O—($C_1$-$C_6$)alkyl, —NHC(O)—O-aryl, —NHSO$_2$—($C_1$-$C_6$)alkyl, —NHSO$_2$-aryl, —NHCONR$^5$ or;

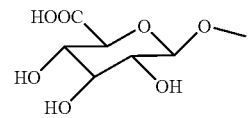

$R^{10}$ is selected from H, Halogen, ($C_1$-$C_6$)alkyl, alkoxy, aryloxy, —NHCO—($C_1$-$C_6$)alkyl, —NHSO2-($C_1$-$C_6$)alkyl or —NH—SO$_2$-aryl;

$R^{11}$ is —CO—($C_1$-$C_6$)alkyl, —SO2-($C_1$-$C_6$)alkyl or —SO$_2$-aryl;

G' is selected from H, halogen or ($C_1$-$C_6$)alkyl;

G" is selected from hydrogen, ($C_1$-$C_6$)alkyl, ($C_3$-$C_6$)cycloalkyl, aryl, halogen, perhaloalkyl, CN, CHO, —($C_1$-$C_3$)alkylaryl, —($C_1$-$C_6$)alkyl-O—($C_1$-$C_6$)alkyl, —CH$_2$R$^9$, —CH$_2$aryl, —CH$_2$NR$^5$, —COOH, —C(O)O($C_1$-$C_6$)alkyl, —CONH—($C_1$-$C_6$)alkyl, —CONR$^5$, —SO$_2$NR$^5$, —SO$_2$NH—($C_1$-$C_6$)alkyl, —SO$_2$NH-aryl; n may be one or two; including their pharmaceutically acceptable salts and their hydrates, solvates, atropisomers, regioisomers, enantiomers, diastereomers, tautomers, polymorphs and prodrugs thereof with a proviso that;

when $R^4$ is Q then $R^2$ is other than $R^6$ and $R^7$;

In another embodiment, the present invention pertains to a compound as above, however only including pharmaceutically acceptable salts thereof.

In another embodiment, the present invention includes use of compound of formula (IA) for treating disease condition associated with inappropriate thyroid hormone activity selected from obesity, insulin resistance, dyslipidemia, metabolic syndrome, type II diabetes, replacement therapy in elderly subjects with hypothyroidism, depression, cardiovascular diseases and skin disorders by administering a therapeutically effective amount of a compound in a living mammalian organism, including human being:

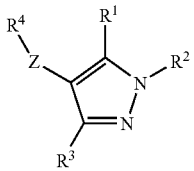

IA

Wherein, $R^1$ and $R^3$ is same or different, and is independently selected from H, $(C_1\text{-}C_6)$alkyl, $(C_3\text{-}C_7)$ cycloalkyl, halo, CN, $CF_3$, —O—$(C_1\text{-}C_6)$alkyl, —$CO_2$—$(C_1\text{-}C_6)$alkyl, COOH, —CONH—$(C_1\text{-}C_6)$alkyl, —CONN-aryl, —NH2, —CONH—$R^6$, —$CONR^5$, —$C_1\text{-}C_3$alkyl-aryl, —$(C_1\text{-}C_3)$ alkyl-$R^6$, —NH—$(C_1\text{-}C_6)$alkyl, —NHaryl, —NH—$SO_2$—$(C_1\text{-}C_6)$alkyl, —$CH_2$—NH—$(C_1\text{-}C_6)$alkyl, —$CH_2$—O—$(C_1\text{-}C_6)$alkyl, —$C_1\text{-}C_3$alkyl-$NR^5$, $R^6$, $R^7$, wherein $C_1\text{-}C_6$alkyl and $C_3\text{-}C_7$ cycloalkyl is optionally substituted with one or more substituents selected from $(C_1\text{-}C_6)$alkyl, halo, cyano, —OH, oxo, —COOH, —O—$(C_1\text{-}C_6)$alkyl, —O-benzyl, —COO—$(C_1\text{-}C_6)$alkyl, —CONH—$(C_1\text{-}C_6)$ alkyl, —$CONR^5$, —CONH-aryl, —CONH-heteroaryl or —$CH_2NR^5$;

$R^2$ is selected from $(C_1\text{-}C_6)$alkyl, $(C_3\text{-}C_6)$cycloalkyl, $(C_3\text{-}C_6)$alkenyl, $(C_3\text{-}C_6)$ alkynyl, —C(O)—$(C_1\text{-}C_3)$alkyl-COOH, —$(C_1\text{-}C_3)$alkyl-COOH, —C(O)—$(C_1\text{-}C_3)$alkyl-COO-alkyl, —C(O)—C(O)O—$(C_1\text{-}C_6)$alkyl, —C(O)—$(C_1\text{-}C_3)$alkyl-NH—$(C_1\text{-}C_6)$alkyl, —C(O)—O—$(C_1\text{-}C_6)$alkyl, —C(O)$NR^5$, —C(O)NH—$(C_1\text{-}C_6)$alkyl, —C(O)—$(C_1\text{-}C_3)$alkylaryl, —C(O)—$(C_1\text{-}C_3)$alkyl-$R^6$, $R^6$, $R^7$, wherein said $(C_1\text{-}C_6)$alkyl, $(C_3\text{-}C_6)$cycloalkyl, $(C_3\text{-}C_6)$alkenyl, $(C_3\text{-}C_6)$alkynyl being optionally substituted with one or more substituents selected from perhaloalkyl, Oxo, —C(O)OH, —C(O)—O—$(C_1\text{-}C_3)$alkyl, —C(O)—O—$(C_1\text{-}C_3)$alky-laryl, —C(O)—O—$(C_1\text{-}C_3)$alkyl-$R^6$, —CONH2, —CONH$(C_1\text{-}C_3)$alkyl, —C(O)NH-aryl, —C(O)NH—$R^6$, —$CONR^5$—$CONHNH_2$, —C(=NH)NH—$(C_1\text{-}C_6)$alkyl, —C(=NH)$NH_2$, C(=NH)NHOH, —C(O)—$R^8$, —C(O)$NHSO_2(C_1\text{-}C_6)$alkyl, —C(O)$NHSO_2$-aryl, —C(O)NHOH, —C(O)$NHSO_2$—$R^6$, —C(O)NHNH—$(C_1\text{-}C_6)$alkyl, —C(O)NHNH-aryl, —CONH—$(C_1\text{-}C_2)$alkyl-aryl, —C(O)NH—$(C_1\text{-}C_2)$alkyl-$R^6$, —$CH_2NR^5$, —$NH_2$, —NH—$(C_1\text{-}C_6)$alkyl, —NH—C(O)—O—$(C_1\text{-}C_3)$alkyl, —NH—C(O)—$(C_1\text{-}C_3)$alkyl, —NHC(O)-aryl, —NHC(O)—$(C_1\text{-}C_3)$alkylaryl, —NHC(O)—$R^6$, —NH—C(O)$NR^5$, —NH—C(O)NH-aryl, —NHC(O)NH—$(C_1\text{-}C_6)$alkyl, —$NHSO_2(C_1\text{-}C_6)$alkyl, —NH—$SO_2$-aryl, —NH—$SO_2$—$R^6$, halo, cyano, —OH, —O—$(C_1\text{-}C_6)$alkyl, —O-aryl, —O-heteroaryl, —O—$(C_1\text{-}C_2)$alkyl-aryl, —$SO_3H$, —$SO_2NH$-aryl, —$SO_2NH$—$R^6$ or —$SO_2NH$—$(C_1\text{-}C_6)$alkyl, $R^6$ or $R^7$;

$R^5$ together with Nitrogen atom to which it is attached form a saturated or unsaturated $(C_3\text{-}C_6)$ membered ring, which may further contain 1-2 heteroatoms selected from O, N or S and which may be optionally substituted with one or more substituents selected from oxo, —COOH, halo, —OH, —O—$(C_1\text{-}C_6)$alkyl, or —$(C_1\text{-}C_6)$alkyl;

$R^6$ is selected from phenyl or 5-8 membered heteroaryl containing 1-4 heteroatoms selected from O, N or S, wherein said heteroaryl or phenyl ring being optionally substituted with one or more substituents selected from halogen, —OH, —O—$(C_1\text{-}C_6)$alkyl, -perhaloalkyl, —$(C_1\text{-}C_6)$alkyl, —$(C_3\text{-}C_6)$cycloalkyl, —$SO_2(C_1\text{-}C_6)$alkyl, cyano, —COOH, —C(O)O—$(C_1\text{-}C_6)$alkyl, —C(O)O—$CH_2$-aryl, —C(O)O-aryl, —CONH$(C_1\text{-}C_3)$alkyl, nitro, —$NH_2$, —NH—$(C_1\text{-}C_6)$alkyl, —NHC(O)—$(C_1\text{-}C_6)$alkyl, —NHC(O)-aryl, —$NHSO_2(C_1\text{-}C_6)$alkyl, —$CONH_2$, —$SO_2$—$(C_1\text{-}C_6)$alkyl, —$NHSO_2(C_1\text{-}C_6)$alkyl or —$COR^8$;

$R^7$ is a 3-6 membered heterocyclic ring containing 1-4 heteroatom selected from O, N or S, and the said heterocyclic ring being optionally substituted with one or more substituents selected from oxo, halogen, —O—$(C_1\text{-}C_6)$alkyl, —OH, —$CF_3$, $(C_1\text{-}C_6)$alkyl, $(C_3\text{-}C_6)$cycloalkyl, cyano, —COOH, —C(O)O—$(C_1\text{-}C_6)$alkyl, —C(O)O—$CH_2$-aryl, —C(O)O-aryl, —$NH_2$, —NH—$(C_1\text{-}C_6)$alkyl, —NHC(O)—$(C_1\text{-}C_6)$alkyl, —NHC(O)-aryl, —$CONH_2$, —$SO_2$aryl$(C_1\text{-}C_6)$alkyl, —$SO_2$—$(C_1\text{-}C_6)$alkyl, —$NHSO_2(C_1\text{-}C_6)$alkyl or —$COR^8$;

$R^8$ is an amino acid which is linked through its nitrogen atom;

Z=O, $CH_2$ or NH;

$R^4$ is selected from P, O or T

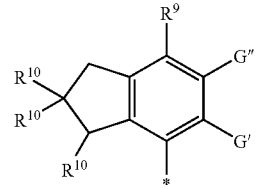

P

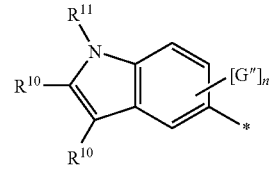

Q

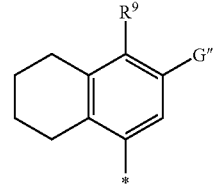

T $R^9$ is selected from —OH, —O-alkyl, —$OSO3H$, halogen, —C(O)O—$(C_1\text{-}C_6)$alkyl, —C(O)$NHR^8$, —OC(O)—$(C_1\text{-}C_6)$alkyl, —O-perhaloalkyl, —OC(O)O—$(C_1\text{-}C_6)$alkyl, —$CONR^5$, —NHCO—$(C_1\text{-}C_6)$alkyl, —NHC(O)—O—$(C_1\text{-}C_6)$alkyl, —NHC(O)—O-aryl, —$NHSO_2$—$(C_1\text{-}C_6)$alkyl, —$NHSO_2$-aryl, —$NHCONR^5$ or;

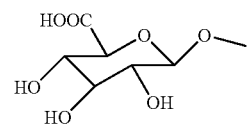

30

$R^{10}$ is selected from H, Halogen, $(C_1\text{-}C_6)$alkyl, alkoxy, aryloxy, —NHCO—$(C_1\text{-}C_6)$alkyl, —NHSO2-$(C_1\text{-}C_6)$alkyl or —NH—$SO_2$-aryl;

$R^{11}$ is H, $(C_1\text{-}C_6)$alkyl, —CO—$(C_1\text{-}C_6)$alkyl, —SO2-$(C_1\text{-}C_6)$alkyl or —$SO_2$-aryl;

G' is selected from H, halogen or $(C_1\text{-}C_6)$alkyl;

G" is selected from hydrogen, $(C_1\text{-}C_6)$alkyl, $(C_3\text{-}C_6)$cycloalkyl, aryl, halogen, perhaloalkyl, CN, CHO, —$(C_1\text{-}C_3)$alkylaryl, —$(C_1\text{-}C_6)$alkyl-O—$(C_1\text{-}C_6)$alkyl, —$CH_2R^9$, —$CH_2$aryl, —$CH_2NR^5$, —COOH, —C(O)O$(C_1\text{-}C_6)$alkyl, —CONH—($C_1$-$C_6$)alkyl, —CONR$^5$, —SO$_2$NR$^5$, —SO$_2$NH—($C_1$-$C_6$)alkyl, —SO$_2$NH-aryl; n may be one or two;

including their pharmaceutically acceptable salts and their hydrates, solvates, atropisomers, regioisomers, enantiomers, diastereomers, tautomers, polymorphs and prodrugs thereof.

In another embodiment, the present invention includes synthetic intermediates that are useful in preparing the compounds of formula (I) and process for preparing such intermediates.

Another embodiment of the present invention is a method for preparation of a compound of formula (I) as herein described in Scheme 1, 2 and 3.

Another embodiment of the present invention is a pharmaceutical composition comprising a compound of formula (I), optionally in admixture with a pharmaceutically acceptable adjuvant, diluent or carrier.

Another embodiment of the present invention is a method for treating obesity by administering a compound of formula (I) to a mammal in need thereof.

Another embodiment of the present invention is a method for ameliorating insulin resistance and/or preventing or delaying progression to frank diabetes by administering a compound of formula (I) to a mammal in need thereof.

Another embodiment of the present invention is a method for preventing and treating dyslipidemia by administering a compound of formula (I) to a mammal in need thereof.

Another embodiment of the present invention is a method for preventing and treating metabolic syndrome by administering a compound of formula (I) to a mammal in need thereof.

Another embodiment of the present invention is the use of a compound of formula (I) for the preparation of a medicament for treating obesity.

Another embodiment of the present invention is the use of a compound of formula (I) for the preparation of a medicament for ameliorating insulin resistance and/or preventing or delaying progression to frank diabetes.

Another embodiment of the present invention is the use of a compound of formula (I) for the preparation of a medicament for preventing and treating dyslipidemia.

Another embodiment of the present invention is the use of a compound of formula (I) for the preparation of a medicament for preventing and treating metabolic syndrome.

In still another embodiment, the present invention provides method of treating disease condition associated with inappropriate thyroid hormone activity without significantly affecting the appetite by administering a therapeutically effective amount of thyroid like compound.

In still another embodiment, the present invention provides method of treating disease condition associated with inappropriate thyroid hormone activity without significantly affecting the appetite by administering the therapeutically effective amount of compound of formula (IA).

DETAIL DESCRIPTION OF THE INVENTION

Definitions

The following definitions apply to the terms as used throughout this specification, unless otherwise limited in specific instances.

The term "Thyroid like compound(s)" as used herein denotes compounds structurally similar to diiodothyronine which are likely to act in a manner similar to that of thyroid hormone but significantly devoid of the toxic effects of Thyroid Hormone.

The term "thyroid receptor ligand" or "thyroid ligand" as used herein covers any chemical substance which can bind to a thyroid receptor. The ligand may act as an antagonist, an agonist, a partial antagonist or a partial agonist.

The term "thyroid receptor" as used herein represents a molecule that receives a thyroid hormone and permits it to dock on the nucleus of a cell and that functions as hormone-activated transcription factor and act by modulating the expression of genes. THRs bind DNA in the absence of hormone, usually suppressing the transcription of genes. Hormone binding involves a conformational change in the receptor that lets it to activate transcription.

The use of the terms "a" and "an" and "the" and similar referents in the context of describing the invention (especially in the context of the following claims) are to be construed to cover both the singular and the plural, unless otherwise indicated herein or clearly contradicted by context.

The term "compound" employed herein refers to any compound encompassed by the generic formula disclosed herein. The compounds described herein may contain one or more double bonds and therefore, may exist as stereoisomers, such as double-bond isomers (i.e., geometric isomers). Accordingly, the chemical structures depicted herein encompass all possible stereoisomers of the illustrated compounds including the stereoisomerically pure form (e.g., geometrically pure) and stereoisomeric mixtures. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to $^2$H, $^3$H, $^{13}$C, $^{14}$C, $^{15}$N, $^{18}$O, $^{17}$O. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention.

The term "regioisomer" is a term known to those skilled in the art and is defined in text books such as *Organic Synthesis*, Smith, M., (McGraw Hill), which defines a regioisomer as "two or more molecules with the same empirical formula, but with a different attachment of the atoms (different connectivity)".

The term "atropisomer" as used herein refers to a stereoisomer where the element of chirality is located on a molecular plane or axis.

Further, it should be understood, when partial structures of the compounds are illustrated, a dash ("-") or "*" indicate the point of attachment of the partial structure to the rest of the molecule. The nomenclature of the compounds of the present invention as indicated herein is according to MDL ISIS® Draw Version 2.2.

"Pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts.

The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COON where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; and combinations comprising one or more of the foregoing salts.

The term "alkyl", used either alone or in attachment with another group refers to a saturated aliphatic hydrocarbon radical having the indicated number of carbon atoms and that is unsubstituted or optionally substituted. When a subscript is used with reference to an alkyl or other group, the subscript refers to the number of carbon atoms that group may contain. For example, a "$C_1$-$C_6$ alkyl" would refer to any alkyl group containing one to six carbons in the structure. Alkyl may be a straight chain or a branched chain.

The term "alkenyl", used either alone or in attachment with another group refers to an unsaturated(=)aliphatic hydrocarbon radical having the indicated number of carbon atoms and that is unsubstituted or optionally substituted.

When a subscript is used with reference to an alkyl or other group, the subscript refers to the number of carbon atoms that group may contain. For example, a "$C_3$-$C_6$ alkenyl" would refer to any alkenyl group containing three to six carbons in the structure. Alkenyl may be a straight chain or a branched chain.

The term "alkynyl", used either alone or in attachment with another group refers to an unsaturated(≡)aliphatic hydrocarbon radical having the indicated number of carbon atoms and that is unsubstituted or optionally substituted. When a subscript is used with reference to an alkyl or other group, the subscript refers to the number of carbon atoms that group may contain. For example, a "$C_3$-$C_6$ alkynyl" would refer to any alkenyl group containing three to six carbons in the structure. Alkynyl may be a straight chain or a branched chain.

The "cycloalkyl" refers to a saturated aliphatic hydrocarbon radical having the indicated number of carbon atoms and that is unsubstituted or optionally substituted. When a subscript is used with reference to an alkyl or other group, the subscript refers to the number of carbon atoms that group may contain. For example, a "$C_3$-$C_6$ cycloalkyl" would refer to any cycloalkyl group containing three to six carbons in the structure.

The term "aryl" refers to an aromatic group for example, which is a 6 to 10 membered monocyclic or bicyclic ring system, which may be unsubstituted or substituted. Representative aryl groups may be phenyl, naphthyl and the like. When said ring is substituted, the substituents are selected from halogen (e.g., F, Cl, Br, I), hydroxy, alkoxy, nitro, carboxylic acid, CF3, NHSO2alkyl, NHCOalkyl, alkyl, alkenyl, alkynyl, cycloalkyl and acyl.

The term "heteroaryl" as used herein, refers to an aromatic group for example, which is a 5 to 10 membered monocyclic or bicyclic ring system, which has at least one heteroatom and at least one carbon atom containing ring. The heteroaryl group may be attached at any available nitrogen or carbon atom of any ring. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, tetrazolyl, triazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxazolyl, benzothienyl, quinolinyl, isoquinolinyl, benzimidazolyl, cinnolinyl, quinoxalinyl, indazolyl, pyrrolopyridyl, furopyridinyl and the like.

The "alkoxy" refers to an alkyl group as defined above attached to the parent molecular moiety through an oxygen bridge. Representative alkoxy radicals include methoxy, ethoxy, n-propoxy, n-butoxy, n-pentyloxy, n-hexyloxy, sec-butoxy, tert-butoxy, tert-pentyloxy, and the like.

As used herein, the term "halo" or "halogen" denotes a fluoro, chloro, bromo, or iodo group.

All substituents ($R^1, R^2 \ldots$) and their further substituents described herein may be attached to the main structure at any heteroatom or carbon atom which results in formation of stable compound.

As used herein, the term "mammal" means a human or an animal such as monkeys, primates, dogs, cats, horses, cows, etc.

As used herein, the term "polymorphs" pertains to compounds having the same chemical formula, the same salt type and having the same form of hydrate/solvate but having different crystallographic properties.

As used herein, the term "hydrates" pertains to a compound having a number of water molecules bonded to the molecule.

As used herein, the term "solvates" pertains to a compound having a number of solvent molecules bonded to the molecule.

The present invention also encompasses prodrugs of compounds of the invention, i.e. second compounds which are converted to the first compounds in vivo.

In vivo cleavable esters are just one type of prodrug of the parent molecule. An in vivo hydrolysable (or cleavable) ester of a compound of the present invention that contains a carboxy group is, for example, a pharmaceutically acceptable ester which is hydrolysed in the human or animal body to produce the parent acid. Suitable pharmaceutically acceptable esters for carboxy include $C_1$-$C_8$ alkoxymethyl esters, for example, methoxymethyl, $C_1$-$C_8$ alkanoloxymethyl ester, for example, pivaloyloxymethyl; phthalidyl esters; $C_3$-$C_8$ cycloalkoxycarbonyloxy-$C_1$-$C_8$ alkyl esters, for example, 1-cyclohexylcarbonyloxyethyl; 1,3-dioxolen-2-onylmethyl esters, for example, 5-methyl-1,3-dioxolen-2-onylmethyl; and $C_1$-$C_8$ alkoxycarbonyloxyethyl esters, for example, 1-methoxycarbonyloxymethyl; and may be formed at any carboxy group in the compounds of the present invention.

In the context of the present specification, the term "treat" or "treatment" also includes "prophylaxis" unless there are specific indications to the contrary. The term "treat" or "treatment" within the context of the present invention further encompasses to administer a therapeutically effective amount of a compound of the present invention, to mitigate either a pre-existing disease state, acute or chronic, or a recurring condition. This definition also encompasses prophylactic therapies for prevention of recurring condition and continued therapy for chronic disorders.

The phrase "a therapeutically effective amount" means the amount of a compound that, when administered to a patient for treating a disease, is sufficient to effect such treatment for the disease. The "therapeutically effective amount" will vary depending on the compound, mode of administration, the disease and its severity and the age, weight, etc., of the patient to be treated.

When used, the expressions "comprise" and "comprising" denote "include" and "including" but not limited to. Thus, other ingredients, carriers and additives may be present.

In one embodiment, the present invention provides a compound of formula (I)

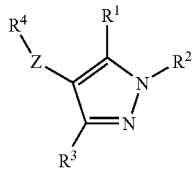

I

Wherein, $R^1$, $R^2$, $R^3$, Z and $R^4$ is as defined above.

The invention also provides pharmaceutically acceptable salts and their hydrates, solvates, atropisomers, regioisomers, enantiomers, diastereomers, tautomers, polymorphs and prodrugs thereof.

One of the preferred embodiment of the present invention is a compound of formula (I) mentioned above, wherein $R^1$, $R^2$, $R^3$ and Z is as defined above and $R^4$ is selected from P or T.

Pharmaceutical Composition

In another embodiment of the invention there is provided a pharmaceutical composition comprising a therapeutically effective amount of one or more of a compound of formula (I). While it is possible to administer therapeutically effective quantity of compounds of formula (I) either individually or in combination, directly without any formulation, it is common practice to administer the compounds in the form of pharmaceutical dosage forms comprising pharmaceutically acceptable excipient(s) and at least one active ingredient. These dosage forms may be administered by a variety of routes including oral, topical, transdermal, subcutaneous, intramuscular, intravenous, intranasal, pulmonary etc.

Oral compositions may be in the form of solid or liquid dosage form. Solid dosage form may comprise pellets, pouches, sachets or discrete units such as tablets, multi-particulate units, capsules (soft & hard gelatin) etc. Liquid dosage forms may be in the form of elixirs, suspensions, emulsions, solutions, syrups etc. Composition intended for oral use may be prepared according to any method known in the art for the manufacture of the composition and such pharmaceutical compositions may contain in addition to active ingredients, excipients such as diluents, disintegrating agents, binders, solubilizers, lubricants, glidants, surfactants, suspending agents, emulsifiers, chelating agents, stabilizers, flavours, sweeteners, colours etc. Some example of suitable excipients include lactose, cellulose and its derivatives such as microcrystalline cellulose, methylcelulose, hydroxy propyl methyl cellulose, ethylcellylose, dicalcium phosphate, mannitol, starch, gelatin, polyvinyl pyrolidone, various gums like acacia, tragacanth, xanthan, alginates & its derivatives, sorbitol, dextrose, xylitol, magnesium Stearate, talc, colloidal silicon dioxide, mineral oil, glyceryl mono Stearate, glyceryl behenate, sodium starch glycolate, Cross Povidone, crosslinked carboxymethylcellulose, various emulsifiers such as polyethylene glycol, sorbitol fattyacid, esters, polyethylene glycol alkylethers, sugar esters, polyoxyethylene polyoxypropyl block copolymers, polyethoxylated fatty acid monoesters, diesters and mixtures thereof.

Sterile compositions for injection can be formulated according to conventional pharmaceutical practice by dissolving or suspending the active substance in a vehicle such as water for injection, N-Methyl-2-Pyrrolidone, propylene glycol and other glycols, alcohols, a naturally occurring vegetable oil like sesame oil, coconut oil, peanut oil, cotton seed oil or a synthetic fatty vehicle like ethyl oleate or the like. Buffers, anti-oxidants, preservatives, complexing agents like cellulose derivatives, peptides, polypeptides and cyclodextrins and the like can be incorporated as required, The dosage form can have a slow, delayed or controlled release of active ingredients in addition to immediate release dosage forms.

The amount of active ingredient which is required to achieve a therapeutic effect will, of course, vary with the particular compound, the route of administration, the subject under treatment, and the particular disorder or disease being treated. The compounds of the invention may be administered orally or parenterally at a dose of from 0.001 to 1500 mg/kg per day, preferably from 0.01 to 1500 mg/kg per day, more preferably from 0.1 to 1500 mg/kg per day, most preferably from 0.1 to 500 mg/kg per day. The dose range for adult humans is generally from 5 mg to 35 g per day and preferably 5 mg to 2 g per day. Tablets or other dosage forms of presentation provided in discrete units may conveniently contain an amount of compound of the invention which is effective at such dosage or as a multiple of the same, for example units containing 5 mg to 500 mg.

Whilst a compound of the invention may be used as the sole active ingredient in a medicament, it is also possible for the compound to be used in combination with one or more further active agents. Such further active agents may be further compounds according to the invention, or they may be different therapeutic agents, for example an anti-obesity or anti-dyslipidemic agent or other pharmaceutically active agent.

The compounds of the present invention may be employed in combination with one or more other suitable therapeutic agents selected from the group consisting of hypolipidemic agents, anti-atherosclerotic agents, anti-diabetic agents, anti-osteoporosis agents, anti-obesity agents, anti-anxiety agents, anti-depressants, anti-hypertensive agents, cardiac glycosides, appetite suppressants, growth promoting agents, agents for the treatment of skin disorders, bone resorption inhibitors and thyroid mimetics.

Examples of suitable hypolipidemic agents for use in combination with the compounds of the present invention include but not limited to an MTP inhibitor, a HMG CoA reductase inhibitor, a squalene synthetase inhibitor, a fibric acid derivative, an ACAT inhibitor, lipoxygenase inhibitors, a cholesterol absorption inhibitor, an ileal Na+/bile acid cotransporter inhibitor, upregulators of LDL receptor, a cholesteryl ester transfer protein (CETP) inhibitor, a bile acid sequestrant, a peroxisome proliferator-activator receptor (PPAR)-alpha agonist, a peroxisome proliferator-activator receptor (PPAR)-delta agonist, a peroxisome proliferator-activator receptor (PPAR)-gamma/delta dual agonist, a peroxisome proliferator-activator receptor (PPAR)-alpha/delta dual agonist and/or a nicotinic acid and its derivative, or a pharmaceutically acceptable salt thereof.

Examples of suitable anti-diabetic agents for use in combination with the compounds of the present invention include but not limited to a biguanide such as metformin, phenformin, a sulfonylurea such as gliclazide, an alpha glucosidase inhibitor, a PPAR γ agonist such as thiazolidinediones, a PPAR α agonist such as fibric acid derivatives, an alpha-amylase inhibitor, a fatty acid oxidation inhibitor, an A2 antagonist, a PPAR δ agonist or antagonist, a PPARα/γ dual agonist, an a P2 inhibitor, and peptidyl peptidase IV (DP4) inhibitor, a SGLT2 inhibitor, a glycogen phosphorylase inhibitor, a glucagon-like peptide-1 (GLP-1) and its analogues, a glucokinase activator, a VPAC2 receptor agonist, a PTP-1B (protein tyrosine phosphatase-1B) inhibitor, an 11β-HSD 1 (11β-hydroxy-steroid dehydrogenase 1) inhibitor, meglitinide, glucocorticoid (GR) antagonist as well as insulin, or a pharmaceutically acceptable salt thereof.

Examples of suitable anti-osteoporosis agents for use in combination with the compounds of the present invention include but not limited to alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors or a pharmaceutically acceptable salt thereof.

Examples of suitable anti-obesity agents for use in combination with the compounds of the present invention include but not limited to a 5HT (serotonin) transporter inhibitor, a NE (norepinephrine) transporter inhibitor, a CB-1 (cannabinoind-1 receptor) antagonist/inverse agonist, a ghrelin antagonist, a H3 (histamine H3) antagonist/inverse agonist, a NPY1 (neuropeptide Y Y1) antagonist, a NPY2 (neuropeptide Y Y2) agonist, a NPY5 (neuropeptide Y Y5) antagonist, a leptin or its derivative, an opioid antagonist, an orexin antagonist, a BRS3 (bombesin receptor subtype 3) agonist, a CCK-A (cholecystokinin-A) agonist, a CNTF (ciliary neurotrophic factor), a CNTF derivative, a GHS (growth hormone secretagogue receptor) agonist, 5HT2c (serotonin receptor 2c) agonist, a Mc3r (melanocortin 3 receptor) agonist, a Mc4r (melanocortin 4 receptor) agonist, a monoamine reuptake inhibitor, a β3 (beta adrenergic receptor 3) agonist, a DGAT1 (diacylglycerol acyltransferase 1) inhibitor, a DGAT2 (diacylglycerol acyltransferase 2) inhibitor, a FAS (fatty acid synthase) inhibitor, a PDE (phosphodiesterase) inhibitor, a thyroid hormone β agonist an UCP-1 (uncoupling protein 1), 2, or 3 activator, a glucocorticoid antagonist, a SCD-1 (stearoyl-CoA desaturase-1) inhibitor, a lipase inhibitor, a fatty acid transporter inhibitor, a dicarboxylate transporter inhibitor, an anorectic agent, such as dexamphetamine, phentermine, phenylpropanolamine or mazindol or a pharmaceutically acceptable salt thereof.

The compounds of the present invention may be combined with growth promoting agents, such as, but not limited to, TRH, diethylstilbesterol, theophylline, enkephalins, E series prostaglandins or a pharmaceutically acceptable salt thereof.

The compounds of the present invention may also be used in combination with growth hormone secretagogues such as GHRP-6, GHRP-1, GHRP-2 or with growth hormone releasing factor and its analogs or growth hormone and its analogs or somatomedins including IGF-1 and IGF-2, or with alpha-adrenergic agonists, such as clonidine or serotinin 5-HT.sub.D agonists, such as sumatriptan, or agents which inhibit somatostatin or its release, such as physostigmine and pyridostigmine. A still further use of the disclosed compounds of the invention is in combination with parathyroid hormone, PTH (1-34) or bisphosphonates, such as MK-217 (alendronate).

Examples of suitable anti-anxiety agents for use in combination with the compounds of the present invention include diazepam, lorazepam, buspirone, oxazepam, and hydroxyzine pamoate and the like.

Examples of suitable anti-depressants for use in combination with the compounds of the present invention include citalopram, fluoxetine, nefazodone, sertraline, paroxetine and the like.

Examples of suitable anti-hypertensive agents for use in combination with the compounds of the present invention include but not limited to an angiotensin converting enzyme (ACE) inhibitor, a renin inhibitor, a beta adrenergic receptor blocker, an alpha adrenergic receptor blocker, a calcium channel blocker, a potassium channel activator, an aldosterone synthase inhibitor, a neutral endopeptidase (NEP) inhibitor, a dual angiotensin converting enzyme/neutral endopeptidase (ACE/NEP) inhibitor, an endothelin receptor antagonist, a dual angiotensin and endothelin receptor antagonist (DARA), a diuretic or a pharmaceutically acceptable salt thereof.

Examples of suitable cardiac glycosides for use in combination with the compounds of the present invention include digitalis and ouabain.

Examples of suitable thyroid mimetics for use in combination with the compounds of the present invention include but not limited to KB-2115, MB07811 or pharmaceutically acceptable salt thereof.

For the treatment of skin disorders or diseases as described above, the compounds of the present invention may be used alone or optionally in combination with a retinoid, such as tretinoin, or a vitamin D analog.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are administered in form of combination with one or more other therapeutic agent(s), it can be administered either concurrently, sequentially or in a fixed unit dosage form.

Abbreviations

TSH—Thyroid-stimulating hormone also known as thyrotropin,
T4—Thyroxine,
T3—Triiodothyronine,
T2—Diiodothyronine,
rT3—Reverse T3,
SAR—Structure activity relationship,
NPY—Neuropeptide Y.

Reaction Schemes for the Synthesis of Compounds of the Invention

In the following, reaction schemes are given for synthesis of the compounds according to another embodiment of the present invention.

SCHEME 1

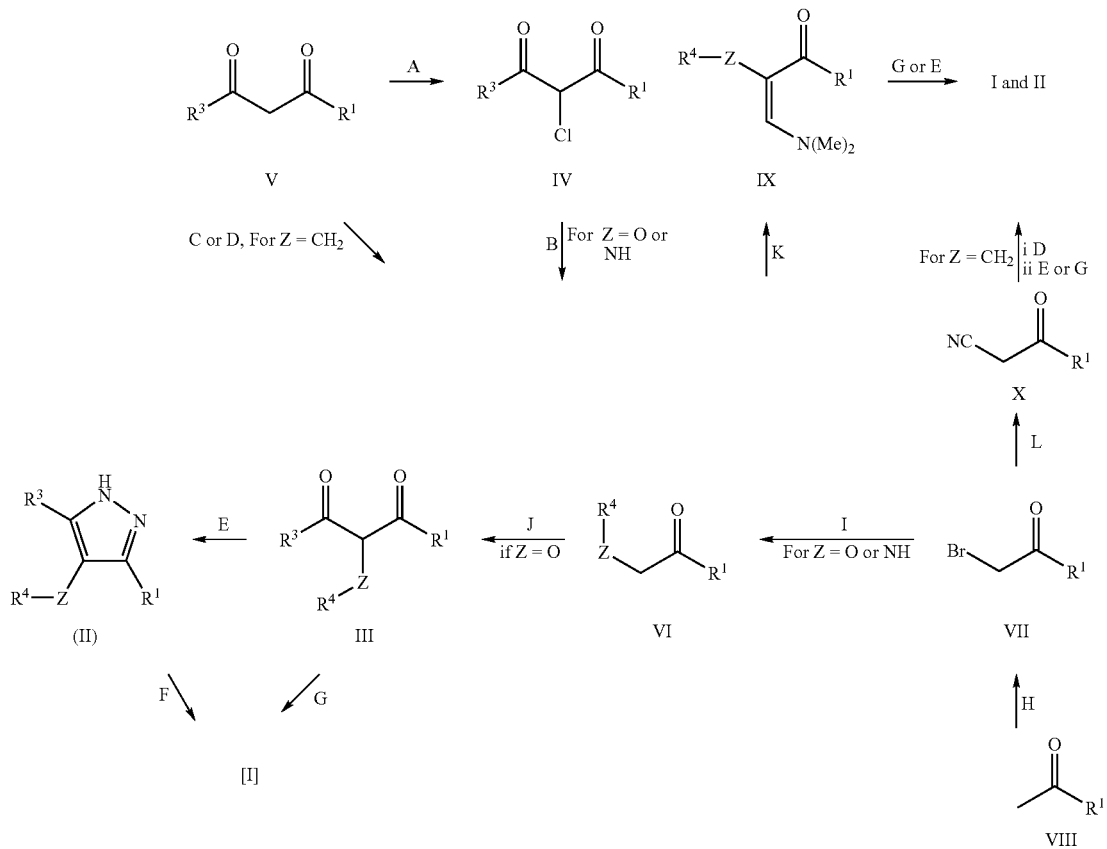

A. (CH₃)₃SiCl, Tetrabutylammonium bromide, DMSO, acetonitrile
B. R⁴OH (XII, XIV, XVI, XVII) or R⁴NH₂,
C. 1 R⁴CHO (XIII), AcOH-piperidine, Toluene
   2 Pd/BaSO₄, H₂, 50 psi
D. R⁴CH₂Y (XV), NaH, THF
E. NH₂NH₂·H₂O, Ethanol
F. R²Y, Base, THF
G. R²NHNH₂, Ethanol, AcOH
H. Bromine, HBr, Methanol or CCl₄,
I. R⁴OH (XII, XIV, XVI, XVII) or R⁴NH₂,
   K₂CO₃, Acetone or DMF
J. R³COOEt or R³COCl, KO ᵗBu, THF
K. DMF-DMA, 80° C.
L. NaCN, DMF Wherein R¹, R², R³, R⁴, and Z are as defined above and Y is halo or any other leaving group.

In a specific embodiment, the compounds of formula (I) is obtained from the pyrazole derivatives of formula (II) or diketo derivatives of formula (III) as shown in scheme-1.

The derivatives of formula (II), is reacted with substituted alkyl halide or any other alkylderivative containing a suitable leaving group in presence of a base selected from metal hydride or metal carbonate, in polar aprotic solvent such as tetrahydrofuran to yield the compounds of formula (I).

Similarly, the diketo derivative of formula (III) on reacting with substituted hydrazine derivatives in alcoholic solvent, yield the compound of formula (I).

The compounds of formula (II) is obtained by treating the compounds of formula (III) as shown in Scheme 1, with hydrazine hydrate under the known condition in the literature. The compound of formula (III) is prepared from the compound of formula (IV) by reacting it with substituted hydroxy indanes of formula (XII), (XIV), (XVI), or (XVII) or with substituted hydroxyl indoles in the presence of base such as metal hydride or metal carbonate in a polar aprotic solvent such as tetrahydrofuran. The compounds of formula (IV) can be obtained from diketo derivative of the formula (V) by dissolving it in an appropriate solvent such as acetonitrile in the presence of a suitable reagent, like trimethylsilyl chloride and dimethylsulphoxide.

Alternately, the compounds of formula (III) is directly obtained by reacting the compounds of formula (V) either with aldehyde derivatives of formula (XIII) in presence of piperidine-acetic acid followed by hydrogenation in presence of catalyst such as Pd/BaSO4 under hydrogen atmosphere or with chloro derivative of formula (XV) in presence of metal hydride or metal carbonate.

In an alternate process, the compound of formula (III) can also be prepared from the compound of formula (VI) by reacting it with appropriate acid chloride or ethyl ester in presence of a base such as metal hydride or metal alkoxide. The compound of formula (VI) is obtained from the compound of formula (VII) by reacting it with suitable hydroxy or amino indane of formula (XII), (XIV), (XVI), or (XVII) or indole derivatives in presence of a base preferably selected from metal hydride or metal carbonate. The compound of formula (VII), as shown in scheme 1 is obtained by bromination of methyl ketone of formula (VIII) in an appropriate solvent such as methanol.

The compounds of formula (II) and the formula (I) can be prepared either from keto derivative of formula (IX) or from cyano derivative of formula (X). By reacting the compounds of formula (IX) with an appropriate substituted or unsubstituted hydrazine in presence of alcoholic solvent to gave compounds of formula (I) and formula (II) respectively. The compound of formula (IX) is obtained by reacting the compound of formula (VI) with dimethylformamide diethyl acetal.

Alternatively, the compounds of formula (X) is reacted with compounds of formula (XV) in presence of a base such as metal hydride, followed by treatment with appropriate substituted or unsubstituted hydrazine in presence of alcoholic solvent to obtain compounds of formula (I) and formula (II) respectively As shown in scheme 1, the cyano derivative of formula (X) is obtained from the compound of formula (VII) by dissolving it in an organic solvent such as dimethyl formamide, in the presence of sodium cyanide. The compound of formula (I) as obtained as per the scheme 1 are either final compounds or else can be converted to formula (I) by appropriate functional group conversion or using conventional methods known in the art.

The intermediates of formula (XII), (XIII), (XIV) and (XV) can be obtained as shown in scheme 2 as depicted herein below.

reacted with paraformaldehyde to obtain the aldehyde substituted compound, which is either reduced to methyl group, in presence of suitable agent such as NH2NH2-KOH-Ethylene glycol or Pd/C under hydrogen atmosphere or to an acid by oxidizing the aldehyde using the mild oxidizing agent such as sulfamic acid and sodium chlorite. The acid group thus, obtained, further reacted with an appropriate alcohol in the presence of mineral acid to obtain ester or using suitable amine and coupling reagent selected from carbodiimide to obtain amide. Further the aldehyde group of formula (XII) is also used to obtain the cyano derivative by using the conventional method. In another alternate process, the halogen substituted hydroxyindane derivatives of formula (XII) is also prepared by reacting 4-hydroxyindane with N-halosuccinimide in presence of catalytic amount of diisopropylamine in solvents preferably tetrahydrofuran or dihaloalkane (G"=halogen) or by treatment of sulfuryl chloride. (G"=chloro).

Compound of formula (XII) or 4-hydroxy indane (G"=H) is treated with hexamine in trifluoroacetic acid, to obtain the compound of formula (XIII).

In still another specific embodiment, compound of formula (XV) can be obtained from the compound of formula (XIII)

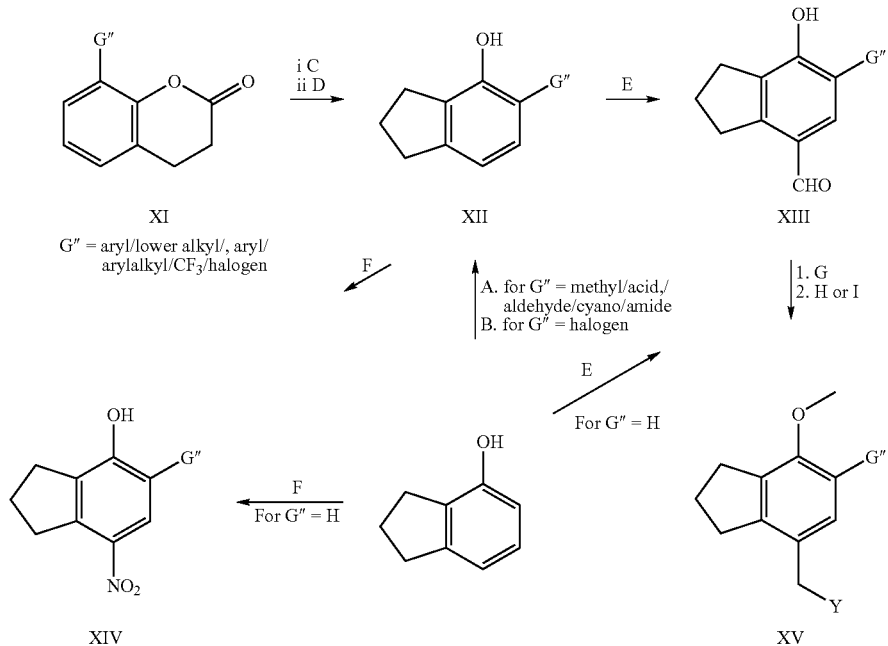

SCHEME 2

XI
G" = aryl/lower alkyl/, aryl/arylalkyl/CF3/halogen

XII

XIII

XIV

XV where G" = Hydrogen/lower alkyl/halogen/CF3/cyano/aldehyde/ester/aryl alkyl; Y = Br/Cl A. 1. Paraformaldehyde, MgCl2, TEA, THF
   2. Pd—C, H2, Methanol
B. N-Halo succinimide, diisopropylamine, THF
C. AlCl3, 170-180° C.
D. Triethylsilane, TFA
E. Hexamine, TFA
F. Nitric acid, AcOH-Water
G. 1. MeI, K2CO3, DMF
   2. NaBH4, Methanol
H. PPh3, CBr4, THF
I. Thionyl Chloride, THF As shown in scheme-2, the intermediates (XII) is obtained from substituted dihydrocoumarin XI or from 4-hydroxyindane. In a specific embodiment, the substituted dihydrocoumarins of formula (XI), is heated with aluminum trichloride, followed by reducing the keto group of indanone with triethylsilane in trifluoroacetic acid to obtain the compound of formula (XII). The reduction of indanone can also be carried out as method disclosed in US2005/0037925, WO9943647 and US2002/0040016. Alternately, 4-hydroxyindane is reacted with methyl iodide in presence of a base followed by reduction in presence of a reducing agent such as sodium borohydride and further reacting the intermediate so obtained with carbon tetrabromide and triphenyl phosphine or thionyl chloride respectively. In an alternate process, the compound of formula (XIV) is also obtained from the compound of formula (XII) or 4-hydroxy indane by treating it with nitric acid in presence of acetic acid.

The intermediates of formula (XVI) and (XVII) can be obtained as shown in scheme 3 as depicted herein below.

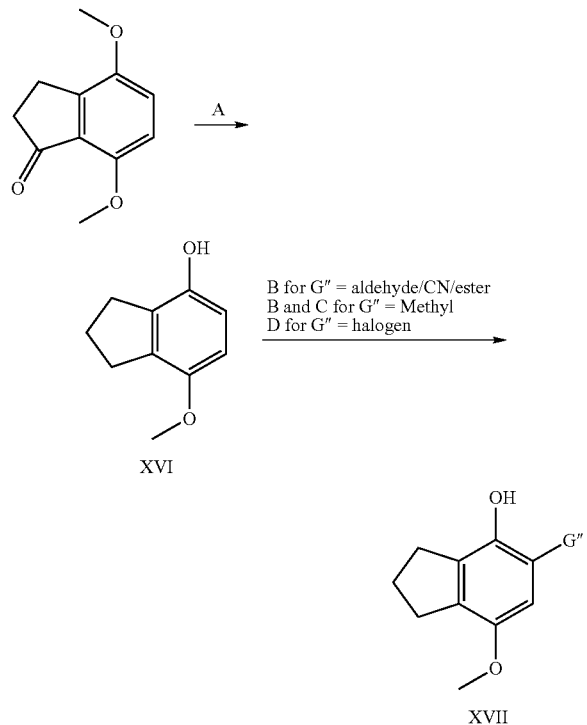

SCHEME-3

XVI

XVII

Where G" = halogen/cyano/aldehyde/ester/amide
A. 1. Triethylsilane, TFA or Pd—C, H$_2$
   2. BBr$_3$, MDC
B. Paraformaldehyde, MgCl$_2$, TEA, THF
C. Pd—C, H$_2$, Methanol
D. N-Halo succinimide, diisopropylamine, THF B for G" = aldehyde/CN/ester
B and C for G" = Methyl
D for G" = halogen The intermediate of formula (XVI) is obtained from the dimethoxy indanone, by reducing the keto group of indanone, using triethylsilane or Pd—C, followed by reacting with boron tribromide.

For the compound of formula (XVII) when G"=methyl is obtained by treating 7-methoxy-indan-4-ol (XVI) with paraformaldehyde and then reducing the intermediate by catalyst reducing agent such as Pd/C, under hydrogen atmosphere, in the presence of a suitable alcoholic solvent selected from methanol. Alternately, for the compound of formula (XVII) when G"=ester or amide, the compounds of formula (XVI) is reacted with paraformaldehyde which on further oxidation under mild condition as described herein above can be converted to G"=acid. Further the acid group can be reacted with an appropriate alcohol in the presence of mineral acid to obtain ester or with using suitable amine and coupling reagent selected from carbodiimide to obtain amide. For G"=cyano in formula (XVII) can be obtained by appropriately selecting cyano substituted indanone or by converting amide derivative to cyano using conventional method.

Alternately, the halo substituted compound of formula (XVII) is obtained by reacting the 7-methoxy-indan-4-ol (XVI) with N-halosuccinimide in presence of catalytic amount of diisopropylamine in solvents selected from tetrahydrofuran or by treatment of sulfuryl chloride (G"=Cl).

PREPARATORY EXAMPLES

The Present Invention is Further Illustrated by the Following Non-Limiting Examples The examples illustrate the preparation of the compounds of formula (I) and as such are not to be considered or construed as limiting the scope of the invention set forth in the claims appended thereto.

Example-1

Compound No. 1

3-[4-(7-Hydroxy-indan-4-yloxy)-3,5-dimethyl-pyrazol-1-yl]-propionic acid

Step I: Preparation of 4,7-Dimethoxy indane

To the cooled and stirred suspension of 4,7-Dimethoxyindan-1-one (35 gm, 0.182 mole) in Triethyl silane (105.7 gm, 0.909 mole), added Trifluoroacetic acid (350 ml) at 10-15° C. The stirring was continued at room temperature for 2 hours and quenched into the water. It was extracted with Ethyl acetate. The Ethyl acetate layer was washed with Sodium bicarbonate solution, dried over Sodium sulphate and evaporated to give crude mass which was purified by column chouromatography using 5% Ethyl acetate in hexane (22.5 gm).
Yield: 69.3%
$^1$H-NMR (400 MHz, CDCl$_3$): δ 6.67 (2H, s), 3.70 (6H, s), 2.74-2.78 (4H, m), 1.95-2.02 (2H, m)

Step-II: Preparation of 7-methoxyindan-4-ol

To the clear solution of 4,7-Dimethoxyindane (22.5 gm, 0.126 mole) in Methylene chloride (400 ml), added Boron tribromide (12.27 ml, 0.13 mole) at 0° C. After 2 hours stirring at 0-10° C., water (100 ml) was added and then the reaction mixture was extracted with Methylene chloride. The Methylene chloride layer was dried over Sodium sulphate and distilled off to give a crude mass which was purified by column chromatography using 7% Ethyl acetate in Hexane (9.0 gm).
Yield: 43.4%
$^1$H-NMR (400 MHz, DMSO-d$_6$):δ 8.66 (1H, s), 6.493-6.558 (2H, m), 3.66 (3H, s), 2.71-2.75 (4H, m), 1.92-2.00 (2H, m)

Step-III: Preparation of 4-(7-Methoxy-indan-4-yloxy)-3,5-dimethyl-1H-pyrazole

To the suspension of 60% Sodium hydride (2.0 gm, 0.051 moles) in Tetrahydrofuran (20 ml) added a solution of 7-Methoxyindan-4-ol (7.0 gm, 0.042 mole) in Tetrahydrofuran (30 ml) at room temperature. After one hour stirring a solution of 3-Chloro 2,4-pentanedione (9.0 ml, 0.075 mole) in Tetrahydrofuran (20 ml) was added followed by addition of Potassium bromide (3.0 gm, 0.025 mole). The reaction mixture was stirred at 70° C. for 6 hours. The water was added and extracted with Diethyl ether. The Ether layer was separated and distilled off to give an oily mass which was partially purified through a column using 2% Ethyl acetate in Hexane to give crude mass (2.7 gm). The obtained crude mass was stirred with Hydrazine hydrate (1 ml) in 20 ml Ethanol at 10° C. Ethanol was evaporated to dryness. The obtained residue was partitioned between water and Ethyl acetate. The separated Ethyl acetate layer was dried over Sodium sulphate and distilled off to give desired product (2.0 gm).

Yield: 18.1% (in two steps)

$^1$H-NMR (400 MHz, DMSO-d$_6$): δ 2.12 (1H, s), 6.61 (1H, d), 6.29 (1H, d), 3.69 (3H, s), 2.88 (2H, t) 2.80 (2H, t), 2.00-2.07 (5H, m), 1.91 (3H, s).

Step-IV: Preparation of 3-[4-(7-Methoxy-indan-4-yloxy)-3,5-dimethyl-pyrazol-1-yl]-propionic acid ethyl ester To the suspension of 60% Sodium hydride (0.372 gm 0.0093 mole) in 10 ml Tetrahydrofuran, added solution of Pyrazole derivative obtained in step-III (2.0 gm, 0.00775 mole) in 10 ml Tetrahydrofuran under nitrogen atmosphere at room temperature After 1 hour stirring at room temperature, a solution of 3-Chloro ethyl propionate (1.15 gm, 0.0084 mole) in 10 ml Tetrahydrofuran was added to the reaction mixture It was stirred at room temperature for 4 hours. The reaction mixture was poured into the water, extracted with ethyl acetate. The Ethyl acetate layer was dried over Sodium sulphate and distilled off. The obtained crude mass was purified by column chromatography using 20% Ethyl acetate in Hexane to give the desired product (0.850 gm).

Yield: 30.6%

$^1$H-NMR (400 MHz, DMSO-d$_6$): δ 6.60 (1H, d), 6.26 (1H, d), 4.15 (2H, t), 4.05 (2H, q), 3.69 (3H, s), 2.88 (2H, t), 2.78-2.83 (4H, m), 1.99-2.08 (5H, m), 1.89 (3H, s), 1.16 (3H, t).

Step-V: Preparation of 3-[4-(7-Hydroxy-indan-4-yloxy)-3,5-dimethyl-pyrazol-1-yl]-propionic acid To the clear solution of Ethyl ester derivative obtained in step-IV (0.85 gm, 0.0023 mole) in 15 ml Methylene chloride, added a solution of Boron tribromide (1.0 ml, 0.0105 mole) in 15 ml Methylene chloride at 0° C. The reaction mixture was stirred for 2 hours at room temperature; 10 ml water was added and extracted with Ethyl acetate. The Ethyl acetate layer was dried over Sodium sulphate and distilled off to give a solid product (230 mg).

Yield: 30.6%

$^1$H-NMR (400 MHz, DMSO-d$_6$):): δ 12.27 (1H, bs), 8.77 (1H, bs), 6.42 (1H, d), 6.15 (1H, d), 4.10 (2H, t), 2.84 (2H, t), 2.71-2.78 (4H, m), 1.98-2.04 (5H, m), 1.88 (3H, s)

Mass: 315 (M$^+$–1)

Example-2

Compound No. 7

3-[4-(7-Hydroxy-indan-4-yloxy)-3-thiophen-2-yl-pyrazol-1-yl]-propionic acid and 3-[4-(7-Hydroxy-indan-4-yloxy)-5-thiophen-2-yl-pyrazol-1-yl]-propionic acid Step-I: Preparation of 2-(7-Methoxy-indan-4-yloxy)-1-thiophen-2-yl-ethanone To the clear solution of 4-Hydroxy-7-methoxy indane (2.0 gm, 0.0121 mole) in Acetone (20 ml), Potassium carbonate (2.52 gm, 0.0182 mole) was added at room temperature and stirred for 1.5 hours. A solution of 2-Bromo-1-thiophene-2-yl-ethanone (3.75 gm, 0.0181 mole) in Acetone (10 ml) was added at 0° C. and stirred for 8 hours at room temperature. The reaction mixture was poured into the water (50 ml) and extracted with Ethyl acetate (2×100 ml). The Ethyl acetate layer was dried over Sodium sulphate and evaporated to give a crude product which was purified by column chromatography using 2% Ethyl acetate in hexane as a mobile phase The collected eluent was evaporated to yield desire product (2.1 gm) as an viscous oil.

Yield: 59.8%

$^1$H-NMR (400 MHz, DMSO-d$_6$): δ 8.12 (1H, dd), 8.09 (1H, dd), 7.29-7.31 (1H, m), 6.63 (2H, s), 5.33 (2H, s), 3.70 (3H, s), 2.87 (2H, t), 2.78 (2H, t), 1.98-2.06 (2H, m).

Step-II: Preparation of 3-Dimethylamino-2-(7-Methoxy-indan-4-yloxy)-1-Thiophen-2-yl-propenone The compound obtained in step-I of example-2 (2.0 gm, 0.0069 mole) was added into 5 ml N,N-dimethylformamide diethylacetal at room temperature and stirred at 90° C. for 2 hours. The reaction mixture was poured into chilled water (100 ml) and extracted with Ethyl acetate. The Ethyl acetate layer was washed with water, dried over Sodium sulphate and evaporated to give an oily product (1.9 gm). It was used for the next step.

Yield: 79.5%

Step-III: Preparation of 4-(7-Methoxy-indan-4-yloxy)-3-thiophen-2-yl-1H-pyrazole and 4-(7-Methoxy-indan-4-yloxy)-5-thiophen-2-yl-1H-pyrazole To the clear solution of the compound obtained in step-II of example 2 (1.9 gm, 0.0055 mole) in Ethanol (30 ml), Hydrazine hydrate (0.5 ml, 0.0102 mole) was added and stirred at 60° C. for 4 hours. Ethanol was evaporated under vacuum and water was added into the reaction mixture. It was extracted with Ethyl acetate (2×50 ml). The Ethyl acetate layer was dried over Sodium sulphate and distilled under vacuum to give a crude product which was purified by column chromatography using Ethyl acetate in Hexane (20:80) as mobile phase. The collected eluent was evaporated under vacuum to yield 1.0 gm of the desired product.

Yield: 58.13%

$^1$H-NMR (400 MHz, DMSO-d$_6$): For major isomer δ 12.82 (1H, s), 7.67 (1H, d), 7.43 (1H, d), 7.24 (1H, d), 7.02-7.08 (1H, m), 6.65 (1H, d), 6.56 (1H, d), 3.70 (3H, s), 2.92 (2H, t), 2.82 (2H, t), 2.03-2.10 (2H, m).

Step-IV: Synthesis of 3-[4-(7-Methoxy-indan-4-yloxy)-3-thiophen-2-yl-pyrazol-1-yl]-propionic acid ethyl ester and 3-[4-(7-Methoxy-indan-4-yloxy)-5-thiophen-2-yl-pyrazol-1-yl]-propionic acid ethyl ester It is prepared using the same method described for step-IV for example-1.

Yield: 45.4%

$^1$H-NMR (400 MHz, DMSO-d$_6$): For major isomer δ 7.64 (1H, s), 7.45 (1H, dd), 7.26 (1H, dd), 703-7.07 (1H, m), 6.67 (1H, d), 6.62 (1H, d), 4.30 (2H, t), 4.01-4.09 (2H, m), 3.72 (3H, s), 2.78-2.90 (6H, m), 2.04-2.07 (2H, m), 1.13 (3H, t).

Step-V: Preparation of 3-[4-(7-Methoxy-indan-4-yloxy)-3-thiophen-2-yl-pyrazol-1-yl]-propionic acid and 3-[4-(7-Methoxy-indan-4-yloxy)-5-thiophen-2-yl-pyrazol-1-yl]-propionic acid To a clear solution of the compound obtained in step-IV (0.6 gm, 0.0014 mole) in Methanol (5.0 ml), A solution of Sodium hydroxide (0.12 gm, 0.0029 mole) in water (25 ml) was added and stirred for 2 hours at room temperature. Methanol was distilled under vacuum completely the residual aqueous layer was washed with Ether (20 ml), acidified with dilute Hydrochloric acid and extracted with Ethyl acetate (2×50 ml). The separated Ethyl acetate layer was dried over sodium sulphate and distilled under vacuum to give acid derivative (440 mg) as a solid.

Yield: 78.7%

$^1$H-NMR (400 MHz, DMSO-$d_6$): for major isomer δ 12.42 (1H, bs), 7.64 (1H, s), 7.44 (1H, d), 7.26 (1H, d), 7.05 (1H, dd), 6.66 (1H, d), 6.62 (1H, d), 4.26 (2H, t), 3.72 (3H, s), 2.78-2.90 (6H, m), 2.01-2.06 (2H, m).

Step-VI: Preparation of 3-[4-(7-Hydroxy-indan-4-yloxy)-3-thiophen-2-yl-pyrazol-1-yl]-propionic acid And 3-[4-(7-Hydroxy-indan-4-yloxy)-5-thiophen-2-yl-pyrazol-1-yl]-propionic acid To a clear solution of compound obtained in step-V of example-2 (0.44 gm, 0.00118 mole) in Methylene chloride (20 ml), a solution of Boron tribromide (0.35 ml, 0.0037 mole) in Methylene chloride (5 ml) was added at 0-10° C. in drop wise manner and stirred for 2 hours at room temperature (25-28° C.). Water (10 ml) was slowly added to reaction mixture and extracted with Methylene chloride (2×30 ml). The separated Methylene chloride layer was dried over Sodium sulphate and distilled under vacuum to give desired product (200 mg) as a solid.

Yield: 47.1%

$^1$H-NMR (400 MHz, DMSO-$d_6$): For major isomer δ 12.41 (1H, s), 9.00 (1H, s), 7.55 (1H, s), 7.44 (1H, d), 7.29 (1H, d), 7.04-7.06 (1H, m), 6.46-6.54 (2H, m), 4.24 (2H, t), 2.73-2.84 (6H, m), 1.96-2.06 (2H, m).

MASS: 369 (M$^+$−1)

Example-3

Compound No. 3

7-[3,5-Dimethyl-1-(1H-tetrazol-5-ylmethyl)-1H-pyrazol-4-yloxy]-indan-4-ol

Step-I: Preparation of [4-(7-Methoxy-indan-4-yloxy)-3,5-dimethyl-pyrazol-1-yl]-acetonitrile It was prepared by using similar method as described for step-IV of example-1 using Bromoacetonitrile instead of Ethyl 3-chloropropionate.

Yield: 96.7%

$^1$H-NMR (400 MHz, DMSO-$d_6$): δ 6.63 (1H, d), 6.31 (1H, d), 5.35 (2H, s), 3.70 (3H, s), 2.89 (2H, t), 2.80 (2H, t), 2.10 (3H, s), 1.98-2.07 (2H, m), 1.93 (3H, s).

Step-II: Preparation of 5-[4-(7-Methoxy-indan-4-yloxy)-3,5-dimethyl-pyrazol-1-ylmethyl]-1H-tetrazole To a stirred solution of [4-(7-Methoxy-indan-4-yloxy)-3,5-dimethyl-pyrazol-1-yl]-acetonitrile (3.0 gm, 0.0101 mole) in Dimethylformamide (30 ml), Sodium azide (1.2 gm, 0.0185 mole) and Triethylamine hydrochloride (4.0 gm, 0.0303 mole) were added at room temperature (27-30° C.). The reaction mixture was stirred at 90-100° C. for 4 hours. The reaction mixture was cooled and poured into dilute Hydrochloric acid (100 ml) and stirred for 30 minutes. The separated solid was filtered and dissolved in Ethyl acetate (100 ml). The Ethyl acetate layer was dried over Sodium sulphate and distilled under vacuum to get a 1.5 gm of desired product as a solid.

Yield: 43.7%

$^1$H-NMR (400 MHz, DMSO-$d_6$): δ 6.62 (1H, d), 6.32 (1H, d), 5.57 (2H, s), 3.70 (3H, s), 2.89 (2H, t), 2.80 (2H, t), 2.11 (3H, s), 2.03-2.09 (2H, m), 1.89 (3H, s).

Step-III: 7-[3,5-Dimethyl-1-(1H-tetrazol-5-ylmethyl)-1H-pyrazol-4-yloxy]-indan-4-ol It was prepared by using similar method as described for step-VI of example-2.

Yield: 31.3%

$^1$H-NMR (400 MHz, DMSO-$d_6$): δ 8.85 (1H, s), 6.44 (1H, d), 6.21 (1H, d), 5.55 (2H, s), 2.84 (2H, t), 2.76 (2H, t), 2.11 (3H, s), 2.00-2.06 (2H, m), 1.88 (3H, s).

Mass: 325 (M$^+$−1)

Example-4

Compound No. 10

5-[4-(7-Hydroxy-indan-4-yloxy)-3,5-dimethyl-pyrazol-1-ylmethyl]-1H-pyrazol-3-ol

Step-I: Preparation of 4-[4-(7-Methoxy-indan-4-yloxy)-3,5-dimethyl-pyrazol-1-yl]-3-oxo-butyric acid ethyl ester.

It was prepared by using similar method as described for step-IV of example-1 using 4-Chloro-3-oxo-butyric acid ethyl ester as an alkylating agent instead of Ethyl 3-chloropropionate.

Yield: 35.7%

$^1$H-NMR (400 MHz, DMSO-$d_6$): δ 6.64 (1H, d), 6.33 (1H, d), 5.11 (2H, s), 4.11 (2H, q), 3.69-3.70 (5H, m), 2.87-2.92 (2H, m), 2.80 (2H, t), 2.02-2.07 (2H, m), 1.92 (3H, s), 1.90 (3H, s), 1.19 (3H, t).

Step-II: Preparation of 5-[4-(7-Methoxy-indan-4-yloxy)-3,5-dimethyl-pyrazol-1-ylmethyl]-1H-pyrazol-3-ol To a stirred solution of keto ester of step-I of example-4 (0.8 gm, 0.00207 mole) in Methanol (20 ml), a solution of Hydrazine hydrate (0.11 ml, 0.00227 mole) in Methanol (5 ml) was added at 0-10° C. The reaction mixture was heated to 75-80° C. and stirred for 12 hours. The Methanol was distilled under vacuum and obtained solid was stirred in Ethyl acetate (5 ml). Further it was filtered, suck dried to give 380 mg of desired product as a solid.

Yield: 51.8%

$^1$H-NMR (400 MHz, DMSO-$d_6$): δ 11.81 (1H, bs), 9.57 (1H, bs), 6.61 (1H, d), 6.28 (1H, d), 5.27 (1H, bs), 5.03 (2H, bs), 3.69 (3H, s), 2.88 (2H, t), 2.80 (2H, t), 2.01-2.08 (5H, m), 1.90 (3H, s).

Step-III: Preparation of 5-[4-(7-Hydroxy-indan-4-yloxy)-3,5-dimethyl-pyrazol-1-ylmethyl]-1H-pyrazol-3-ol It was prepared by using similar method as described for step-VI of example-2.

Yield: 60.4%

$^1$H-NMR (400 MHz, DMSO-$d_6$): δ 8.82 (1H, bs), 6.41 (1H, d), 6.15 (1H, d), 5.22 (1H, s), 5.01 (2H, s), 2.82 (2H, t), 2.74 (2H, t), 1.93-2.06 (5H, m), 1.84 (3H, s).

Mass: 339 (M$^+$−1)

Example-5

Compound No. 19

[3,5-Diethyl-4-(7-hydroxy-6-methyl-indan-4-ylmethyl)-pyrazol-1-yl]-acetic acid

Step-I: Preparation of 7-Chloromethyl-4-methoxy-5-methyl-indan

To a stirred solution of 7-Methoxy-6-methyl-indan-4-carboxaldehyde (39 gm, 0.205 mole) in Methanol (200 ml), Sodium borohydride (9.5 gm, 0.225 mole) was added in portions at 10-20° C. and stirred at room temperature for 2 hours. The reaction mixture was poured into water (200 ml) and acidified with dilute Hydrochloric acid to pH 6. The reaction mixture was subjected to distillation under vacuum and then extracted with Ethyl acetate (2×200 ml). The Ethyl acetate layer was dried over Sodium sulphate and distilled under vacuum to give 38 gm viscous oil. To a clear solution of viscous oil (38.0 gm) in Methylene chloride (160 ml), Thionyl chloride (29.07 ml, 0.396 mole) was added at 10-15° C. and stirred at 20-25° C. for 2 hrs. The reaction mixture was poured into the water (200 ml). The separated organic layer was washed with saturated Sodium bicarbonate, dried over Sodium sulphate, distilled under vacuum to yield crude product as a solid. The crude solid was dissolved in Hexane, filtered and then the filtrate was distilled off to give a desired compound (36.0 gm) as solid.

Yield: 83.5%

$^1$H-NMR (400 MHz, DMSO-$d_6$): δ 6.95 (1H, s), 4.66 (2H, s), 3.70 (3H, s), 2.85-2.98 (4H, m), 2.15 (3H, s), 1.99-2.05 (2H, m).

Step-II: Preparation of 3,5-Diethyl-4-(7-methoxy-6-methyl-indan-4-ylmethyl)-1H-pyrazole To a stirred suspension of 3,5-Heptanedione (8.7 ml, 0.0642 mole) and Potassium carbonate (15.0 gm, 0.1086 mole) in Dimethylformamide (50 ml), the solution of 7-Chloromethyl-4-methoxy-5-methyl-indan (15.0 gm, 0.0714 mole) in Dimethylformamide (25 ml) was added slowly and stirred for 2.5-3 hrs at 40-45° C. To the reaction mixture, water (500 ml) was added then acidified with dilute Hydrochloric acid and extracted with Ethyl acetate (2×500 ml). The Ethyl acetate layer was dried over Sodium sulphate and distilled under vacuum to give 20 gm of diketo derivative as viscous oil. To a clear solution of obtained viscous oil in Isopropyl alcohol (80 ml), a solution of 99% Hydrazine hydrate (3.3 ml, 0.066 mole) in Isopropyl alcohol (20 ml) was added slowly at 15-20° C. The reaction mixture was heated to 80-85° C. and stirred for 1 hour. The Acetic acid (7.5 ml) was added and heating was continued for another 11-12 hrs. The Isopropyl alcohol was distilled and residue was portioned between aqueous Sodium bicarbonate (200 ml) and Ethyl acetate (2×200 ml). The Ethyl acetate layer was dried over Sodium sulphate and distilled under vacuum to give a solid. The obtained solid was stirred in Hexane (50 ml), filtered and dried under vacuum to give 9.3 gm of desired Pyrazole.

Yield: 43.7%

$^1$H-NMR (400 MHz, DMSO-$d_6$): 12.02 (1H, s), 6.46 (1H, s), 3.64 (3H, s), 3.51 (2H, s), 2.84-2.88 (2H, m), 2.75 (2H, t), 2.36-2.40 (4H, m), 2.06 (3H, s), 1.96-2.04 (2H, m), 1.00-1.04 (6H, m).

Step-III: Preparation of [3,5-Diethyl-4-(7-methoxy-6-methyl-indan-4-ylmethyl)-pyrazol-1-yl]-acetic acid ethyl ester To a stirred solution of Pyrazole derivative obtained in step-II of example-5 (9.0 gm, 0.0302 mole) and Ethyl bromo acetate (6.7 ml, 0.0604 mole) in Dimethylformamide (50 ml), Cesium carbonate (14.7 gm, 0.0453 mole) was added and stirred for 16 hour at room temperature (25-30° C.). The reaction mixture was poured into water (400 ml). The separated solid was filtered and washed well with water (50 ml) and suck dried. The solid cake was dissolved in Ethyl acetate (200 ml) and washed with water. The Ethyl acetate layer was dried over Sodium sulphate and distilled under vacuum to get crude solid. The crude solid was stirred in Hexane (50 ml) for 2 hour, filtered, washed with Hexane (10 ml) and dried under vacuum to get desired product as off white solid (9.0 gm)

Yield: 77.6%

$^1$H-NMR (400 MHz, DMSO-$d_6$): δ 6.47 (1H, s), 4.90 (2H, s), 4.12 (2H, q), 3.64 (3H, s), 3.54 (2H, s), 2.85-2.89 (2H, m), 2.73-2.77 (2H, m), 2.44 (2H, q), 2.30 (2H, q), 2.06 (3H, s), 1.96-2.04 (2H, m), 1.19 (3H, t), 1.00 (3H, t), 0.89 (3H, t).

Step-IV: Preparation of [3,5-Diethyl-4-(7-methoxy-6-methyl-indan-4-ylmethyl)-pyrazol-1-yl]-acetic acid To a stirred solution of [3,5-Diethyl-4-(7-methoxy-6-methyl-indan-4-ylmethyl)-pyrazol-1-yl]-acetic acid ethyl ester of step-III (9.0 gm, 0.0234 mole) in Tetrahydrofuran (40 ml) and Methanol (20 ml), a solution of Sodium hydroxide (1.87 gm, 0.0468 mole) in water (75 ml) was added at 20-30° C. and stirred for 1.5-2 hours. The reaction mixture was poured into water (50 ml) and extracted with Ethyl acetate (2×200 ml). The residual aqueous layer was acidified with dilute Hydrochloric acid. The separated solid was filtered, washed well with water (50 ml) and dried under vacuum at 60-65° C. to yield desired product as off white solid. (6.3 gm).

Yield: 75.5%

$^1$H-NMR (400 MHz, DMSO-$d_6$): δ0 12.80-13.00 (1H, bs), 6.48 (1H, s), 4.79 (2H, s), 3.64 (3H, s), 3.54 (2H, s), 2.85-2.89 (2H, m), 2.74-2.78 (2H, m), 2.44 (2H, q), 2.30 (2H, q), 2.06 (3H, s), 1.96-2.04 (2H, m), 1.00 (3H, t), 0.90 (3H, t).

Step-V: preparation of [3,5-Diethyl-4-(7-hydroxy-6-methyl-indan-4-ylmethyl)-pyrazol-1-yl]-acetic acid To a stirred suspension of [3,5-Diethyl-4-(7-methoxy-6-methyl-indan-4-ylmethyl)-pyrazol-1-yl]-acetic acid (6.0 gm, 0.0168 mole) in Methylene chloride (100 ml), a solution of Boron tribromide (4.2 ml, 0.0442 mole) in Methylene chloride (20 ml) was added at 0-5° C. and stirred for 2-3 hrs at 20-30° C. Water (250 ml) was charged into the reaction mixture and stirred for 1 hour. The separated solid was filtered under vacuum, washed with water. The obtained solid was dissolved in Ethyl acetate (2.0 liter) and washed with water (1 liter). Ethyl acetate was distilled under vacuum and further the obtained solid was stirred in Diethyl ether (50 ml), filtered and dried at 55-60° C. under vacuum to yield 4.5 gm of desired product.

Yield: 78.3%

$^1$H-NMR (400 MHz, DMSO-$d_6$): δ 8.14 (1H, s), 6.39 (1H, s), 4.77 (2H, s), 3.48 (2H, merged with peak of water present in DMSO-$d_6$), 2.68-2.77 (4H, m), 2.43 (2H, q), 2.30 (2H, q), 1.94-2.01 (5H, m), 1.00 (3H, t), 0.90 (3H, t).

1H-NMR (400 MHz, CD$_3$OD): δ 6.66 (1H, s), 4.83 (2H, s), 3.59 (2H, s), 2.75-2.83 (4H, m), 2.51 (2H, q), 2.42 (2H, q), 1.91-2.07 (5H, m), 1.05 (3H, t), 0.97 (3H, t).

Mass: 341 (M$^+$−1)

Example-6

Compound No. 33

3-[4-(7-Hydroxy-6-methyl-indan-4-ylmethyl)-3,5-dimethyl-pyrazol-1-yl]-N-isopropyl-propionamide Step-I Preparation of 3-[4-(7-Methoxy-6-methyl-indan-4-ylmethyl)-3,5-dimethyl-pyrazol-1-yl]-propionic acid It was prepared by using similar method as described for step-IV of example-5

Yield: 54.0%

$^1$H-NMR (400 MHz, DMSO-d$_6$): δ 12.29 (1H, bs), 6.49 (1H, s), 4.10 (2H, t), 3.64 (3H, s), 3.48 (2H, s), 2.86 (2H, t), 2.68-2.75 (4H, m), 2.10 (3H, s), 2.08 (3H, s), 1.96-2.03 (2H, m), 1.92 (3H, s).

Step-II: Preparation of N-Isopropyl-3-[4-(7-methoxy-6-methyl-indan-4-ylmethyl)-3,5-dimethyl-pyrazol-1-yl]-propionamide To the solution of 3-[4-(7-Methoxy-6-methyl-indan-4-ylmethyl)-3,5-dimethyl-pyrazol-1-yl]-propionic acid (1.0 gm, 0.00292 mole) in Tetrahydrofuran (20 ml), Carbonyl-diimidazole (0.62 gm, 0.0038 mole) was added at 20-30° C. The reaction mixture was heated and stirred for an hour at 70-75° C. A solution of Isopropyl amine (0.3 ml, 0.00367 mole) in Tetrahydrofuran (5 ml) was added at 20-30° C. The reaction mixture was further stirred at 70° C. for 4 hours. The reaction mixture was cooled and poured into water (50 ml) and extracted with Ethyl acetate (2×100 ml). The Ethyl acetate layer was dried over Sodium sulphate, distilled under vacuum to get a crude product which was stirred in Hexane (20 ml) and filtered to give 810 mg of desired product as a solid.

Yield: 72.8%

$^1$H-NMR (400 MHz, DMSO-d$_6$): δ 7.77 (1H, d), 6.49 (1H, s), 4.10 (2H, t), 3.77 (1H, m), 3.64 (3H, s), 3.47 (2H, s), 2.86 (2H, t), 2.73 (2H, t), 2.49 (2H, merged with DMSO-d6 peak), 2.08 (6H, s), 1.95-2.03 (2H, m), 1.92 (3H, s), 0.98 (6H, d).

Step-III: Preparation of 3-[4-(7-Hydroxy-6-methyl-indan-4-ylmethyl)-3,5-dimethyl-pyrazol-1-yl]-N-isopropyl propionamide It was prepared by using similar method as described for step-VI of example-2

Yield: 51.9%

$^1$H-NMR (400 MHz, DMSO-d$_6$): δ 8.11 (1H, s), 7.76 (1H, d), 6.40 (1H, s), 4.08 (2H, t), 3.76-3.81 (1H, m), 3.42 (2H, s), 2.75 (2H, t), 2.69 (2H, t), 2.51 (2H, merged with DMSO-d6 peak), 2.07 (3H, s), 2.02 (3H, s), 1.90-1.99 (5H, m), 0.98 (6H, d).

Mass: 370 (M$^+$+1)

Example-7

Compound No. 42

5-[3,5-Diethyl-4-(7-hydroxy-6-methyl-indan-4-ylmethyl)-pyrazol-1-ylmethyl]-3H-[1,3,4]oxadiazol-2-one Step-I: Preparation of [3,5-Diethyl-4-(7-methoxy-6-methyl-indan-4-ylmethyl)-pyrazol-1-yl]-acetic acid hydrazide A stirred suspension of [3,5-Diethyl-4-(7-methoxy-6-methyl-indan-4-ylmethyl)-pyrazol-1-yl]-acetic acid ethyl ester (3.3 gm, 0.0085 mole) and 99% Hydrazine hydrate (33 ml) was heated at 60-65° C. for 3 hours. The reaction mixture was poured into water (200 ml), stirred for an hour and then filtered. The obtained solid was stirred in Methanol (10 ml), filtered and dried to give 2.9 gm of desired product as a solid.

Yield: 91.4%

$^1$H-NMR (400 MHz, DMSO-d$_6$): δ 9.23 (1H, s), 6.51 (1H, s), 4.58 (2H, s), 4.29-4.30 (2H, d), 3.64 (3H, s), 3.52 (2H, s), 2.87 (2H, t), 2.76 (2H, t), 2.47 (2H, merged with DMSO-d6 peak), 2.30 (2H, q), 2.07 (3H, s), 1.97-2.04 (2H, m), 1.00 (3H, t), 0.90 (3H, t).

Step-II: Preparation of 5-[3,5-Diethyl-4-(7-methoxy-6-methyl-indan-4-ylmethyl)-pyrazol-1-ylmethyl]-3H-[1,3,4]oxadiazol-2-one To a stirred solution of [3,5-Diethyl-4-(7-methoxy-6-methyl-indan-4-ylmethyl)-pyrazol-1-yl]-acetic acid hydrazide (1.5 gm, 0.0041 mole) in 1,4-Dioxane (70 ml), Carbonyl-diimidazole (2.0 gm, 0.0121 mole) was added at 20-30° C. The reaction mixture was stirred for 8 hours at 90-95° C. The reaction mixture was cooled and poured into water (200 ml), stirred for 2 hours and then separated solid was filtered. Further the solid was stirred in Diethyl ether (25 ml) and filtered, dried to give 900 mg of desired product as a solid.

Yield: 56.2%

$^1$H-NMR (400 MHz, DMSO-d$_6$): δ 12.28 (1H, bs), 6.45 (1H, s), 5.20 (2H, s), 3.64 (3H, s), 3.54 (2H, s), 2.87 (2H, t), 2.74 (2H, t), 2.54 (2H, q), 2.31 (2H, q), 2.06 (3H, s), 1.98-2.01 (2H, m), 1.00 (3H, t), 0.92 (3H, t).

Step-III: Preparation of 5-[3,5-Diethyl-4-(7-hydroxy-6-methyl-indan-4-ylmethyl)-pyrazol-1-ylmethyl]-3H-[1,3,4]oxadiazol-2-one It was prepared by using similar method as described for step-VI of example-2.

Yield: 70.7%

$^1$H-NMR (400 MHz, DMSO-d$_6$): δ 12.41 (1H, s), 8.14 (1H, s), 6.37 (1H, s), 5.20 (2H, s), 3.49 (2H, s), 2.69-2.77 (4H, m), 2.53 (2H, merged with DMSO-d6 peak), 2.31 (2H, q), 1.91-2.01 (5H, m), 0.99 (3H, t), 0.92 (3H, t).

Mass: 383 (M$^+$+1)

Example-8

Compound No. 45

6-[4-(7-Hydroxy-6-methyl-indan-4-ylmethyl)-3,5-dimethyl-pyrazol-1-ylmethyl]-2-methyl-3H-pyrimidin-4-one

Step-I: Preparation of 4-[4-(7-Methoxy-6-methyl-indan-4-ylmethyl)-3,5-dimethyl-pyrazol-1-yl]-3-oxo-butyric acid ethyl ester It was prepared by using similar method as described for step-IV of example-1 using 4-Chloro-3-oxo-butyric acid ethyl ester as an alkylating agent instead of Ethyl 3-chloropropionate.

Yield: 47.1%

$^1$H-NMR (400 MHz, DMSO-$d_6$): 6.53 (1H, s), 5.07 (2H, s), 4.4.08 (2H, q), 3.64 (3H, s), 3.63 (2H, s), 3.51 (2H, s), 2.86 (2H, t), 2.74 (2H, t), 2.09 (3H, s), 1.97-2.05 (5H, m), 1.92 (3H, s), 1.18 (3H, t)

Step-II: Preparation of 6-[4-(7-Methoxy-6-methyl-indan-4-ylmethyl)-3,5-dimethyl-pyrazol-1-ylmethyl]-2-methyl-3H-pyrimidin-4-one To the solution of 4-[4-(7-Methoxy-6-methyl-indan-4-ylmethyl)-3,5-dimethyl-pyrazol-1-yl]-3-oxo-butyric acid ethyl ester (1.0 gm, 0.0025 mole) in Ethanol (60 ml), Acetamidine hydrochloride (0.71 gm, 0.0075 mole) was added. Further to this, Sodium ethoxide (0.51 gm, 0.0075 mole) was added at 5-10° C. and then stirred at 70-75° C. for 2 hours. The Ethanol was distilled under vacuum and residue was partitioned between Ethyl acetate (100 ml) and water (100 ml). Further aqueous layer was extracted with Ethyl acetate (2×100 ml). The combined volume of Ethyl acetate layer was reduced to 20 ml and then filtered to give 800 mg of desired product.

Yield: 81.3%

$^1$H-NMR (400 MHz, DMSO-$d_6$): δ 12.42 (1H, bs), 6.50 (1H, s), 5.16 (1H, s), 4.97 (2H, s), 3.64 (3H, s), 3.55 (2H, s), 2.87 (2H, t), 2.74 (2H, t), 2.27 (3H, s), 2.09 (3H, s), 2.05 (3H, s), 1.98-2.02 (2H, m), 1.95 (3H, s).

Step-III: Preparation of 6-[4-(7-Hydroxy-6-methyl-indan-4-ylmethyl)-3,5-dimethyl-pyrazol-1-ylmethyl]-2-methyl-3H-pyrimidin-4-one It was prepared by using similar method as described for step-VI of example-2

Yield: 58.4%

$^1$H-NMR (400 MHz, DMSO-$d_6$): δ 12.41 (1H, s), 8.12 (1H, s), 6.42 (1H, s), 5.13 (1H, s), 4.95 (2H, s), 3.49 (2H, s), 2.67-2.77 (4H, m), 2.26 (3H, s), 2.03 (6H, s), 1.94-1.99 (5H, m).

Mass: 379 (M$^+$+1)

Example-9

Compound No. 46

3-[4-(7-Hydroxy-6-methyl-indan-4-ylmethyl)-3,5-dimethyl-pyrazol-1-ylmethyl]-[1,2,4]oxadiazol-5-ol

Step-I: Preparation of [4-(7-Methoxy-6-methyl-indan-4-ylmethyl)-3,5-dimethyl-pyrazol-1-yl]-acetonitrile It was prepared by using similar method as described for step-IV of example-1 using Bromoacetonitrile as an N-alkylating agent instead of Ethyl 3-chloropropionate.

Yield: 52.8%

$^1$H-NMR (400 MHz, DMSO-$d_6$): δ 6.51 (1H, s), 5.31 (2H, s), 3.64 (3H, s), 3.52 (2H, s), 2.87 (2H, t), 2.73 (2H, t), 2.15 (3H, s), 2.09 (3H, s), 1.92-2.03 (5H, m).

Step-II: Preparation of N-Hydroxy-2-[4-(7-methoxy-6-methyl-indan-4-ylmethyl)-3,5-dimethyl-pyrazol-1-yl]acetamidine To a stirred solution of [4-(7-Methoxy-6-methyl-indan-4-ylmethyl)-3,5-dimethyl-pyrazol-yl]-acetonitrile (2.0 gm 0.00647 mole) in methanol (50 ml), A suspension of Hydroxylamine hydrochloride (2.29 gm, 0.033 mole) and Potassium carbonate (4.37 gm, 0.0317 mole) in water (20 ml) was added. The reaction mixture was stirred for 30-36 hours at 70° C., cooled and then was filtered. The obtained solid was washed with water (10 ml) and finally with Hexane and dried under vacuum to give 1.8 gm of desired product Yield: 81.4%

$^1$H-NMR (400 MHz, DMSO-$d_6$): δ 9.20 (1H, bs), 6.52 (1H, s), 5.24 (2H, s), 4.51 (2H, s), 3.64 (3H, s), 3.49 (2H, s), 2.86 (2H, t), 2.74 (2H, t), 2.09 (6H, s), 1.98-2.05 (2H, m), 1.94 (3H, s).

Step-III: Preparation of 3-[4-(7-Methoxy-6-methyl-indan-4-ylmethyl)-3,5-dimethyl-pyrazol-1-ylmethyl]-[1,2,4]oxadiazol-5-ol To the solution of N-Hydroxy-2-[4-(7-methoxy-6-methyl-indan-4-ylmethyl)-3,5-dimethyl-pyrazol-1-yl]-acetamidine (2.4 gm, 0.00701 mole) in Pyridine (50 ml), Ethyl chloroformate (1.5 ml, 0.0157 mole) was added at 0-5° C. The reaction mixture was stirred for 15 minutes and Pyridine was distilled under vacuum. To the obtained residue, the mixture of water and Tetrahydrofuran (1:1) 40 ml and 1M Sodium hydroxide solution (10 ml) were added and stirred at 75° C. for an hour and continued for 24 hours at 25-28° C. To the reaction mixture, 2M Hydrochloric acid (200 ml) was added and extracted with Ethyl acetate (2×100 ml). Ethyl acetate layer was dried over sodium sulphate and distilled under vacuum to give a 2.0 gm solid. The obtained solid was taken in mixture of Tetrahydrofuran (5 ml) and 1M Sodium hydroxide (50 ml) and refluxed for 24 hours. The reaction mixture was cooled and 2N hydrochloric acid (100 ml) was added. The separated solid was filtered, washed with water (20 ml) and dissolved in Ethylacetate (100 ml). The Ethyl acetate layer was dried over Sodium sulphate and distilled under vacuum to give 880 mg of desired product as a solid Yield: 34.10%

$^1$H-NMR (400 MHz, DMSO-$d_6$): δ 6.52 (1H, s), 5.14 (2H, s), 3.64 (3H, s), 3.51 (2H, s), 2.86 (2H, t), 2.74 (2H, t), 2.13 (3H, s), 2.08 (3H, s), 1.95-2.03 (2H, m), 1.94 (3H, s).

Step-IV: Preparation of 3-[4-(7-Hydroxy-6-methyl-indan-4-ylmethyl)-3,5-dimethyl-pyrazol-1-ylmethyl]-[1,2,4]oxadiazol-5-ol It was prepared by using similar method as described for step-VI of example-2

Yield: 79.5%

$^1$H-NMR (400 MHz, DMSO-$d_6$): δ 8.15 (1H, s), 6.44 (1H, s), 5.14 (2H, s), 3.46 (2H, s), 2.68-2.77 (4H, m), 2.13 (3H, s), 2.03 (3H, s), 1.87-1.99 (5H, m).

Mass: 353 (M$^+$−1)

Example-10

Compound No. 66

Propane-2-sulfonic acid {3-[4-(7-methoxy-6-methyl-indan-4-ylmethyl)-3,5-dimethyl-pyrazol-1-yl]-propionyl}-amide To the suspension of 60% Sodium hydride (76 mg, 0.0019 mole) in Tetrahydrofuran (2 ml), the solution of 3-[4-(7-Methoxy-6-methyl-indan-4-ylmethyl)-3,5-dimethyl-pyrazol-1-yl]-propionamide (500 mg, 0.00146 mole) in Tetrahydrofuran (5 ml) was added at room temperature and stirred for 20 minutes. A solution of Isopropyl sulfonyl chloride (0.18 ml, 0.0016 moles) in Tetrahydrofuran (3 ml) was added at 0-5° C. and stirred at 15-25° C. for 3 hours. Tetrahydrofuran was distilled under vacuum, dilute hydrochloric acid (20 ml) was added to the reaction mixture and extracted with Ethyl Acetate (50 ml). The Ethyl acetate layer was dried over Sodium sulphate and distilled under vacuum to give a crude product which was purified by column chromatography using Ethylacetate as a mobile phase. The fractions were distilled to give 80 mg of desired compound as a solid.

Yield: 12.2%
$^1$H-NMR (400 MHz, DMSO-$d_6$): δ 11.50 (1H, bs), 6.49 (1H, s), 4.12 (2H, t), 3.64 (3H, s), 3.51-3.55 (1H, m), 3.47 (2H, s), 2.80-2.88 (4H, m), 2.73 (2H, t), 2.09 (3H, s), 2.08 (3H, s), 1.96-2.03 (2H, m), 1.91 (3H, s), 1.20 (6H, d).
Mass: 446 (M$^+$−1)

Example-11

Compound No. 12

7-[1-(2-Hydroxy-ethyl)-3,5-dimethyl-1H-pyrazol-4-ylmethyl]-5-methyl-indan-4-ol

Step-I: Preparation of 3-(7-Methoxy-6-methyl-indan-4-ylmethyl)-pentane-2,4-dione To the solution of 7-Methoxy-6-methyl-indan-4-carbaldehyde (8.0 gm 0.042 mole) and Acetyl acetone (4.63 gm, 0.046 mole) in Toluene (80 ml), Piperidine (0.5 ml) and Acetic acid (0.5 ml) were added. The reaction mixture was refluxed over 3A° molecular sieve using dean stark apparatus for 24 hours. Toluene was distilled under vacuum to give a crude product, which was purified by column chromatography using 5% Ethyl acetate in Hexane. The fractions were distilled to give 3.0 gm of condensed product It was dissolved in Methanol (60 ml) and hydrogenation was carried out over 5% w/w Palladium on Barium sulphate (350 mg) at 40-50 psi. using Hydrogen gas at 25-30° C. The reaction mixture was filtered through hyflow bed and distilled under vacuum to give a 2.9 gm of desired compound as a viscous oil.

Yield: 25.1%
Mass: 274 (M$^+$−1)

Step-II: Preparation of 2-[4-(7-Methoxy-6-methyl-indan-4-ylmethyl)-3,5-dimethyl-pyrazol-1-yl]-ethanol To a stirred solution of 3-(7-Methoxy-6-methyl-indan-4-ylmethyl)-pentane-2,4-dione (1.0 gm 0.0036 mole) in Ethanol (15 ml), a solution of 2-Hydrazino-ethanol (0.33 gm, 0.0043 mole) in Ethanol (5 ml) was added at 25-30° C. and reaction mixture was heated to 70° C. for an hour. The Acetic acid (2 ml) was added. Further the reaction mixture was stirred at 70° C. for 3 hours Ethanol was distilled under vacuum to give a residue which was partitioned between Ethyl acetate (50 ml) and water (25 ml). Ethyl acetate was distilled under vacuum to give a crude product The crude product was solidified after stirring in Diethyl ether (10 ml). The solid was filtered under vacuum and dried to give a 700 mg of desired compound as a solid.

Yield: 61.4%
Mass: 315 (M$^+$+1)

Step-III: Preparation of 7-[1-(2-Hydroxy-ethyl)-3,5-dimethyl-1H-pyrazol-4-ylmethyl]-5-methyl-indan-4-ol It was prepared by using similar method as described for step-VI of example-2

Yield: 45.4%
$^1$H-NMR (400 MHz, DMSO-$d_6$): δ 8.11 (1H, s), 6.43 (1H, s), 4.80 (1H, t), 3.95 (2H, t), 3.63 (2H, q), 3.43 (2H, s), 2.69-2.77 (4H, m), 2.08 (3H, s), 2.03 (3H, s), 1.92-1.99 (5H, m).
Mass: 301 (M$^+$+1)

Following is the Process for the Preparation of Intermediates, which Were Used for the Preparation of Compounds Mentioned in Table-1:

PREPARATION OF INTERMEDIATES

1: Preparation of 7-Methoxy-6-methyl-indan-4-carbaldehyde

Method-1

Step-I: Preparation of 8-Methyl coumarin

The suspension of 2-Hydroxy-3-methyl benzaldehyde (30 gm, 0.220 mole) and anhydrous Sodium acetate (45 gm, 0.55 mole) in Acetic anhydride (45 gm, 0.44 mole) was heated at 175-180° C. for 6 hours. The reaction mixture was cooled; water (150 ml) and Hexane (60 ml) were added. It was stirred for an hour and filtered. The obtained solid was stirred with Diethyl ether (30 ml). Finally the suspension was filtered and dried to give 19 gm desired product.

Yield: 85%
NMR (400 mhz, CDCl$_3$): δ 7.69 (1H, d), 7.35-7.37 (1H, m), 7.30-7.32 (1H, m), 7.16 (1H, t), 6.39 (1H, d), 2.44 (3H, s).

Step-II: Preparation of 8-Methyl dihydrocoumarin

To a solution of 8-Methyl coumarin (16.2 gm) in Ethyl acetate (160 ml), 10% w/w Palladium-charcoal (1.62 gm) was added. Hydrogenation was carried out for 5 hours at 55-60° C. in an autoclave at 240-250 psi. using Hydrogen gas. The reaction mixture was filtered through hyflow bed and distilled under vacuum to give a 14.5 gm of title compound as a white solid.

Yield: 90%
NMR (400 mhz, DMSO-$d_6$): δ 7.10-7.14 (2H, m), 7.01 (1H, t), 2.93-2.97 (2H, m), 2.73-2.76 (2H, m), 2.21 (3H, s).

Step-III: Preparation of 4-Hydroxy-5-methyl-indan-1-one

The mixture of 8-Methyl dihydrocoumarin (20 gm, 0.123 mole) and Aluminum trichloride (49.3 gm, 0.370 mole) was stirred for 2 hours at 175-180° C. To the reaction mixture, water (250 ml) was added slowly and stirred for an hour. Further it was filtered and obtained solid was stirred in Methanol (60 ml). Finally the suspension was filtered and obtained solid was dried under vacuum to give 13.5 gm of desired product as a solid.

Yield: 67.5%

NMR (400 mhz, DMSO-$d_6$): δ 9.22 (1H, s), 7.15 (1H, d), 7.04 (1H, d), 2.96 (2H, t), 2.59 (2H, t), 2.24 (3H, s)

Step-IV: Preparation of 5-Methyl-indan-4-ol

To a suspension of 4-Hydroxy-5-methyl-indan-1-one (8 gm) in Methanol (80 ml), added 10% w/w Pd—C. Hydrogenation was carried out for 5 hours at 55-60° C. in an autoclave at 200-250 psi using Hydrogen gas. The reaction mixture was filtered through hyflow bed and filtrate was distilled under vacuum to give a 6.0 gm of desired product as white solid.

Yield: 82.2%

NMR (400 mhz, DMSO-$d_6$): δ 8.36 (1H, s), 6.82 (1H, d), 6.58 (1H, d), 2.73-2.79 (4H, m), 2.10 (3H, s), 1.92-1.99 (2H, m)

Step-V: Preparation of 7-Hydroxy-6-methyl-indan-4-carbaldehyde

To a clear solution of 5-Methyl-indan-4-ol (6 gm, 0.0405 mole) in 30 ml Trifluoroacetic acid, Hexamine (5.7 gm, 0.0405 mole) was added at 25-28° C. The reaction mixture was heated and stirred at 85-90° C. for 6 hours. The cooled reaction mixture was poured into saturated Sodium bicarbonate solution and extracted with Ethylacetate (2×200 ml). The organic layer was dried over Sodium sulphate and distilled under vacuum to give a crude product which was purified by column chromatography using Ethyl acetate:Hexane (10:90) as mobile phase The collected fractions were distilled to give 5.4 gm of desired product as a solid.

Yield: 76%

NMR (400 mhz, DMSO-$d_6$): δ 9.87 (1H, s), 9.63 (1H, bs), 7.44 (1H, s), 3.14 (2H, t), 2.79 (2H, t), 2.18 (3H, s), 1.99-2.08 (2H, m).

Step-VI: Preparation of 7-Methoxy-6-methyl-indan-4-carbaldehyde

To a stirred suspension of 6-Methyl-7-hydroxy-indan-4-carbaldehyde (5 gm, 0.0284 mole) and Potassium carbonate (4.7 gm, 0.0340 mole) in dimethyl formamide, Methyl iodide (2.2 ml, 0.0312 mole) was added at 0° C. The reaction mixture was stirred at 25-30° C. for 4 hours, then water (200 ml) was added and extracted with Ethylacetate (2×100 ml). The Ethylacetate layer was dried over Sodium sulphate and evaporated to give a crude mass which was purified by column chromatography using Ethyl acetate:Hexane (10:90) as a mobile phase. The fractions were distilled under vacuum to give 4.8 gm of desired product as viscous oil.

Yield: 88.9%

NMR (400 mhz, DMSO-$d_6$): δ 9.97 (1H, s), 7.50 (1H, s), 3.84 (3H, s), 3.14 (2H, t), 2.96 (2H, t), 2.22 (3H, s), 2.01-2.08 (2H, m)

MASS: 191 ($M^+$+1)

Method-2

Step-I: Preparation of 4-Hydroxy-indan-5-carbaldehyde

To a stirred suspension Magnesium chloride (71.0 gm, 0.745 mole) and Para-formaldehyde (33.6 gm, 1.12 mole) in Tetrahydrofuran (200 ml), Triethylamine (104 ml, 0.745 mole) was added at room temperature and stirred for 30 minutes. To the reaction mixture; the solution of Indan-4-ol (50 gm, 0.373) in Tetrahydrofuran (100 ml) was added at room temperature and heated to 70-75° C. for 6 hours. To the reaction mixture, 2N Hydrochloric acid (600 ml) was added and extracted with Ethylacetate (2×500 ml). The Ethylacetate layer was washed with water (300 ml), dried over Sodium sulphate and further it was distilled under vacuum to give viscous oil (52.0 gm) which becomes solid upon keeping.

Yield: 86.0%

NMR (400 mhz, DMSO-$d_6$): δ 10.76 (1H, s), 10.04 (1H, s), 7.55 (1H, d), 6.95 (1H, d), 2.91 (2H, t), 2.83 (2H, t), 2.02-2.09 (2H, m)

Step-II: Preparation of 5-Methyl-indan-4-ol

To a solution of 4-Hydroxy-indan-5-carbaldehyde (5 gm) in Methanol (80 ml), 10% wt/wt Palladium-charcoal (500 mg) was added. The hydrogenation was carried out for 8 hours at 55-60° C. in an autoclave at 240-250 psi using Hydrogen gas. The reaction mixture was filtered through hyflow bed and distilled under vacuum to give 4.0 gm of title compound as a solid.

Yield: 88.0%

Step-III: Preparation of 7-Hydroxy-6-methyl-indan-4-carbaldehyde

It is prepared using procedure same as described for step-V of method-1 for preparation of intermediate 1.

Step-IV: Preparation of 7-Methoxy-6-methyl-indan-4-carbaldehyde

It is prepared using procedure same as described for step-V of method-1 for preparation of intermediate 1.

2: Preparation of 7-Methoxy-6-(4-methyl-benzyl)indan-4-carbaldehyde

Step-I: Preparation of 4-Methoxy-indan-5-carbaldehyde

To a stirred suspension of 4-Hydroxy-indan-5-carbaldehyde (52.0 gm, 0.320 mole) and Potassium carbonate (57.2 gm, 0.414 mole) in Dimethylformamide (200 ml) solution of Methyl iodide (22 ml, 0.351 mole) in 60 ml Dimethylformamide was added at 0-5° C. The reaction mixture was stirred at 25-28° C. for 4 hours and then poured into water (200 ml), further it was extracted with Ethyl acetate (2×500 ml). The organic layer was dried over Sodium sulphate, distilled under vacuum to give crude product which was purified through column chromatography using Ethyl acetate:Hexane (3:97) as mobile phase. The collected fractions were distilled under vacuum to give 30 gm of desired product as a viscous oil.

Yield: 53.0%

NMR (400 mhz, DMSO-$d_6$): δ 10.26 (1H, s), 7.54 (1H, d), 7.12 (1H, d), 3.92 (3H, s), 3.01 (2H, t), 2.91 (2H, t), 2.03-2.10 (2H, m).

Step-II: Preparation of 4-Methoxy-5-(4-methyl-benzyl)-indan

To a stirred suspension of Magnesium turning (1.36 gm, 0.056 mole) in 60 ml Diethyl ether, added 4-Bromo toluene (8.7 ml, 0.071 mole) in 20 ml Diethyl ether at 30-40° C. under nitrogen atmosphere. Further It was stirred at 30-40° C. for 45 minutes. The solution of 4-Methoxy-indan-5-carbaldehyde (5.0 gm, 0.0284 mole) in 20 ml Diethyl ether was added to the reaction mixture at room temperature. After an hour room temperature stirring, dilute Hydrochloric acid was added and extracted with Ethylacetate (2×100 ml). The organic layer was dried over Sodium sulphate, distilled under vacuum to give 8.0 gm crude alcohol which was taken with Triethyl silane (40.0 ml, 0.250 mole) and added Trifluoroacetic acid (80 ml) at 0-5° C. After stirring at 70° C. for 5 hours, reaction mixture was poured into saturated Sodium bicarbonate solution and extracted with Ethyl acetate (2×100 ml). The Ethyl acetate layer was dried over Sodium sulphate and distilled to give a crude mass which was purified by column chromatography using Ethyl acetate:Hexane (3:97) as a mobile phase. The fractions were distilled to give 5.6 gm of pure product as viscous oil.

Yield: 78.2%

NMR (400 mhz, DMSO-$d_6$): δ 7.05-7.07 (4H, s), 6.90 (1H, d), 6.87 (1H, d), 3.82 (2H, s), 3.62 (3H, s), 2.88 (2H, t), 2.79 (2H, t), 2.23 (3H, s), 1.95-2.01 (2H, m).

Step-III: Preparation of 7-Methoxy-6-(4-methyl-benzyl)-indan-4-carbaldehyde

It is prepared using procedure same as described for step-V of method-1 for preparation of intermediate 1.

Yield: 21%

NMR (400 mhz, DMSO-$d_6$): δ 9.97 (1H, s), 7.49 (1H, s), 7.07 (4H, s), 3.89 (2H, s), 3.78 (3H, s), 3.16 (2H, t), 2.97 (2H, t), 2.24 (3H, s), 2.02-2.09 (2H, m).

MASS: 281 ($M^+$+1)

3. Preparation of 7-Methoxy-3,6-dimethyl-indan-4-carbaldehyde

Step-I: synthesis of 4-Methoxy-5-methyl-indan-1-one

To a suspension of 4-Hydroxy-5-methyl-indan-1-one (50.0 gm, 0.308 mole) and Potassium carbonate (127.0 gm, 0.928 mole) in Dimethylformamide (250 ml), Dimethyl sulphate (90 ml, 0.928 mole) was added at 0° C. The reaction mixture was heated at 60-65° C. and stirred for 16 hours. The reaction mixture was poured into water (1 liter) and extracted with Ethylacetate (3×250 ml). The organic layer was dried over Sodium sulphate and distilled under vacuum to give 10.0 gm of crude product which was purified by column chromatography using Hexane as a mobile phase. The collected fractions were distilled under vacuum to give 45.0 gm of desired product as a viscous oil.

Yield: 82.5%

NMR (400 mhz, DMSO-$d_6$): δ 7.30 (1H, d), 7.27 (1H, d), 3.84 (3H, s), 3.12 (2H, t), 2.60-2.63 (2H, m), 2.31 (3H, s).

Step-II: Synthesis of 4-Methoxy-1,5-dimethyl-indan

To a suspension of Magnesium turning (2.72 gm, 0.113 mole) in Diethyl ether (40 ml), a solution of Methyl iodide (13.7 ml, 0.219 mole) in Diethyl ether (10 ml) was added slowly at 30-35° C. under nitrogen atmosphere. The reaction mixture was stirred for an hour at room temperature and then a solution of 4-Methoxy-5-methyl-indan-1-one (10.0 gm, 0.0568 mole) in Diethyl ether (30 ml) was added at 0° C. The reaction mixture was stirred for an hour at room temperature and then dilute Hydrochloric acid (50 ml) was added. It was extracted with Ethylacetate (3×50 ml). The organic layer was dried over Sodium sulphate, distilled under vacuum to give 10.0 gm of crude alcohol. The obtained alcohol was taken with Triethyl silane (41.3 ml, 0.258 mole) and added Trifluoroacetic acid (100 ml) at 0° C. The reaction mixture was stirred at 65-70° C. for 4 hours and poured into saturated Sodium bicarbonate solution. It was extracted with Ethylacetate (2×100 ml), dried over Sodium sulphate, distilled under vacuum to give a crude mass which was purified by column chromatography using Hexane as a mobile phase. The collected fractions were distilled under vacuum to give 5.0 gm of desired product as a viscous oil.

Yield: 50%

NMR (400 mhz, DMSO-$d_6$): δ 6.96 (1H, d), 6.81 (1H, d), 3.69 (3H, s), 3.04-3.10 (1H, m), 2.87-2.94 (1H, m), 2.73-2.81 (1H, m), 2.21-2.28 (1H, m), 2.15 (3H, s), 1.46-1.55 (1H, m), 1.20 (3H, d).

Step-III: synthesis of 7-Methoxy-3,6-dimethyl-indan-4-carbaldehyde

It is prepared using procedure same as described for step-V of method-1 for preparation of intermediate 1.

Yield: 43.1%

NMR (400 mhz, DMSO-$d_6$): δ 9.98 (1H, s), 7.52 (1H, s), 3.86 (3H, s), 3.76-3.79 (1H, m), 2.89-3.08 (2H, m), 2.12-2.21 (4H, m), 1.79-1.84 (1H, m), 1.12 (3H, d).

4: Preparation of 7-Methoxy-6-methyl-2-(4-nitro-phenoxy)-indan-4-carbaldehyde

Step-I: synthesis of 2-Bromo-4-methoxy-5-methyl-indan-1-one

To a stirred solution of 4-Methoxy-5-methyl-indan-1-one (5.0 gm, 0.0284 mole) in Acetic acid (65 ml) and Hydrobromic acid (1 ml), a solution of Bromine (1.47 ml, 0.0284 mole) in 5 ml Acetic acid was added at 10-20° C. The reaction mixture was stirred at 20-25° C. for an hour. Then it was poured into saturated solution of Sodium bicarbonate and extracted with Diethyl ether (3×100 ml). The organic layer was dried over Sodium sulphate, distilled under vacuum to give crude product which was purified over column chromatography using Ethyl acetate:Hexane (5:95) as a mobile phase. The collected fractions were distilled to give 3.2 gm of desired product as a viscous oil.

Yield: 44.2%

NMR (400 mhz, DMSO-$d_6$): δ 7.44 (1H, d), 7.38 (1H, d), 5.00-5.03 (1H, m), 3.89-3.97 (1H, m), 3.84 (3H, s), 3.31-3.36 (1H, merged with water peak present in DMSO-$d_6$), 2.33 (3H, s).

Step-II: synthesis of 4-Methoxy-5-methyl-2-(4-nitro-phenoxy)-indan-1-one

To a stirred solution of 2-Bromo-4-methoxy-5-methyl-indan-1-one (2.0 gm, 0.0078 mole) in Dimethylformamide (15 ml), added Sodium salt of 4-Nitrophenol (1.27 gm, 0.0078 mole) at 10-15° C. After 2 hours stirring at 25-28° C., reaction mixture was poured into water (50 ml). The separated solid was filtered, washed with hexane and dried under vacuum to give 1.8 gm of desired product as a solid Yield: 73.4%

NMR (400 mhz, DMSO-$d_6$): δ 8.26 (2H, d), 7.30-7.43 (4H, m), 5.58 (1H, dd), 3.89-3.95 (1H, m), 3.85 (3H, s), 3.10-3.15 (1H, m), 2.34 (3H, s).

Step-III: Synthesis of 4-Methoxy-5-methyl-2-(4-nitro-phenoxy)-indan

To a mixture of 4-Methoxy-5-methyl-2-(4-nitro-phenoxy)-indan-1-one (1.8 gm, 0.0057 mole) and Triethyl silane (9.0 ml, 0.0564 mole), Trifluoroacetic acid (18 ml) was added at 20-25° C. The reaction mixture was heated to 60-65° C. for 3 hours and then poured into saturated Sodium bicarbonate solution. It was extracted with Ethylacetate (2×100 ml), dried over Sodium sulphate, distilled under vacuum to give a crude product which was purified by column chromatography using Ethyl acetate:Hexane (2:98) as a mobile phase. The collected fractions were distilled under vacuum to give 1.2 gm of desired product as a solid.

Yield: 69.7%

NMR (400 mhz, DMSO-$d_6$): δ 8.22 (2H, d), 7.18 (2H, d), 7.02 (1H, d), 6.91 (1H, d), 5.40-5.43 (1H, m), 3.71 (3H, s), 3.38-3.51 (2H, m), 2.99-3.10 (2H, m), 2.18 (3H, s).

Step-IV: Synthesis of 7-Methoxy-6-methyl-2-(4-nitro-phenoxy)-indan-4-carbaldehyde It is prepared using procedure same as described for step-V of method-1 for preparation of intermediate 1.

Yield: 93.1%

NMR (400 mhz, DMSO-$d_6$): δ 9.95 (1H, s), 8.19 (2H, d), 7.61 (1H, s), 7.19 (2H, d), 5.47-5.50 (1H, m), 3.88 (3H, s), 3.55-3.70 (2H, m), 3.42-3.46 (1H, m), 3.17-3.21 (1H, m), 2.25 (3H, s).

MASS: 328 ($M^+$−1)

5: Preparation of 7-Methoxy-2,2,6-trimethyl-indan-4-carbaldehyde

Step-I: Preparation of 4-Methoxy-2,2,5-trimethyl-indan-1-one

To a suspension of 60% Sodium hydride (2.72 gm, 0.068 mole) in 30 ml Tetrahydrofuran, a solution of 4-Methoxy-5-methyl-indan-1-one (10.0 gm, 0.0568 mole) in Tetrahydrofuran (30 ml) was added at 0-5° C.; further to this, Methyl iodide (9.09 ml, 0.146 mole) was added at 0° C. The reaction mixture was stirred for 2 hours, then water (100 ml) was added and extracted with Ethylacetate (2×100 ml). The Ethylacetate layer was dried over Sodium sulphate and evaporated to give a crude mass which was purified over column chromatography using Ethyl acetate:Hexane (3:97) as mobile phase. The fractions were distilled under vacuum to give 3.0 gm of desired product as viscous oil.

Yield: 25.88%

NMR (400 mhz, DMSO-$d_6$): δ 7.31 (1H, d), 7.29 (1H, d), 3.83 (3H, s), 3.03 (2H, s), 2.30 (3H, s), 1.14 (6H, s).

Step-II: Preparation of 4-Methoxy-2,2,5-trimethyl-indan

It is prepared using procedure same as described for step-III of preparation of intermediate 4.

Yield: 92.3%

NMR (400 mhz, DMSO-$d_6$): δ 6.99 (1H, d), 6.79 (1H, d), 3.68 (3H, s), 2.70 (2H, s), 2.62 (2H, s), 2.14 (3H, s), 1.10 (6H, s).

Step-III: Preparation of 7-Methoxy-2,2,6-trimethyl-indan-4-carbaldehyde

It is prepared using procedure same as described for step-V for method-1 preparation of intermediate 1.

Yield: 50.8%

NMR (400 mhz, DMSO-$d_6$): δ 9.95 (1H, s), 7.51 (1H, s), 3.83 (3H, s), 2.98 (2H, s), 2.80 (2H, s), 2.21 (3H, s), 1.12 (6H, s).

6: Preparation of 7-Methoxy-6-(pyrrolidine-1-carbonyl)-indan-4-carbaldehyde

Step-I: Preparation of 4-Methoxy-indan-5-carboxylic acid

To a clear solution of 4-Methoxy-indan-5-carbaldehyde (11.5 gm, 0.065 mole) in Dichloromethane (100 ml), Sulphamic acid (19.0 gm, 0.196 mole) was added at 25-28°. A solution of Sodium chlorite (15.28 gm, 0.169 mole) in water (50 ml) was added at 5-10° C. The reaction mixture was stirred for 5 hours at 25-28° C. Finally the reaction mixture was poured into water (200 ml) and extracted with Dichloromethane (2×200 ml). The organic layer was dried over Sodium sulphate, distilled under vacuum to give 12.0 gm of desired product as a viscous oil.

Yield: 96.0%

MASS: 191 ($M^+$−1)

Step-II: Preparation of (4-Methoxy-indan-5-yl)-pyrrolidin-1-yl-methanone

To a clear solution of 4-Methoxy-indan-5-carboxylic acid (12.0 gm, 0.0625 mole) in Tetrahydrofuran (60 ml), Carbonyl-diimidazole (13.24 gm, 0.0812 mole) was added at 25-28° C. The reaction mixture was heated to 65-70° C. and stirred for 2 hours to the reaction mixture, a solution of Pyrrolidine (5.74 ml, 0.0687 mole) in Tetrahydrofuran (20 ml) was added at 10-15° C. The reaction mixture was poured into water (200 ml) and extracted with Ethylacetate (2×100 ml). The organic layer was dried over Sodium sulphate, distilled under vacuum and purified by column chromatography using Ethyl acetate:Hexane (20:80) as mobile phase. The fractions were distilled under vacuum to give 6.0 gm of desired product as a viscous oil.

Yield: 39.2%

NMR (400 mhz, DMSO-$d_6$): δ 6.98 (2H, s), 3.74 (3H, s), 3.44 (2H, t), 3.13 (2H, t), 2.85-2.94 (4H, m), 2.01-2.06 (2H, m), 1.75-1.88 (4H, m).

Step-III: Preparation of 7-Methoxy-6-(pyrrolidine-1-carbonyl)-indan-4-carbaldehyde It is prepared using procedure same as described for step-V of method-1 for preparation of intermediate 1.

Yield: 71.7%

NMR (400 mhz, DMSO-$d_6$): δ 10.0 (1H, s), 7.60 (1H, s), 3.88 (3H, s), 3.46-3.49 (2H, m), 3.16-3.24 (4H, m), 2.97 (2H, t), 2.05-2.13 (2H, m), 1.80-1.92 (4H, m).

MASS: 298 ($M^+$+1)

7: Preparation of 7-Methoxy-6-(4-methoxy-phenyl)-indan-4-carbaldehyde

Step-I: Preparation of 6-Bromo-7-methoxy-indan-4-carbaldehyde

To a solution of 4-Hydroxy-indane (10.0 gm, 0.0746 mole) and Diisopropylamine (1 ml) in Dichloromethane (100 ml), N-Bromo succinimide (13.28 gm, 0.0746 mole) was added slowly at 5-15° C. The reaction mixture was stirred for 20 hours. Dichloromethane was distilled and residue was partition between water (100 ml) and Diethylether (200 ml). Diethylether was distilled under vacuum to give crude solid (14.4 gm). solid was dissolved in Trifluoroacetic acid (100 ml) and added Hexamine (8.4 gm, 0.06 mole) at 25-28° C. Further the reaction mixture was heated to 85-90° C. for 4 hours. The reaction mixture was poured into saturated Sodium bicarbonate solution and extracted with Ethylacetate (3×100 ml). The organic layer was dried over Sodium sulphate, distilled under vacuum to give crude mass which was purified over column chromatography using Ethyl acetate: Hexane (3:97) as mobile phase. The collected fractions were distilled to give 7.34 gm of aldehyde. Finally to the solution of obtained aldehyde (7.34 gm, 0.0304 mole) in Dimethylformamide (30 ml), Potassium carbonate (6.3 gm, 0.0463 mole) was added and stirred for an hour. To the reaction mixture, Methyl iodide (2.9 ml, 0.0463 mole) was added at 0-5° C. and stirred at 20-25° C. for 4 hours. Then, the water (100 ml) was added and extracted with Diethyl ether (3×100 ml). The Diethyl ether was dried over Sodium sulphate and distilled to give a crude product which was purified over column chromatography using Ethyl acetate:Hexane (2:98). The fractions were distilled under vacuum to give 1.06 gm of title compound as a solid Yield: 5.5%

NMR (400 mhz, DMSO-$d_6$): δ 9.97 (1H, s), 7.91 (1H, s), 3.91 (3H, s), 3.16 (2H, t), 3.03 (2H, t), 2.04-2.12 (2H, m).

Step-II: Preparation of 7-Methoxy-6-(4-methoxyphenyl)-indan-4-carbaldehyde

To a suspension of 6-Bromo-7-methoxy-indan-4-carbaldehyde (0.2 gm, 0.00078 mole), 4-Methoxyphenyl boronic acid (0.122 gm, 0.0008 mole) and Potassium carbonate (0.27 gm, 0.0019 mole) in Toluene (5 ml) and water (5 ml), Tetrakis (triphenylphosphine) palladium(0) (2 mg) was and heated to 85-90° C. and stirred for 6 hrs. Toluene was distilled off and the obtained residue was dissolved in Diethyl ether (50 ml). Further it was washed with water (20 ml) and ether was distilled under vacuum to give a crude mass which was purified by column chromatography using Ethyl acetate:Hexane (1:99) as a mobile phase. The fractions were distilled to give 50 mg of desired product as a solid.

Yield: 22.7%

NMR (400 mhz, DMSO-$d_6$): δ 10.05 (1H, s), 7.65 (1H, s), 7.45 (2H, d), 7.01 (2H, d), 3.80 (3H, s), 3.61 (3H, s), 3.22 (2H, t), 2.99 (2H, t), 2.07-2.15 (2H, m).

MASS: 283 (M$^+$+1)

8: Preparation of 6-Chloro-7-methoxy-indan-4-carbaldehyde

Step-I: Preparation of 5-Chloro-indan-4-ol

To a clear solution of Indan-4-ol (40.0 gm, 0.297 mole) and Diisopropylamine (4.29 ml, 0.029 mole) in Dichloromethane (140 ml), a solution of Sulfuryl chloride (21.76 ml, 0.267 mole) in Dichloromethane (20 ml) was added at 0-5° C. The reaction mixture was stirred for 15 hours at 20-25° C. and poured into water (200 ml). Further it was extracted with Ethylacetate (2×200 ml). The organic layer was dried over Sodium sulphate, distilled under vacuum to give crude solid which was purified by column chromatography using Ethyl acetate:Hexane (2:98) as mobile phase. The collected fractions were distilled to give 5.7 gm of desired product as a solid.

Yield: 11.4%

NMR (400 mhz, DMSO-$d_6$): δ 9.28 (1H, s), 7.08 (1H, d), 6.80 (1H, d), 2.79-2.83 (4H, m), 1.97-2.04 (2H, m).

Step-II: Preparation of 6-Chloro-7-hydroxy-indan-4-carbaldehyde

It is prepared using procedure same as described for step-V of method-1 for preparation of intermediate 1.

Yield: 81.2%

NMR (400 mhz, DMSO-$d_6$): δ 9.85 (1H, s), 7.67 (1H, s), 3.14 (2H, t), 2.81 (2H, t), 1.99-2.04 (2H, m).

Step-III: Preparation of 6-Chloro-7-methoxy-indan-4-carbaldehyde

It is prepared using procedure same as described for step-VI of method-1 for preparation of intermediate 1.

Yield: 55.7%

NMR (400 mhz, DMSO-$d_6$): δ 10.04 (1H, s), 7.84 (1H, s), 3.98 (3H, s), 3.24 (2H, t), 3.08 (2H, t), 2.11-2.19 (2H, m).

MASS: 211 (M$^+$+1)

9: Preparation of 7-Methoxy-6-methyl-indan-4-ol

The stirred solution of 7-methoxy-6-methyl-indan-4-carbaldehyde (1.0 gm, 0.0060 mole) in Methanol (20 ml), Sulphuric acid (0.6 ml) was added at room temperature. To the reaction mixture, 30% Hydrogen peroxide (1.6 ml) was added and stirred for 1 hour at 0° C. Methanol was distilled under vacuum and the residue was dissolved in Ethylacetate (50 ml), further ethyl acetate layer was washed with water and evaporated to give a crude product, which upon triturating with Hexane give 600 mg title compound as a solid.

Yield: 56%

NMR (400 mhz, DMSO-$d_6$): δ 8.78 (1H, s), 6.37 (1H, s), 3.58 (3H, s), 2.81 (2H, t), 2.69 (2H, t), 2.09 (3H, s), 1.95-1.98 (2H, m).

MASS: 177 (M$^+$−1)

Following Compounds were Prepared Using the Procedure Mentioned in Reaction Scheme as Depicted Above:

TABLE 1

| Compd No. | NAME | $^1$H-NMR (400 MHz, DMSO-$d_6$)$ | MASS | IR (KBr, CM$^{-1}$) |
|---|---|---|---|---|
| 1 | 3-[4-(7-Hydroxy-indan-4-yloxy)-3,5-dimethyl-pyrazol-1-yl]-propionic acid | δ12.27 (1H, bs), 8.77 (1H, bs), 6.42 (1H, d), 6.15 (1H, d), 4.10 (2H, t), 2.84 (2H, t), 2.71-2.78 (4H, m), 1.98-2.04 (5H, m), 1.88 (3H, s) | 315 (M$^+$ − 1) | 3215, 1702, 1653, 1599 |
| 2 | 3-[4-(1H-Indol-5-ylmethyl)-3,5-dimethyl-pyrazol-1-yl]-propionic acid | δ 12.33 (1H, bs), 10.93 (1H, s), 7.21-7.27 (3H, m), 6.85 (1H, dd), 6.31 (1H, t), 4.10 (2H, t) 3.69 (2H, s), 2.71 (2H, t), 2.17 (3H, s), 1.99 (3H, s). | 298 (M$^+$ − 1) | 3392, 1710, 1558, 1507 |
| 3 | 7-[3,5-Dimethyl-1-(1H-tetrazol-5-ylmethyl)-1H- | δ 8.85 (1H, s), 6.44 (1H, d), | 325 (M$^+$ − 1) | 3313, 1589, 1553, 1484 |

TABLE 1-continued

| Compd No. | NAME | $^1$H-NMR (400 MHz, DMSO-d$_6$)$ | MASS | IR (KBr, CM$^{-1}$) |
|---|---|---|---|---|
| | pyrazol-4-yloxy]-indan-4-ol | 6.21 (1H, d), 5.55 (2H, s), 2.84 (2H, t), 2.76 (2H, t), 2.11 (3H, s), 2.00-2.06 (2H, m), 1.88 (3H, s). | | |
| 4 | :7-{3,5-Dimethyl-1-[2-(1H-tetrazol-5-yl)-ethyl]-1H-pyrazol-4-yloxyl}-indan-4-ol | δ.8.74 (1H, bs), 6.42 (1H, d), 6.09 (1H, d), 4.33 (2H, t), 3.37 (2H, t), 2.74-2.82 (4H, m), 2.01-2.05 (2H, m), 1.89 (3H, s), 1.87 (3H, s). | 339 (M$^+$ − 1) | 3310, 1646, 1553, 1486 |
| 5 | {2-[4-(7-Hydroxy-indan-4-yloxy)-3,5-dimethyl-pyrazol-1-yl]-acetyl amino}-acetic acid | δ 12.65 (1H, bs), 8.82 (1H, s), 8.26 (1H, t), 6.43 (1H, d), 6.21 (1H, d), 4.69 (2H, s), 3.79 (2H, d), 2.85 (2H, t), 2.76 (2H, t), 1.99-2.06 (5H, m), 1.88 (3H, s). | 358 (M$^+$ − 1) | 3346, 1660, 1553, 1491 |
| 6 | :2-[4-(7-Hydroxy-indan-4-yloxy)-3,5-dimethyl-pyrazol-1-yl]-N-(1H-tetrazol-5-yl)-acetamide | δ12.48 (1H, bs), 8.80 (1H, bs), 6.44 (1H, d), 6.21 (1H, d), 5.03 (2H, s), 2.87 (2H, t), 2.77 (2H, t), 1.99-2.07 (5H, m), 1.89 (3H, s). | 368 (M$^+$ − 1) | 3226, 1712, 1620, 1555 |
| 7 | 3-[4-(7-Hydroxy-indan-4-yloxy)-3-thiophen-2-yl-pyrazol-1-yl]-propionic acid And 3-[4-(7-Hydroxy-indan-4-yloxy)-5-thiophen-2-yl-pyrazol-1-yl]-propionic acid | For major isomer δ12.41 (1H, s), 9.00 (1H, s), 7.55 (1H, s), 7.44 (1H, d), 7.29 (1H, d), 7.04-7.06 (1H, m), 6.46-6.54 (2H, m), 4.24 (2H, t), 2.73-2.84 (6H, m), 1.96-2.06 (2H, m). | 368.99 (M$^+$ − 1) | 3108, 1708, 1564, 1486 |
| 8 | 7-[1-(1H-Tetrazol-5-ylmethyl)-3-thiophen-2-yl-1H-pyrazol-4-yloxy]-indan-4-ol And 7-[1-(1H-Tetrazol-5-ylmethyl)-5-thiophen-2-yl-1H-pyrazol-4-yloxy]-indan-4-ol | For major isomer δ9.07 (1H, s), 7.69 (1H, s), 7.47 (1H, dd), 7.35 (1H, dd), 7.06-7.08 (1H, m), 6.63 (1H, d), 6.53 (1H, d), 5.67 (2H, s), 2.77-2.86 (4H, m), 1.99-2.06 (2H, m) | 379 (M$^+$ − 1) | 3243, 1732, 1550, 1483 |
| 9 | 3-[4-(7-Hydroxy-6-methyl-indan-4-ylmethyl)-3,5-dimethyl-pyrazol-1-yl]-propionic acid | δ12.31 (1H, bs), 8.11 (1H, s), 6.41 (1H, s), 4.09 (2H, t), 3.43 (2H, t), 2.68-2.77 (6H, m), 2.09 (3H, s), 2.03 (3H, s), 1.94-1.99 (2H, m) 1.91 (3H, s). | 327 (M$^+$ − 1) | 3388, 1686, 1616, 1489 |
| 10 | 5-[4-(7-Hydroxy-indan-4-yloxy)-3,5-dimethyl-pyrazol-1-ylmethyl]-1H-pyrazol-3-ol | δ8.82 (1H, bs), 6.41 (1H, d), 6.15 (1H, d), 5.22 (1H, s), 5.01 (2H, s), 2.82 (2H, t), 2.74 (2H, t), 1.93-2.06 (5H, m), 1.84 (3H, s). | 339 (M$^+$ − 1) | 3143, 1581, 1546, 1483 |
| 11 | 2-[4-(7-Hydroxy-6-methyl-indan-4-ylmethyl)-3,5-dimethyl-pyrazol-1-yl]-acetic acid | δ12.86 (1H, bs), 8.13 (1H, s), 6.44 (1H, s), 4.81 (2H, s), 3.45 (2H, s), 2.69-2.77 (4H, m), 1.89-2.03 (11H, m). | 312.9 (M$^+$ − 1) | 3392, 1730, 1569, 1485 |
| 12 | 7-[1-(2-Hydroxy-ethyl)-3,5-dimethyl-1H-pyrazol-4-ylmethyl]-5-methyl-indan-4-ol | δ8.11 (1H, s), 6.43 (1H, s), 4.80 (1H, t), 3.95 (2H, t), 3.63 (2H, q), 3.43 (2H, s), 2.69-2.77 (4H, m), 2.08 (3H, s), 2.03 (3H, s), 1.92-1.99 (5H, m). | 301 (M$^+$ + 1) | 3320, 3167, 1570, 1481 |
| 13 | [4-(1H-Indol-5-ylmethyl)-3,5-dimethyl-pyrazol-1-yl]-acetic acid | δ12.97 (1H, bs), 10.95 (1H, s), 7.25-7.27 (2H, m), 7.22 (1H, s), 6.86 (1H, dd), 6.31 (1H, s), 4.78 (2H, s), 3.71 (2H, s), 2.10 (3H, s), 1.99 (3H, s). | 284 (M$^+$ + 1) | 3401, 1712, 1640, 1470 |
| 14 | 3-[4-(7-Methoxy-6-methyl-indan-4-ylmethyl)-3,5-dimethyl-pyrazol-1-yl]-propionic acid | δ12.29 (1H, bs), 6.49 (1H, s), 4.10 (2H, t), 3.64 (3H, s), 3.48 (2H, s), 2.86 (2H, t), 2.68-2.75 (4H, m), 2.10 (3H, s), 2.08 (3H, s), 1.96-2.03 (2H, m), 1.92 (3H, s). | 342.9 (M$^+$ + 1) | 2941, 1729, 1557, 1475 |
| 15 | 7-[3,5-Dimethyl-1-(1H-tetrazol-5-ylmethyl)- | δ8.13 (1H, bs), 6.43 (1H, s), 5.53 (2H, s), 3.46 (2H, s), 2.75 (2H, | 337 (M$^+$ − 1) | 3233, 31542, 1488, 1453 |

TABLE 1-continued

| Compd No. | NAME | $^1$H-NMR (400 MHz, DMSO-d$_6$)$ | MASS | IR (KBr, CM$^{-1}$) |
|---|---|---|---|---|
| | 1H-pyrazol-4-ylmethyl]-5-methyl-indan-4-ol | t), 2.70 (2H, t), 2.17 (3H, s), 2.03 (3H, s), 1.91-1.99 (5H, m). | | |
| 16 | 7-[3,5-Diisopropyl-1-(1H-tetrazol-5-ylmethyl)-1H-pyrazol-4-ylmethyl]-5-methyl-indan-4-ol | δ8.12 (1H, s), 6.25 (1H, s), 5.56 (2H, s), 3.59 (2H, s), 3.91-3.20 (1H, m), 2.77-2.79 (4H, m), 2.65-2.68 (1H, m), 1.94-2.10 (5H, m), 1.07 (6H, d), 1.02 (6H, d). | 393 (M$^+$ − 1) | 2962, 1668, 1599, 1478 |
| 17 | 3-[3,5-Dicyclopropyl-4-(7-hydroxy-indan-4-yloxy)-pyrazol-1-yl]-propionic acid | δ12.36 (1H, bs), 8.80 (1H, s), 6.43 (1H, d), 6.14 (1H, d), 4.22 (2H, t), 2.87 (2H, t), 2.75-2.79 (4H, m), 2.02-2.07 (2H, m), 1.67-1.71 (1H, m), 1.45-1.49 (1H, m), 0.72-0.76 (2H, m), 0.62-0.67 (6H, m). | 367 (M$^+$ − 1) | :3213, 2949, 1702, 1482 |
| 18 | 3-[4-(7-Hydroxy-6-methyl-indan-4-ylmethyl)-3,5-diisopropyl-pyrazol-1-yl]-propionic acid | δ12.39 (1H, bs), 8.11 (1H, s), 6.23 (1H, s), 4.21 (2H, t), 3.55 (2H, s), 3.04-3.11 (1H, m), 2.69-2.79 (6H, m), 2.60-2.67 (1H, m), 1.93-2.03 (5H, m), 1.12 (6H, d), 1.04. (6H, d). | 383 (M$^+$ − 1) | 2963, 1716, 1584, 1481 |
| 19 | [3,5-Diethyl-4-(7-hydroxy-6-methyl-indan-4-ylmethyl)-pyrazol-1-yl]-acetic acid | δ8.14 (1H, s), 6.39 (1H, s), 4.77 (2H, s), 3.48 (2H, merged with peak of water present in DMSO-d$_6$), 2.68-2.77 (4H, m), 2.43 (2H, q), 2.30 (2H, q), 1.94-2.01 (5H, m), 1.00 (3H, t), 0.90 (3H, t). $^1$H-NMR (400 MHz, CD$_3$OD) δ6.66 (1H, s), 4.83 (2H, s), 3.59 (2H, s), 2.75-2.83 (4H, m), 2.51 (2H, q), 2.42 (2H, q), 1.91-2.07 (5H, m), 1.05 (3H, t), 0.97 (3H, t). | 341 (M$^+$ − 1) | 3398, 2931, 1718, 1476 |
| 20 | 3-[3,5-Diethyl-4-(7-hydroxy-6-methyl-indan-4-ylmethyl)-pyrazol-1-yl]-propionic acid | δ8.13 (1H, s), 6.37 (1H, s), 4.12 (2H, t), 3.47 (2H, s), 2.72-2.76 (6H, m), 2.51 (2H, merged with DMSO-d6 peak), 2.31 (2H, q), 1.97-2.01 (5H, m), 1.00 (3H, t), 0.93 (3H, t). $^1$H-NMR (400 MHz, CD$_3$OD) δ6.42 (1H, s), 4.26 (2H, t), 3.56 (2H, s), 2.79-2.83 (4H, m), 2.75 (2H, t), 2.57 (2H, q), 2.42 (2Hq), 1.98-2.07 (5H, m), 1.04 (3H, t), 0.99 (3H, t). | 355 (M$^+$ − 1) | 3380, 2951, 1707, 1554 |
| 21 | 7-[3,5-Diethyl-1-(1H-tetrazol-5-ylmethyl)-1H-pyrazol-4-ylmethyl]-5-methyl-indan-4-ol | δ8.14 (1H, bs), 6.39 (1H, s), 5.77 (2H.s), 3.49 (2H, s), 2.71-2.78 (4H, m), 2.58-2.61 (2H, q), 2.31 (2H, q), 1.92-2.07 (5H, m), 0.98 (3H, t), 0.92 (3H, t). | 365 (M$^+$ − 1) | 3464, 2951, 1578, 1477 |
| 22 | [3,5-Dicyclopropyl-4-(7-hydroxy-indan-4-yloxy)-pyrazol-1-yl]-acetic acid | δ8.82 (1H, s), 6.44 (1H, d), 6.16 (1H, d), 4.81 (2H, s), 2.88 (2H, t), 2.78 (2H, t), 1.99-2.07 (2H, m), 1.45-1.58 (2H, m), 0.58-0.70 (8H, m). | 355 (M$^+$ + 1) | 3305, 1718, 1579, 1483 |
| 23 | 3-[3,5-Diethyl-4-(1H-indol-5-ylmethyl)-pyrazol-1-yl]-propionic acid | δ12.35 (1H, bs), 10.94 (1H, s), 7.25-7.27 (2H, m), 7.21 (1H, s), 6.85 (1H, d), 6.31 (1H, s), 4.13 (2H, t), 3.73 (2H, s), 2.76 (2H, t), 2.59 (2H, q), 2.38 (2H, q), 1.03 (3H, t), 0.96 (3H, t). | 326 (M$^+$ + 1) | 3347, 1706, 1554, 1441 |
| 24 | 2-[4-(1H-Indol-5-ylmethyl)-3,5-dimethyl-pyrazol-1-yl]-ethanol | δ10.94 (1H, s), 7.25-7.27 (2H, m), 7.22 (1H.s), 6.86 (1H, d), 6.31 (1H, | 270 (M$^+$ + 1) | 3229, 2924, 1571, 1464 |

TABLE 1-continued

| Compd No. | NAME | ¹H-NMR (400 MHz, DMSO-d₆)$ | MASS | IR (KBr, CM⁻¹) |
|---|---|---|---|---|
| | | t), 4.82 (1H, t), 3.96 (2H, t), 3.70 (2H, s), 3.64 (2H, q), 2.16 (3H, s), 2.00 (3H, s). | | |
| 25 | [4-(7-Hydroxy-indan-4-yloxy)-3,5-dimethyl-pyrazol-1-yl]-acetic acid | δ8.84 (1H, bs), 6.44 (1H, d), 6.19 (1H, d), 4.70 (2H, s), 2.86 (2H, t), 2.77 (2H, t), 1.98-2.06 (5H, m), 1.88 (3H, s). | 301 (M⁺ − 1) | 3219, 1732, 1594, 1479 |
| 26 | 3-[4-(6-Chloro-7-hydroxy-indan-4-ylmethyl)-3,5-diethyl-pyrazol-1-yl]-propionic acid | δ12.33 (1H, bs), 9.04 (1H, s), 6.52 (1H, s), 4.14 (2H.t), 3.50 (2H, s), 2.73-2.83 (6H, m), 2.52 (2H, merged with DMSO-d6 peak), 2.30 (2H, q), 1.97-2.04 (2H, m), 0.99 (3H, t), 0.93 (3H, t). | 375 (M⁺ − 1) | 3394, 1696, 1579, 1469 |
| 27 | [4-(6-Chloro-7-hydroxy-indan-4-ylmethyl)-3,5-diethyl-pyrazol-1-yl]-acetic acid | δ9.05 (1H, s), 6.55 (1H, s), 4.80 (2H.s), 3.53 (2H, s), 2.76-2.84 (4H, m), 2.52 (2H, merged with DMSO-d6 peak), 2.30 (2H, q), 1.97-2.05 (2H, m), 1.00 (3H, t), 0.91 (3H, t). | 361 (M⁺ − 1) | 3408, 2952, 1719, 1475 |
| 28 | 3-{4-[7-Hydroxy-6-(pyrrolidine-1-carbonyl)-indan-4-ylmethyl]-3,5-dimethyl-pyrazol-1-yl}-propionic acid | 1H-NMR (400 MHz, CDCl3) δ11.03 (1H, bs) 6.71 (1H, s), 4.25 (2H, t), 3.51 (2H.s), 3.48-3.52 (4H, m), 2.91-2.96 (4H, m), 2.84 (2H, t), 2.08-2.16 (8H, m), 1.86-1.90 (4H, m). | 410 (M⁺ − 1) | 2958, 1711, 1563, 1432 |
| 29 | 3-[4-(6-Chloro-7-hydroxy-indan-4-ylmethyl)-3,5-dimethyl-pyrazol-1-yl]-propionic acid | δ 9.04 (1H, s), 6.67 (1H, s), 4.11 (2H, t), 3.47 (2H, s), 2.80 (2H, t), 2.69-2.76 (4H, m), 2.11 (3H, s), 1.92-2.04 (2H, m), 1.92 (3H, s). | 349 (M⁺ + 1) | 2951, 1697, 1574, 1472 |
| 30 | 1-{2-[4-(7-Hydroxy-6-methyl-indan-4-ylmethyl)-3,5-dimethyl-pyrazol-1-yl]-acetyl}-pyrrolidine-2-carboxylic acid | δ12.33 (1H, bs), 8.11 (1H, s), 6.45 (1H, s), 4.93 (2H, s), 4.22-4.25 (1H, m), 3.58 (2H, t), 3.45 (2H, s), 2.69-2.77 (4H, m), 1.83-2.16 (15H, m). | 410 (M⁺ − 1) | 3250, 1732, 1575, 1473 |
| 31 | 7-[3,5-Dimethyl-1-(1H-tetrazol-5-ylmethyl)-1H-pyrazol-4-yloxy]-5-methyl-indan-4-ol | δ8.08 (1H, bs), 6.14 (1H, s), 5.56 (2H, s), 2.77-2.82 (4H, m), 2.11 (3H, s), 1.97-2.09 (5H, m), 1.88 (3H, s). | 341 (M⁺ + 1) | 3153, 1556, 1487, 1421 |
| 32 | [4-(7-Hydroxy-6-methyl-indan-4-ylmethyl)-3,5-diisopropyl-pyrazol-1-yl]-acetic acid | δ12.80 (1H, bs), 8.19 (1H, s), 6.35 (1H, s), 4.95 (2H, s), 3.68 (2H, s), 2.96-3.06 (1H, m), 2.86-2.95 (4H, m), 2.68-2.77 (1H, m), 2.07-2.15 (5H, m), 1.18 (6H, d), 1.13 (6H, d). | 369 (M⁺ − 1) | 2965, 1733, 1550, 1483 |
| 33 | 3-[4-(7-Hydroxy-6-methyl-indan-4-ylmethyl)-3,5-dimethyl-pyrazol-1-yl]-N-isopropyl-propionamide | δ8.11 (1H, s), 7.76 (1H, d), 6.40 (1H, s), 4.08 (2H, t), 3.76-3.81 (1H, m), 3.42 (2H, s), 2.75 (2H, t), 2.69 (2H, t), 2.51 (2H, merged with DMSO-d6 peak), 2.07 (3H, s), 2.02 (3H, s), 1.90-1.99 (5H, m), 0.98 (6H, d). | 370 (M⁺ + 1) | 3293, 1743, 1641, 1560 |
| 34 | [4-(7-Hydroxy-6-methyl-indan-4-yloxy)-3,5-dimethyl-pyrazol-1-yl]-acetic acid | δ8.11 (1H, s), 6.13 (1H, s), 4.78 (2H, s), 2.77-2.83 (4H, m), 1.99-2.05 (5H, m), 1.93 (3H, s), 1.89 (3H, s). | 317 (M⁺ + 1) | 3277, 1730, 1575, 1483 |
| 35 | 3-[4-(7-Hydroxy-6-methyl-indan-4-yloxy)-3,5-dimethyl-pyrazol-1-yl]-propionic acid | δ12.38 (1H, bs), 8.05 (1H, s), 6.08 (1H, s), 4.10 (2H, t), 2.77-2.81 (4H, m), 2.72 (2H, t), 1.97-2.08 (8H, m), 1.88 (3H, s). | 331 (M⁺ + 1) | 3398, 1717, 1580, 1486 |

TABLE 1-continued

| Compd No. | NAME | $^1$H-NMR (400 MHz, DMSO-d$_6$)$ | MASS | IR (KBr, CM$^{-1}$) |
|---|---|---|---|---|
| 36 | 4-[4-(7-Hydroxy-6-methyl-indan-4-ylmethyl)-3,5-dimethyl-pyrazol-1-yl]-butyric acid | δ12.3 (1H, bs), 8.09 (1H, s), 6.40 (1H, s), 3.92 (2H, t), 3.44 (2H, s), 2.74 (2H, t), 2.69 (2H, t), 2.16 (2H, t), 2.05 (3H, s), 2.02 (3H, s), 1.83-1.98 (7H, m). | 343 (M$^+$ + 1) | 3036, 1610, 1581, 1481 |
| 37 | 3-[4-(7-Hydroxy-6-methyl-indan-4-ylmethyl)-3,5-dimethyl-pyrazol-1-yl]-N-(1H-tetrazol-5-yl)-propionamide | δ11.61 (1H, bs), 8.11 (1H, s), 6.39 (1H, s), 4.20 (2H, t), 3.42 (2H, s), 2.91 (2H, t), 2.72 (2H, t), 2.64 (2H, t), 2.10 (3H, s), 1.98 (3H, s), 1.87-1.91 (5H, m). | 396 (M$^+$ + 1) | 2918, 1711, 1484, 1402 |
| 38 | 5-[4-(7-Hydroxy-6-methyl-indan-4-ylmethyl)-3,5-dimethyl-pyrazol-1-ylmethyl]-3H-[1,3,4]oxadiazol-2-one | δ12.39 (1H, s), 8.14 (1H, s), 6.41 (1H, s), 5.17 (2H, s), 3.46 (2H, s), 2.74 (2H, t), 2.68 (2H, t), 2.12 (3H, s), 2.02 (3H, s), 1.91-1.99 (5H, m). | 355 (M$^+$ + 1) | 3150, 1793, 1483, 1434 |
| 39 | 7-{3,5-Dimethyl-1-[2-(1H-tetrazol-5-yl)-ethyl]-1H-pyrazol-4-ylmethyl}-5-methyl-indan-4-ol | δ6.34 (1H, s), 4.40 (2H, t), 3.43 (2H, s), 3.37 (2H, s), 2.74 (2H, t), 2.63 (2H, t), 2.04 (3H, s), 1.99 (3H, s), 1.91-1.96 (5H, m). | 353 (M$^+$ + 1) | 3330, 1599, 1548, 1441 |
| 40 | {2-[4-(7-Hydroxy-6-methyl-indan-4-ylmethyl)-3,5-dimetyl-pyrazol-1-yl]-acetylamino}-acetic acid | δ12.64 (1H, bs), 8.20 (1H, t), 8.11 (1H, s), 6.44 (1H, s), 4.67 (2H, s), 3.78 (2H, d), 3.45 (2H, s), 2.69-2.77 (4H, m), 2.03 (6H, s), 1.91-1.99 (5H, m). | 370 (M$^+$ − 1) | 3283, 2946, 1667, 1562 |
| 41 | 5-[4-(7-Hydroxy-6-methyl-indan-4-ylmethyl)-3,5-dimethyl-pyrazol-1-ylmethyl]-1H-pyrazol-3-ol | δ9.43 (1H, bs), 8.12 (1H, s), 6.40 (1H, s), 5.14 (1H, s), 4.99 (1H, s), 3.44 (2H, s), 2.74 (2H, t), 2.69 (2H, t), 2.08 (3H, s), 2.02 (3H, s), 1.91-1.98 (5H, m). | 353 (M$^+$ + 1) | 2948, 1589, 1476, 1442 |
| 42 | 5-[3,5-Diethyl-4-(7-hydroxy-6-methyl-indan-4-ylmethyl)-pyrazol-1-ylmethyl]-3H-[1,3,4]oxadiazol-2-one | δ12.41 (1H, s), 8.14 (1H, s), 6.37 (1H, s), 5.20 (2H, s), 3.49 (2H, s), 2.69-2.77 (4H, m), 2.53 (2H, merged with DMSO-d6 peak), 2.31 (2H, q), 1.91-2.01 (5H, m), 0.99 (3H, t), 0.92 (3H, t). | 383 (M$^+$ + 1) | 3475, 2968, 1799, 1444 |
| 43 | 5-{2-[4-(7-Hydroxy-6-methyl-indan-4-ylmethyl)-3,5-dimethyl-pyrazol-1-yl]-ethyl}-3H-[1,3,4]oxadiazol-2-one | δ12.09 (1H, s), 8.10 (1H, s), 6.39 (1H, s), 4.21 (2H, t), 3.42 (2H, s), 2.97 (2H, t), 2.74 (2H, t), 2.66 (2H, t), 2.08 (3H, s), 2.05 (3H, s), 1.89-1.99 (5H, m). | 369 (M$^+$ + 1) | 3370, 2958, 1788, 1580 |
| 44 | {2-[3,5-Diethyl-4-(7-hydroxy-6-methyl-indan-4-ylmethyl)-pyrazol-1-yl]-acetylamino}-acetic acid | δ8.20 (2H, m), 6.40 (1H, s), 4.79 (2H, s), 3.81 (2H, d), 3.49 (2H, s), 2.71-2.78 (4H, m), 2.47 (2H, merged with DMSO-d6 peak), 2.32 (2H, q), 1.85-2.01 (5H, m), 1.01 (3H, t), 0.92 (3H, t). | 400 (M$^+$ + 1) | 3363, 1707, 1676, 1552. |
| 45 | 6-[4-(7-Hydroxy-6-methyl-indan-4-ylmethyl)-3,5-dimethyl-pyrazol-1-ylmethyl]-2-methyl-3H-pyrimidin-4-one | δ12.41 (1H, s), 8.12 (1H, s), 6.42 (1H, s), 5.13 (1H, s), 4.95 (2H, s), 3.49 (2H, s), 2.67-2.77 (4H, m), 2.26 (3H, s), 2.03 (6H, s), 1.94-1.99 (5H, m). | 379 (M$^+$ + 1) | 2928, 1694, 1610, 1573. |
| 46 | 3-[4-(7-Hydroxy-6-methyl-indan-4-ylmethyl)-3,5-dimethyl-pyrazol-1-ylmethyl]-[1,2,4]oxadiazol-5-ol | δ8.15 (1H, s), 6.44 (1H, s), 5.14 (2H, s), 3.46 (2H, s), 2.68-2.77 (4H, m), 2.13 (3H, s), 2.03 (3H, s), 1.87-1.99 (5H, m). | 353 (M$^+$ − 1) | 3424, 1751, 1491, 1443. |
| 47 | 7-(1-Benzyl-3,5-dimethyl-1H-pyrazol-4-ylmethyl)-5-methyl-indan-4-ol | δ8.12 (1H, s) 7.22-7.33 (3H, m), 7.02-7.04 (2H, m), 6.40 (1H, s), 5.20 (2H, s), 3.47 (2H, s), 2.74 (2H, t), 2.68 (2H, t), 2.02 (3H, s), 2.00 (3H, s), 191-1.99 (5H, m). | 347 (M$^+$ + 1) | 2944, 1608, 1569, 1484. |
| 48 | 3-{4-[7-Hydroxy-6-(4-methyl-benzyl)-indan-4- | δ12.33 (1H, bs), 8.22 (1H, s), 6.97-7.03 (4H, m), 6.44 (1H, s), | 419 (M$^+$ + 1) | 3384, 2921, 1716, 1613. |

TABLE 1-continued

| Compd No. | NAME | $^1$H-NMR (400 MHz, DMSO-$d_6$)$ | MASS | IR (KBr, CM$^{-1}$) |
|---|---|---|---|---|
| | ylmethyl]-3,5-dimethyl-pyrazol-1-yl}-propionic acid | 4.06 (2H, t), 3.73 (2H, s), 3.41 (2H, s), 2.74 (2H, t), 2.64-2.69 (4H, m), 2.22 (3H, s), 2.03 (3H, s), 1.90-1.98 (2H, m), 1.86 (3H, s). | | |
| 49 | 2-[4-(7-Hydroxy-6-methyl-indan-4-ylmethyl)-3,5-dimethyl-pyrazol-1-yl]-propionic acid | δ12.77 (1H, s), 8.11 (1H, s), 6.43 (1H, s), 4.98 (1H, q), 3.45 (2H, s), 2.68-2.76 (4H, m), 2.05 (3H, s), 2.02 (3H, s), 1.91-1.98 (5H, m), 1.56 (3H, d). | 327 (M$^+$ − 1) | 2949, 1708, 1650, 1579. |
| 50 | 3-[4-(7-Hydroxy-6-isopropyl-indan-4-ylmethyl)-3,5-dimethyl-pyrazol-1-yl]-propionic acid | δ8.11 (1H, bs), 6.58 (1H, s), 4.08 (2H, t), 3.45 (2H, s), 3.13-3.22 (1H, m), 2.74 (2H, t), 2.63-2.68 (4H, m), 2.10 (3H, s), 1.91-1.97 (5H, m), 1.07 (6H, d). | 355 (M$^+$ − 1) | 3426, 2985, 1711, 1610. |
| 51 | {4-[7-Hydroxy-6-(4-methyl-benzyl)-indan-4-ylmethyl]-3,5-dimethyl-pyrazol-1-yl}-acetic acid | δ8.23 (1H, s), 6.95-7.01 (4H, s), 6.51 (1H, s), 4.69 (2H, s), 3.73 (2H, s), 3.44 (2H, s), 2.74 (2H, t), 2.68 (2H, t), 2.22 (3H, s), 1.91-1.97 (5H, m), 1.87 (3H, s). | 405 (M$^+$ + 1) | 2926, 1710, 1612, 1574. |
| 52 | 3-{4-[6-(4-Fluoro-benzyl)-7-hydroxy-indan-4-ylmethyl]-3,5-dimethyl-pyrazol-1-yl}-propionic acid | δ8.29 (1H, s), 7.12-7.16 (2H, m), 7.03 (2H, t), 6.45 (1H, s), 4.06 (2H, t), 3.77 (2H, s), 3.42 (2H, s), 2.75 (2H, t), 2.64-2.69 (4H, m), 2.04 (3H, s), 1.91-1.99 (2H, m), 1.86 (3H, s). | 423 (M$^+$ + 1) | 2949, 1703, 1604, 1569. |
| 53 | {4-[6-(4-Fluoro-benzyl)-7-hydroxy-indan-4-ylmethyl]-3,5-dimethyl-pyrazol-1-yl}-acetic acid | δ8.30 (1H, s), 7.13-7.17 (2H, m), 7.03 (2H, t), 6.52 (1H, s), 4.59 (2H, s), 3.77 (2H, s) 3.42 (2H, s), 2.75 (2H, t), 2.69 (2H, t), 1.79-1.98 (8H, m). | 407 (M$^+$ − 1) | 2943, 1711, 1603, 1575. |
| 54 | Sodium salt of 4-[4-(7-Hydroxy-6-methyl-indan-4-ylmethyl)-3,5-dimethyl-pyrazol-1-yl]-butyric acid, | δ6.26 (1H, s), 3.86 (2H, t), 3.35 (2H, s), 2.60-2.66 (4H, m), 2.07 (3H, s), 1.92 (3H, s), 1.90 (3H, s), 1.74-1.87 (6H, m). | 341 (M$^+$ − 1) | 1650, 1554, 1469, 1410. |
| 55 | Magnesium salt of 3-[4-(7-Hydroxy-6-methyl-indan-4-ylmethyl)-3,5-dimethyl-pyrazol-1-yl]-propionic acid | δ8.16 (1H, bs), 6.40 (1H, s), 4.06 (2H, t), 3.40 (2H, s), 2.63-2.76 (4H, m), 2.47 (2H, merged with DMSO-d6 peak), 2.07 (3H, s), 2.01 (3H, s), 1.90-1.97 (5H, m). | 327 (M$^+$ − 1) | 1678, 1612 1573, 1480. |
| 56 | Sodium salt of 3-[4-(7-Hydroxy-6-methyl-indan-4-ylmethyl)-3,5-dimethyl-pyrazol-1-yl]-propionic acid, | δ6.27 (1H, s), 4.00 (2H, t), 3.33 (2H, s), 2.61-2.68 (4H, m), 2.25 (2H, t), 2.06 (3H, s), 1.92 (6H, s), 1.76-1.86 (2H, m). | 327 (M$^+$ − 1) | 1650 1575, 1470, 1410. |
| 57 | 3-{3,5-Diethyl-4-[6-(4-fluoro-benzyl)-7-hydroxy-indan-4-ylmethyl]-pyrazol-1-yl}-propionic acid | δ12.2 (1H, bs), 8.29 (1H, s), 7.09-7.12 (2H, m), 7.01 (2H, t), 6.37 (1H, s), 4.09 (2H, t), 3.75 (2H, s), 3.45 (2H, s), 2.76 (2H, t), 2.67-2.72 (4H, m), 2.44 (2H, q), 2.23 (2H, q), 1.92-1.98 (2H, m), 0.93 (3H, t), 0.83 (3H, t). | 451 (M$^+$ + 1) | 3377, 2970, 1715, 1603. |
| 58 | 3-[4-(7-Methoxy-6-methyl-indan-4-ylmethyl)-3,5-dimethyl-pyrazol-1-yl]-3-oxo-propionic acid ethyl ester | δ6.50 (1H, s), 4.07-4.13 (4H, m), 3.66 (3H, s), 3.58 (2H, s), 2.87 (2H, t), 2.75 (2H, t), 2.43 (3H, s), 2.09 (3H, s), 1.97-2.04 (5H, m), 1.15 (3H, t). | 385 (M$^+$ + 1) | 1666, 1587, 1475, 1438 |
| 59 | [3,5-Diethyl-4-(7-methoxy-6-methyl-indan-4-ylmethyl)-pyrazol-1-yl]-acetic acid hydrazide | δ9.23 (1H, s), 6.51 (1H, s), 4.58 (2H, s), 4.29-4.30 (2H, d), 3.64 (3H, s), 3.52 (2H, s), 2.87 (2H, t), 2.76 (2H, t), 2.47 (2H, merged with DMSO-d6 | 371 (M$^+$ + 1) | 3290, 29521661, 1540. |

TABLE 1-continued

| Compd No. | NAME | $^1$H-NMR (400 MHz, DMSO-$d_6$)$ | MASS | IR (KBr, CM$^{-1}$) |
|---|---|---|---|---|
| | | peak), 2.30 (2H, q), 2.07 (3H, s), 1.97-2.04 (2H, m), 1.00 (3H, t), 0.90 (3H, t). | | |
| 60 | N-Hydroxy-2-[4-(7-methoxy-6-methyl-indan-4-ylmethyl)-3,5-dimethyl-pyrazol-1-yl]-acetamidine | δ9.20 (1H, bs), 6.52 (1H, s), 5.24 (2H, s), 4.51 (2H, s), 3.64 (3H, s), 3.49 (2H, s), 2.86 (2H, t), 2.74 (2H, t), 2.09 (6H, s), 1.98-2.05 (2H, m), 1.94 (3H, s). | 343 (M$^+$ + 1) | 3468, 2947, 1666, 1587. |
| 61 | [4-(7-Methoxy-6-methyl-indan-4-ylmethyl)-3,5-dimethyl-pyrazol-1-yl]-oxo-acetic acid ethyl ester | δ6.55 (1H, s), 4.39 (2H, q), 3.65 (3H, s), 3.62 (2H, s), 2.88 (2H, t), 2.75 (2H, t), 2.48 (3H, s), 2.09 (3H, s), 1.99-2.05 (5H, m), 1.30 (3H, t). | 371 (M$^+$ + 1) | 1758, 1725, 1483, 1399. |
| 62 | [4-(7-Methoxy-6-methyl-indan-4-ylmethyl)-3,5-dimethyl-pyrazol-1-yl]-morpholin-4-yl-methanone | δ6.53 (1H, s), 3.63-3.65 (7H, m), 3.53-3.56 (6H, m), 2.87 (2H, t), 2.74 (2H, t), 2.22 (3H, s), 2.09 (3H, s), 1.96-2.04 (5H, m). | 384 (M$^+$ + 1) | 1688, 1590, 1481, 1431. |
| 63 | 1-(4-Chloro-phenyl)-4-(7-methoxy-6-methyl-indan-4-ylmethyl)-3,5-dimethyl-1H-pyrazole | δ7.54 (4H, s), 6.59 (1H, s), 3.65 (3H, s), 3.60 (2H, s), 2.88 (2H, t), 2.79 (2H, t), 2.21 (3H, s), 2.12 (3H, s), 1.98-2.05 (5H, m). | 381 (M$^+$ + 1) | 2949, 1590, 1566, 1503. |
| 64 | 2-(4-Methanesulfonyl-phenyl)-1-[4-(7-methoxy-6-methyl-indan-4-ylmethyl)-3,5-dimethyl-pyrazol-1-yl]-ethanone | δ7.88 (2H, d), 7.60 (2H, d), 6.51 (1H, s), 4.58 (2H, s), 3.65 (3H, s), 3.60 (2H, s), 3.21 (3H, s), 2.88 (2H, t), 2.76 (2H, t), 2.41 (3H, s), 2.10 (3H, s), 1.99-2.05 (5H, m). | 467 (M$^+$ + 1) | 29411723, 1596, 1483. |
| 65 | 4-(7-Methoxy-6-methyl-indan-4-ylmethyl)-3,5-dimethyl-pyrazole-1-carboxylic acid ethyl ester | δ6.47 (1H, s), 4.35 (2H, q), 3.66 (3H, s), 3.57 (2H, s), 2.87 (2H, t), 2.75 (2H, t), 2.38 (3H, s), 2.09 (3H, s), 1.93-2.04 (5H, m), 1.32 (3H, t). | 343 (M$^+$ + 1) | 2947, 1738, 1605, 1484. |
| 66 | Propane-2-sulfonic acid {3-[4-(7-methoxy-6-methyl-indan-4-ylmethyl)-3,5-dimethyl-pyrazol-1-yl]-propionyl}-amide | δ11.50 (1H, bs), 6.49 (1H, s), 4.12 (2H, t), 3.64 (3H, s), 3.51-3.55 (1H, m), 3.47 (2H, s), 2.80-2.88 (4H, m), 2.73 (2H, t), 2.09 (3H, s), 2.08 (3H, s), 1.96-2.03 (2H, m), 1.91 (3H, s), 1.20 (6H, d). | 446 (M$^+$ − 1) | 2943, 1710, 1462, 1406 |
| 67 | 3-[5-Ethoxy-4-(7-methoxy-6-methyl-indan-4-ylmethyl)-3-methyl-pyrazol-1-yl]-propionic acid OR 3-[3-Ethoxy-4-(7-methoxy-6-methyl-indan-4-ylmethyl)-5-methyl-pyrazol-1-yl]-propionic acid | δ6.57 (1H, s), 4.02 (2H, t), 3.92 (2H, q), 3.65 (3H, s), 3.49 (2H, s), 2.87 (2H, t), 2.64-2.77 (4H, m), 2.09 (3H, s), 1.98-2.04 (2H, m), 1.91 (3H, s), 1.21 (3H, t). | 373 (M$^+$ + 1) | 2926, 1731, 1577, 1479 |
| 68 | [4-(7-Hydroxy-3,6-dimethyl-indan-4-ylmethyl)-3,5-dimethyl-pyrazol-1-yl]-acetic acid | δ8.10 (1H, s), 6.33 (1H, s), 4.76 (2H, s), 3.52 (2H, d), 3.27 (1H, merged with peak of water present in DMSO-$d_6$), 2.74-2.78 (2H, m), 2.05-2.10 (1H, m), 2.00 (3H, s), 1.99 (3H, s), 1.90 (3H, s), 1.67-1.72 (1H, m), 1.09 (3H, d). | 329 (M$^+$ + 1) | 3428, 2949 1715, 1483 |
| 69 | 2-[4-(7-Hydroxy-6-methyl-indan-4-ylmethyl)-3,5-dimethyl-pyrazol-1-ylmethyl]-pentanedioic acid | δ12.33 (2H, bs), 8.09 (1H, s), 6.54 (1H, s), 4.12-4.17 (1H, m), 3.92-3.97 (1H, m)3.43 (2H, s), 2.81-2.86 (1H, m), 2.74 (2H, t), 2.68 (2H, t), 2.15-2.17 (2H, m), 2.06 (3H, s), 2.01 (3H, s), 1.89-1.98 (5H, m), 1.63-1.69 (2H, m). | 399 (M$^+$ − 1) | 3367, 2957, 1734, 1483 |
| 70 | [4-(7-Methoxy-2,2,6-trimethyl-indan-4-ylmethyl)-3,5- | δ12.8 (1H, bs), 6.52 (1H, s), 4.77 (2H, s), 3.62 (3H, s), 3.47 (2H, s), | 355 (M$^+$ − 1) | 2952, 1716, 1574, 1478 |

TABLE 1-continued

| Compd No. | NAME | $^1$H-NMR (400 MHz, DMSO-d$_6$)$ | MASS | IR (KBr, CM$^{-1}$) |
|---|---|---|---|---|
| | dimethyl-pyrazol-1-yl]-acetic acid | 2.67 (2H, s), 2.57 (2H, s), 2.07 (3H, s), 2.03 (3H, s), 1.91 (3H, s), 1.10 (6H, s). | | |
| 71 | N-{2-[4-(7-Methoxy-6-methyl-indan-4-ylmethyl)-3,5-dimethyl-pyrazol-1-yl]-ethyl}-acetamide | δ7.97 (1H, t), 6.51 (1H, s), 3.96 (2H, t), 3.64 (3H, s), 3.46 (2H, s), 3.31 (2H, merged with peak of water present in DMSO-d$_6$), 2.86 (2H, t), 2.74 (2H, t), 2.09 (3H, s), 2.07 (3H, s), 1.96-2.01 (2H, m), 1.93 (3H, s), 1.77 (3H, s). | 356 (M$^+$ + 1) | 3316, 1644, 1544, 1478 |
| 72 | N-{2-[4-(7-Methoxy-6-methyl-indan-4-ylmethyl)-3,5-dimethyl-pyrazol-1-yl]-ethyl}-methanesulfonamide | δ7.19 (1H, t), 6.50 (1H, s), 4.00 (2H, t), 3.64 (3H, s), 3.49 (2H, s), 3.28 (2H, merged with peak of water present in DMSO-d$_6$), 2.86 (2H, t), 2.73-2.79 (5H, m), 2.11 (3H, s), 2.08 (3H, s), 1.94-2.03 (5H, m). | 392 (M$^+$ + 1) | 3111, 1573, 1475, 1384 |
| 73 | 4-[4-(7-Methoxy-6-methyl-indan-4-ylmethyl)-3,5-dimethyl-pyrazol-1-yl]-1-(toluene-4-sulfonyl)-piperidine | $^1$H-NMR (400 MHz, CDCl$_3$) δ7.68 (2H, d), 7.34 (2H, d), 6.47 (1H, s), 3.92-3.94 (2H, m), 3.81-3.89 (1H, m), 3.73 (3H, s), 3.52 (2H, s), 2.94 (2H, t), 2.77 (2H, t), 2.42-2.48 (5H, m), 2.28-2.38 (2H, m), 2.15 (3H, s), 2.05-2.11 (5H, m), 2.02 (3H, s), 1.90-1.93 (2H, m). | 508 (M$^+$ + 1) | 2949, 1485, 1443, 1330 |
| 74 | {3,5-Diethyl-4-[6-(4-fluoro-benzyl)-7-hydroxy-indan-4-ylmethyl-pyrazol-1-yl}-acetic acid | δ8.29 (1H, s), 7.08-7.13 (2H, m), 6.99 (2H, t), 6.45 (1H, s), 4.73 (2H, s), 3.75 (2H, s), 3.45 (2H, s), 2.76 (2H, t), 2.70 (2H, t), 2.37 (2H, q), 2.26 (2H, q), 1.92-1.99 (2H, m), 0.94 (3H, t), 0.82 (3H, t). | 437 (M$^+$ + 1) | 2974, 1734, 1604, 1506 |
| 75 | 3-{4-[7-Methoxy-6-(4-methoxy-phenyl)-indan-4-ylmethyl]-3,5-dimethyl-pyrazol-1-yl}-propionic acid | | 433 (M$^+$ − 1) | 2945, 1737, 1608, 1569 |
| 76 | 2-[3,5-Diethyl-4-(7-hydroxy-6-methyl-indan-4-ylmethyl)-pyrazol-1-yl]-N-isopropyl-acetamide | δ8.12 (1H, s), 7.73 (1H, d), 6.40 (1H, s), 4.58 (2H, s), 3.81-3.83 (1H, m), 3.48 (2H, s), 2.72-2.78 (4H, m), 2.44 (2H, q), 2.31 (2H, q), 1.93-2.02 (5H, m), 1.07 (3H, s), 1.05 (3H, s), 1.00 (3H, t), 0.90 (3H, t). | 384 (M$^+$ + 1) | 3249, 2972, 1756, 1658. |
| 77 | 3-[4-(7-Ethoxycarbonyloxy-6-methyl-indan-4-ylmethyl)-3,5-dimethyl-pyrazol-1-yl]-propionic acid methyl ester | δ6.58 (1H, s), 4.24 (2H, q), 4.16 (2H, t), 3.58 (3H, s), 3.55 (2H, s), 2.69-2.83 (6H, m), 2.12 (3H, s), 1.98-2.09 (5H, m), 1.94 (3H, s), 1.28 (3H, t). | 415 (M$^+$ + 1) | 1743, 1618, 1564, 1473 |
| 78 | Sodium salt of [3,5-Diethyl-4-(7-hydroxy-6-methyl-indan-4-ylmethyl)-pyrazol-1-yl]-acetic acid | δ6.62 (1H, s), 4.28 (2H, s), 3.38 (2H, merged with peak of water present in DMSO-d$_6$), 2.65-2.70 (4H, m), 2.38 (2H, q), 2.30 (2H, q), 1.85-1.99 (5H, m), 1.00 (3H, t), 0.90 (3H, t). | 343 (M$^+$ + 1) | 1613, 1562, 1469, 1400 |
| 79 | 3-[4-(7-Methoxy-6-methyl-indan-4-ylmethyl)-3-methyl-5-rifluoromethyl-pyrazol-1-yl]-propionic acid And 3-[4-(7-Methoxy-6-methyl-indan-4-ylmethyl)-5-methyl-3-rifluoromethyl-pyrazol-1-yl]-propionic acid | δ6.52 (1H, s, for major isomer), 6.38 (1H, s, for minor isomer), 5.04 (2H, s, for minor isomer), 5.03 (2H, s, for major isomer), 3.69 (2H, s, for both isomer), 3.58 (3H, s, for both isomer), 2.88 (2H, t, for both isomer), 2.75 (2H, t, for both isomer), 2.24 (3H, s, for both isomer), | 381 (M$^+$ − 1) | 2936, 1738, 1486, 1393 |

TABLE 1-continued

| Compd No. | NAME | $^1$H-NMR (400 MHz, DMSO-$d_6$)$ | MASS | IR (KBr, CM$^{-1}$) |
|---|---|---|---|---|
| 80 | [4-(4-Hydroxy-3-methyl-5,6,7,8-tetrahydro-naphthalen-1-ylmethyl)-3,5-dimethyl-pyrazol-1-yl]-acetic acid | 1.97-2.05 (5H, m, for both isomer). δ13.01 (1H, bs), 7.95 (1H, bs), 6.36 (1H, s), 4.80 (2H, s), 3.44 (2H, merged with peak of water present in DMSO-$d_6$), 2.54-2.58 (4H, m), 2.02 (3H, s), 1.98 (3H, s), 1.90 (3H, s), 1.65-1.70 (4H, m). | 329 (M$^+$ + 1) | 2924, 1719, 1575, 1471 |
| 81 | [4-(7-Chloro-indan-4-yloxy)-3-thiophen-2-yl-pyrazol-1-yl]-acetic acid And [4-(7-Chloro-indan-4-yloxy)-5-thiophen-2-yl-pyrazol-1-yl]-acetic acid | For major isomer δ7.82 (1H, s), 7.47 (1H, dd), 7.22 (1H, dd), 7.14 (1H, d), 7.05 (1H, dd), 6.63 (1H, d), 4.90 (2H, s), 3.04 (2H, t), 2.95 (2H, t), 2.10-2.17 (2H, m). | 373 (M$^+$ − 1) | 2960, 1746, 1560, 1463 |
| 82 | {4-[7-Methoxy-6-methyl-2-(4-nitro-phenoxy)-indan-4-ylmethyl]-3,5-dimethyl-pyrazol-1-yl}-acetic acid | δ12.81 (1H, bs), 8.22 (2H, d), 7.18 (2H, d), 6.62 (1H, s), 5.40-5.42 (1H, m), 4.74 (2H, s), 3.66 (3H, s), 3.45-3.52 (4H, m), 2.96-3.07 (2H, m), 2.11 (3H, s), 2.02 (3H, s), 1.91 (3H, s). | 464 (M$^+$ − 1) | 2944, 1732, 1595, 1503 |
| 83 | [5-Amino-4-(7-methoxy-6-methyl-indan-4-ylmethyl)-3-(4-methoxy-phenyl)-pyrazol-1-yl]-acetic acid And [3-Amino-4-(7-methoxy-6-methyl-indan-4-ylmethyl)-5-(4-methoxy-phenyl)-pyrazol-1-yl]-acetic acid | For major isomer δ7.34 (2H, d), 6.95 (2H, d), 6.53 (1H, s), 4.88 (2H, s), 3.87 (3H, s), 3.65-3.67 (5H, m), 2.90 (2H, t), 2.76 (2H, t), 1.99-2.05 (5H, m). | 422 (M$^+$ + 1) | 3336, 2942, 1729, 1613 |
| 84 | 2-[3,5-Diethyl-4-(7-hydroxy-6-methyl-indan-4-ylmethyl)-pyrazol-1-yl]-N-(1H-tetrazol-5-yl)-acetamide | δ15-98 (1H, bs), 12.42 (1H, s), 8.14 (1H, s), 6.41 (1H, s), 5.03 (2H, s), 3.50 (2H, s), 2.74-2.76 (4H, m), 2.50 (2H, merged with DMSO-d6 peak), 2.31 (2H, q), 1.97-2.02 (5H, m), 1.00 (3H, t), 0.93 (3H, t). $^1$H-NMR (400 MHz, CD$_3$OD) δ6.49 (1H, s), 5.04 (2H, s), 3.60 (2H, s), 2.76-2.84 (4H, m), 2.54 (2H, q), 2.43 (2H, q), 2.02-2.08 (5H, m), 1.06 (3H, t), 0.99 (3H, t). | 408 (M$^+$ − 1) | 3239, 2937, 1719, 1617 |
| 85 | 1-Carboxymethyl-5-(5-chloro-thiophen-2-yl)-4-(7-methoxy-6-methyl-indan-4-ylmethyl)-1H-pyrazole-3-carboxylic acid And 2-Carboxymethyl-5-(5-chloro-thiophen-2-yl)-4-(7-methoxy-6-methyl-indan-4-ylmethyl)-2H-pyrazole-3-carboxylic acid | For major isomer δ7.04 (1H, d), 6.77 (1H, d), 6.28 (1H, s), 5.24 (2H, s), 4.10 (2H, s), 3.65 (3H, s), 2.91 (2H, t), 2.83 (2H, t), 2.00-2.09 (5H, m). | 459 (M$^+$ − 1) | 3564, 2903, 1744, 1681 |

$Average values are provided for NMR

Following Compounds can Also be Prepared Using the Process Mentioned Above:

86. 3-[4-(1H-Indol-5-yloxy)-3,5-dimethyl-pyrazol-1-yl]-propionic acid;
87. [4-(1H-Indol-5-yloxy)-3,5-dimethyl-pyrazol-1-yl]-acetic acid;
88. 2-[4-(7-Hydroxy-indan-4-yloxy)-3,5-dimethyl-pyrazol-1-yl]-propionic acid;
89. 1-{2-[3,5-Diethyl-4-(7-hydroxy-6-methyl-indan-4-ylmethyl)-pyrazol-1-yl]-acetyl}-pyrrolidine-2-carboxylic acid;
90. [3,5-Diethyl-4-(7-hydroxy-6-pyrrolidin-1-ylmethyl-indan-4-ylmethyl)-pyrazol-1-yl]-acetic acid;

91. 3-[3,5-Diethyl-4-(7-hydroxy-6-pyrrolidin-1-ylmethyl-indan-4-ylmethyl)-pyrazol-1-yl]-propionic acid;
92. 3-[3,5-Diethyl-4-(7-methoxy-6-methoxymethyl-indan-4-ylmethyl)-pyrazol-1-yl]-propionic acid;
93. {3,5-Diethyl-4-[7-hydroxy-6-(pyrrolidine-1-carbonyl)-indan-4-ylmethyl]-pyrazol-1-yl}-acetic acid;
94. [3,5-Diethyl-4-(7-methoxy-6-methoxymethyl-indan-4-ylmethyl)-pyrazol-1-yl]-acetic acid;
95. 3-{3,5-Diethyl-4-[7-hydroxy-6-(pyrrolidine-1-carbonyl)-indan-4-ylmethyl]-pyrazol-1-yl}-propionic acid; and
96. N-(4-Chloro-phenyl)-2-[3,5-diethyl-4-(7-hydroxy-6-methyl-indan-4-ylmethyl)-pyrazol-1-yl]-acetamide.

Biological Activity

With the contemplation that metabolically active thyroid like compounds which will have minimal or no effect on appetite as well as will be lesser affinity towards Thyroid Receptors would be better effective for the treatment of various metabolic disorders such as obesity, dyslipidemia, atheresclerosis, insulin resistance and metabolic syndrome, Compounds of the present invention were tested for their effect on O2 consumption (metabolic effect), LDL cholesterol, glucose levels, insulin levels and food consumption (appetite stimulant) and also to assess transcriptional activity of thyroid hormone receptor by in vitro TRE (Thyroid receptor element) reporter assay for TRα1 and TRβ1.

Effect of Compounds on Transcriptional Activity of Thyroid Hormone Receptor (THR): THR α1 and THR β1

Assay procedure:

COS7 cells were transiently transfected with pGAL4 (beta galactosidase)/Thyroid α1 or pGAL4/Thyroid β1 and pLuc Pur. The cells were cotransfected with pLacZNorm for normalization of transfection efficiency. Transfected cells were then treated with different concentrations of compounds of present invention, vehicle for 24 hours.

Cells were the lysed and luciferase activity was monitored in all samples. Results were expressed as fold activation as compared to vehicle control.

Results: Thyroid(α1/β1) transactivation in COS7 cells.

TABLE 2

| Compound | Conc. (uM) | α1 Fold Activation | β1 Fold Activation |
| --- | --- | --- | --- |
| Vehicle (10 mM NaOH) | Zero | 1 | 1 |
| T3 | 20 | 35 | 29 |
|  | 0.02 | 17 | 13 |
| T2 | 20 | 20 | 27 |
|  | 2 | 14 | 16 |
|  | 0.2 | 7 | 4 |
|  | 0.02 | 1 | 2 |
| 1 | 20 | 1 | 1 |
| 2 | 20 | 1 | 1 |
| 3 | 20 | 1 | 1 |
| 7 | 20 | 3 | 1 |
| 8 | 20 | 3 | 1 |
| 9 | 20 | 2.5 | 2 |

The compounds of the present invention exhibited significantly less transcriptional activation of THR(α1) or THR(β1) as compared to T3 and T2 under experimental conditions.

In Vivo Assay

Experiment-1

Effect of Compounds on Oxygen Consumption, Food Consumption and Heart Weight

Methodology

C57BL6 mice (14-18 weeks age), fed for 8-12 weeks with High Fat Diet (45% kcal fat) were used for the study. The mice were placed in individual housing for one week. The mice were then kept in oxymax cages for 48 h for acclimatization. Basal recordings of oxygen consumption and carbon dioxide production for each mouse were recorded with indirect open circuit calorimeter (Oxymax, Columbus Instruments, USA (Ling fu et al., Endocrinology (2004); 145 (6); 2591-3). On the basis of body weight and basal oxygen consumption, mice were randomized and divided into two groups.

I) Vehicle treated group

II) Test compound treated group

The mice were treated with vehicle and test compounds intraperitoneally for 7-15 days. On the day 8, Oxygen consumption was measured for individual mouse 30 min after the drug treatment and % change with respect to vehicle is calculated.

During the experiment food consumption was monitored daily. At the end of the experiment the animals were scarified and the heart weights were recorded.

Results:

TABLE 3

Effect of test compounds on oxygen consumption, food consumption, body weight and heart weight

| Compound Nos. | Dose (µM/kg) | increase in O2 cons | increase in food consumption with reference to vehicle | increase in Heart weight with reference to vehicle |
| --- | --- | --- | --- | --- |
| T2 | 0.05 | * |  |  |
| T2 | 0.5 | ** | + | + |
| T2 | 2 | ** | ++ | ++ |
| T2 | 5 | ** | +++ | ++ |
| 1 | 11 | * | No change | No change |
| 2 | 11 | * | No change | No change |
| 3 | 11 | ** | No change | No change |
| 6 | 11 | * | No change | No change |
| 7 | 11 | ** | No change | No change |
| 8 | 11 | ** | No change | No change |
| 9 | 11 | ** | No change | No change |
| 19 | 11 | ** | No change | No change |
| 20 | 11 | ** | No change | No change |
| 14 | 11 | * | No change | No change |

For change in oxygen consumption:
* = Increase < 5%,
** = Increase > 5%
For change in food consumption:
+ = Increase by 5-10%,
++ = Increase by 10-20%,
+++ increase by >20%
For change in heart weight:
+ = Increase by 10-15%,
++ = Increase by 15-20%,
+++ increase by >20%

The test compounds of the present invention showed increase in the O2 consumption without significantly influencing the food consumption.

Experiment-2

Effect of Compounds on Body Weight, LDL Cholesterol, OGTT, Fasting Glucose and Fasting Insulin Levels Methodology:

Male C57BL6 mice were fed high fat diet (Research Diet, New Brunswick, N.J.). Mice were housed 3 animals per cage in a temperature-controlled facility (22±2° C.) with 12-h light/dark cycle. The mice were fed with High fat diet (45% kcal) for 8-12 weeks before drug treatment started.

DIO (Diet Induced Obese) mice were selected from the stock and randomized into three groups with 15 animals in each group on the basis of their body weight and age.

Group I Vehicle (10 ml/kg)
Group II Dose 1
Group III Dose 2

Before monitoring the basal parameters all the mice were acclimatized for the treatment by administering vehicle (0.02 M DiSodium hydrogen phosphate, 10 ml/kg i.p., b.i.d) for about 2 weeks. Then the animals were treated with either test compound A or B of formula (I) at two different doses for 6-12 weeks. The treatment was administered intraperitoneally b.i.d. The effect of 6-12 weeks treatment on change in body weight, body fat, LDL cholesterol, OGTT, fasting glucose and fasting insulin, was monitored.

A index of insulin resistance i.e. HOMA-IR was calculated using following formula $HOMA\_IR$ Score=Fasting serum insulin (µU/ml)× fasting serum glucose (mmol/l)/22.5

Results:

| Parameter | Test compound | Vehicle | Dose 1 | Dose 2 |
|---|---|---|---|---|
| Glucose (mg/dl) | A | 217.6 ± 5.4 | 185.9 ± 5.5** | 214.3 ± 6.5 |
|  | B | 240.51 ± 8.7 | 224.85 ± 6.2 | 210.43 ± 11.5* |
| Insulin (ng/ml) | A | 0.83 ± 0.14 | 0.38 ± 0.05** | 0.53 ± 0.05* |
|  | B | 0.90 ± 0.13 | 0.78 ± 0.08 | 0.74 ± 0.13 |
| HOMA_IR | A | 2.26 ± 0.36 | 0.90 ± 0.13** | 1.35 ± 0.14* |
|  | B | 2.7 ± 0.4 | 2.3 ± 0.26 | 2 ± 0.4 |
| LDL-C (mg/dl) | A | 24.96 ± 1.13 | 15.18 ± 1.6# | 13.73 ± 0.9# |
|  | B | 30.0 ± 1.03 | 27.9 ± 1.05 | 26.5 ± 0.9* |
| Body fat pads (g) | A | 2.67 ± 0.26 | 1.65 ± 0.17** | 2.02 ± 0.12* |
|  | B | 3.56 ± 0.44 | 2.33 ± 0.24* | 1.9 ± 0.18** |

N = 12 to 15/group;
*P < 0.05;
**P < 0.01;
P < 0.001

CONCLUSION

The 6-12 weeks treatment with Test compound A and B was found to be effective in significantly reducing the body weight, body fat, LDL cholesterol, fasting plasma glucose, insulin and improved the insulin resistance, with respect to vehicle. The FIG.1 also indicates that test compound was also showed improved glucose tolerance in experimental animals.

Overall, it can be concluded that the compounds of the present invention have utility in various metabolic disease conditions such as dyslipidemia, insulin resistance, type II diabetes, obesity and metabolic syndrome.

REFERENCES

WHO fact sheet, 2006
Melnikova I. & Wages D. Nature Reviews Drug Discovery (2006); 5: 369-370
Eberhard Ritz, Am. J. Cardiol (2007); 100[Suppl]:53-60
Young-Woo Park et al. Arch intern Med (2003); 163: 427-436
Richard Ceska, Diabetes and Vascular Disease Research (2007); 4(suppl): S2-S4 Kelly G S. Altern Med Rev (2000); 5 (4): 306-333
Burger' $6^{th}$ edition, vol 3, pp. 564-565
WO200703419
Liu Ye et al., JMC (2003); 46: 1580-88
Abrams J J et. al. J. Lipid Res. (1981); 22: 323-38
Aviram M. et. al. CUn. Biochem. (1982); 15: 62-66
Ness G C. et. al. Biochemical Pharmacology, (1998); 56: 121-129
Grover G J. et. al. Endocrinology, (2004); 145: 1656-1661
Grover G J. et. al. Proc. Natl. Acad. Sci. USA, (2003); 100: 10067-10072
Paul Webb. Expert Open. Investing. Drugs, (2004); 13 (5): 489-500
de Bruin et. al. J. CUn. Endo. Metal., (1993); 76: 121-126
A. Lombardi. Immun Endoc and Metal Agents in Med Chem (2006); 6: 255-65
Horst C., Biochem J. (1989); 261: 945-950
WO200509433
Amedeo columbano. Endocrinology (2006); 147 (7): 3211-8
Wing May Kong et al. Endocrinology (2004); 145: 5252-5258
Horst et al., J Endocrinology (1995); 145: 291-297
Ling fu et al., Endocrinology (2004); 145 (6): 2591-3

We claim:

1. A compound of formula (I)

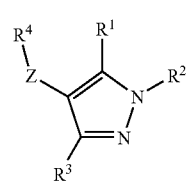

I

Wherein, $R^1$ and $R^3$ are the same or different, and are independently selected from H, $(C_1-C_6)$ alkyl, $(C_3-C_7)$ cycloalkyl, halo, CN, CF₃, —O—(C₁-C₆)alkyl, —CO₂-(C₁-C₆)alkyl, COOH, —CONH—(C₁-C₆)alkyl, —CONH-aryl, —NH2, —CONH—R⁶, —CONR⁵, —C₁-C₃alkyl-aryl, —(C₁-C₃) alkyl-R⁶, —NH—(C₁-C₆)alkyl, —NHaryl, —NH—SO₂-(C₁-C₆)alkyl, —CH₂—NH—(C₁-C₆)alkyl, —CH₂—O—(C₁-C₆)alkyl, —C₁-C₃alkyl-NR⁵, R⁶, R⁷, wherein said C₁-C₆alkyl and C₃-C₇ cycloalkyl are optionally substituted with one or more substituents selected from (C₁-C₆)alkyl, halo, cyano, —OH, oxo, —COOH, —O—(C₁-C₆)alkyl, —O-benzyl, —COO—(C₁-C₆)alkyl, —CONH—(C₁-C₆) alkyl, —CONR⁵, —CONH-aryl, —CONH-heteroaryl or —CH₂NR⁵;

R² is selected from (C₁-C₆)alkyl, (C₃-C₆)cycloalkyl, (C₃-C₆)alkenyl, (C₃-C₆)alkynyl, —C(O)—(C₁-C₃)alkyl—COOH, —(C₁-C₃)alkyl-COOH, —C(O)—(C₁-C₃)alkyl-COO-alkyl, —C(O)—C(O)O—(C₁-C₆)alkyl, —C(O)—(C₁-C₃)alkyl-NH—(C₁-C₆)alkyl, —C(O)—O—(C₁-C₆)alkyl, —C(O)NR⁵, —C(O)NH—(C₁-C₆) alkyl, —C(O)—(C₁-C₃)alkylaryl, —C(O)—(C₁-C₃)alkyl-R⁶, R⁶, R⁷, wherein said (C₁-C₆)alkyl, (C₃-C₆) cycloalkyl, (C₃-C₆)alkenyl and (C₃-C₆)alkynyl are optionally substituted with one or more substituents selected from perhaloalkyl, Oxo, —C(O)OH, —C(O)—O—(C₁-C₃)alkyl, —C(O)—O—(C₁-C₃)alky-laryl, —C(O)—O—(C₁-C₃)alkyl-R⁶, —CONH2, —CONH(C₁-C₃)alkyl, —C(O)NH-aryl, —C(O)NH—R⁶, —CONR⁵ —CONHNH₂, —C(=NH)NH—(C₁-C₆) alkyl, —C(=NH)NH₂, C(=NH)NHOH, —C(O)—R⁸, —C(O)NHSO₂(C₁-C₆) alkyl, —C(O)NHSO₂-aryl, —C(O)NHOH, —C(O)NHSO₂—R⁶, —C(O)NHNH—(C₁-C₆)alkyl, —C(O)NHNH-aryl, —CONH—(C₁-C₂)alkyl-aryl, —C(O)NH—(C₁-C₂) alkyl-R⁶, —CH₂NR⁵, —NH₂, —NH—(C₁-C₆)alkyl, —NH—C(O)—O—(C₁-C₃)alkyl, —NH—C(O)—(C₁-C₃)alkyl, —NHC(O)-aryl, —NHC(O)—(C₁-C₃)alkylaryl, —NHC(O)—R⁶, —NH—C(O)NR⁵, —NH—C(O)NH-aryl, —NHC(O)NH—(C₁-C₆)alkyl, —NHSO₂(C₁-C₆)alkyl, —NH—SO₂-aryl, —NH—SO₂—R⁶, halo, cyano, —OH, —O—(C₁-C₆)alkyl, —O-aryl, —O-heteroaryl, —O—(C₁-C₂)alkyl-aryl, —SO₃H, —SO₂NH-aryl, —SO₂NH—R⁶, —SO₂NH—(C₁-C₆)alkyl, R⁶ or R⁷;

R⁵ together with the nitrogen atom to which it is attached form a saturated or unsaturated (C₃-C₆) membered ring, which may further contain 1-2 heteroatoms selected from O, N and S and which is optionally substituted with one or more substituents selected from oxo, —COOH, halo, —OH, —O—(C₁-C₆)alkyl, and —(C₁-C₆)alkyl;

R⁶ is selected from phenyl or 5-8 membered heteroaryl containing 1-4 heteroatoms selected from O, N and S, wherein said heteroaryl or phenyl ring is optionally substituted with one or more substituents selected from halogen, —OH, —O—(C₁-C₆)alkyl, -perhaloalkyl, —(C₁-C₆)alkyl, —(C₃-C₆)cycloalkyl, —SO₂(C₁-C₆) alkyl, cyano, —COOH, —C(O)O—(C₁-C₆)alkyl, —C(O)O—CH₂-aryl, —C(O)O-aryl, —CONH(C₁-C₃) alkyl, nitro, —NH₂, —NH—(C₁-C₆)alkyl, —NHC(O)—(C₁-C₆)alkyl, —NHC(O)-aryl, —NHSO₂(C₁-C₆) alkyl, —CONH₂, —SO₂-(C₁-C₆)alkyl, —NHSO₂(C₁-C₆)alkyl and —COR⁸;

R⁷ is a 3-6 membered heterocyclic ring containing 1-4 heteroatom selected from O, N and S, wherein said heterocyclic ring is optionally substituted with one or more substituents selected from oxo, halogen, —O—(C₁-C₆)alkyl, —OH, —CF₃, (C₁-C₆)alkyl, (C₃-C₆)cycloalkyl, cyano, —COOH, —C(O)O—(C₁-C₆)alkyl, —C(O)O—CH₂-aryl, —C(O)O-aryl, —NH₂, —NH—(C₁-C₆)alkyl, —NHC(O)—(C₁-C₆)alkyl, —NHC(O)-aryl, —CONH₂, —SO₂aryl(C₁-C₆)alkyl, —SO₂—(C₁-C₆)alkyl, —NHSO₂(C₁-C₆)alkyl and —COR⁸;

R⁸ is an amino acid which is linked through its nitrogen atom;

Z=CH₂;

R⁴ is P;

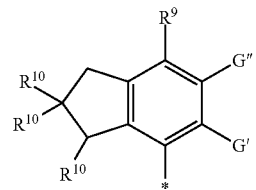

wherein * indicates the point of attachment to Z,

R⁹ is selected from —OH, —O-alkyl, —OSO₃H, halogen, —C(O)O—(C₁-C₆)alkyl, —C(O)NHR⁸, —OC(O)—(C₁-C₆)alkyl, —O-perhaloalkyl, —OC(O)O—(C₁-C₆) alkyl, —CONR⁵, —NHCO—(C₁-C₆)alkyl, —NHC(O)—)O—(C₁-C₆)alkyl, —NHC(O)—O—aryl, —NHSO₂—(C₁-C₆)alkyl, —NHSO₂-aryl, —NH-CONR⁵ and;

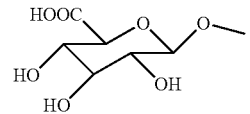

R¹⁰ is selected from H, Halogen, (C₁-C₆)alkyl, alkoxy, aryloxy, —NHCO—(C₁-C₆)alkyl, —NHSO₂—(C₁-C₆) alkyl and —NH—SO₂-aryl;

G' is selected from H, halogen and (C₁-C₆)alkyl;

G" is selected from hydrogen, (C₁-C₆)alkyl, (C₃-C₆)cycloalkyl, aryl, halogen, perhaloalkyl, CN, CHO, —(C₁-C₃)alkylaryl, —(C₁-C₆)alkyl-O—(C₁-C₆)alkyl, —CH₂R⁹, —CH₂aryl, —CH₂NR⁵, —COON, —C(O)O(C₁-C₆)alkyl, —CONH—(C₁-C₆)alkyl, —CONR⁵, —SO₂NR⁵, —SO₂NH—(C₁-C₆)alkyl and —SO₂NH-aryl; including their pharmaceutically acceptable salts.

2. A compound which is selected from the group consisting of:

3-[4-(7-Hydroxy-6-methyl-indan-4-ylmethyl)-3,5-dimethyl-pyrazol-1-yl]-propionic acid, 2-[4-(7-Hydroxy-6-methyl-indan-4-ylmethyl)-3,5-dimethyl-pyrazol-1-yl]-acetic acid, 7-[1-(2-Hydroxy-ethyl)-3,5-dimethyl-1H-pyrazol-4-ylmethyl]-5-methyl-indan-4-ol, 3-[4-(7-Methoxy-6-methyl-indan-4-ylmethyl)-3,5-dimethyl-pyrazol-1-yl]-propionic acid, 7-[3,5-Dimethyl-1-(1H-tetrazol-5-ylmethyl)-1H-pyrazol-4-ylmethyl]-5-methyl-indan-4-ol, 7-[3,5-Diisopropyl-1-(1H-tetrazol-5-ylmethyl)-1H-pyrazol-4-ylmethyl]-5-methyl-indan-4-ol, 3-[4-(7-Hydroxy-6-methyl-indan-4-ylmethyl)-3,5-diisopropyl-pyrazol-1-yl]-propionic acid,

[3,5-Diethyl-4-(7-hydroxy-6-methyl-indan-4-ylmethyl)-pyrazol-1-yl]-acetic acid,

3-[3,5-Diethyl-4-(7-hydroxy-6-methyl-indan-4-ylmethyl)-pyrazol-1-yl]-propionic acid, 7-[3,5-Diethyl-1-(1H-tetrazol-5-ylmethyl)-1H-pyrazol-4-ylmethyl]-5-methyl-indan-4-ol, 3-[4-(6-Chloro-7-hydroxy-indan-4-ylmethyl)-3,5-diethyl-pyrazol-1-yl]-propionic acid,

[4-(6-Chloro-7-hydroxy-indan-4-ylmethyl)-3,5-diethyl-pyrazol-1-yl]-acetic acid,
3-{4-[7-Hydroxy-6-(pyrrolidine-1-carbonyl)-indan-4-ylmethyl]-3,5-dimethyl-pyrazol-1-yl}-propionic acid,
3-[4-(6-Chloro-7-hydroxy-indan-4-ylmethyl)-3,5-diethyl-pyrazol-1-yl]-propionic acid,
1-{2-[4-(7-Hydroxy-6-methyl-indan-4-ylmethyl)-3,5-dimethyl-pyrazol-1-yl]-acetyl}-pyrrolidine-2-carboxylic acid,
[4-(7-Hydroxy-6-methyl-indan-4-ylmethyl)-3,5-diisopropyl-pyrazol-1-aacetic acid,
3-[4-(7-Hydroxy-6-methyl-indan-4-ylmethyl)-3,5-dimethyl-pyrazol-1-yl]-N-isopropyl-propionamide,
4-[4-(7-Hydroxy-6-methyl-indan-4-ylmethyl)-3,5-dimethyl-pyrazol-1yl]-butyric acid,
3-[4-(7-Hydroxy-6-methyl-indan-4-ylmethyl)-3,5-dimethyl-pyrazol-1-yl]-N-(1H-tetrazol-5-yl)-propionamide,
5-[4-(7-Hydroxy-6-methyl-indan-4-ylmethyl)-3,5-dimethyl-pyrazol-1-ylmethyl]-3H-[1,3,4]oxadiazol-2-one,
7-{3,5-Dimethyl-1-[2-(1H-tetrazol-5-yl)-ethyl]-1H-pyrazol-4-ylmethyl}-5-methyl-indan-4-ol,
{2-[4-(7-Hydroxy-6-methyl-indan-4-ylmethyl)-3,5-dimetyl-pyrazol-1-yl]-acetylamino}-acetic acid,
5-[4-(Hydroxy-6-methyl-indan-4-ylmethyl)-3,5-dimethyl-pyrazol-1ylmethyl]-1H-pyrazol-3-ol,
5-[3,5-Diethyl-4-(7-hydroxy-6-methyl-indan-4-ylmethyl)-pyrazol-1-ylmethyl]-3H-[1,3,4]oxadiazol-2-one,
5-{2-[4-(7-Hydroxy-6-methyl-indan-4-ylmethyl)-3,5-dimethyl-pyrazol-1-yl]-ethyl}-3H-[1,3,4]oxadiazol-2-one,
{2-[3,5-Diethyl-4-(7-hydroxy-6-methyl-indan-4-ylmethyl)-pyrazol-1-yl-acetylamino}-acetic acid,
6-[4-(7-Hydroxy-6-methyl-indan-4-ylmethyl)-3,5-dimethyl-pyrazol-1-ylmethyl]-2-methyl-3H-pyrimidin-4-one,
3-[4-(7-Hydroxy-6-methyl-indan-4-ylmethyl)-3,5-dimethyl-pyrazol-1-ylmethyl]-[1,2,4]oxadiazol-5-ol,
7-(1-Benzyl-3,5-dimethyl-1H-pyrazol-4-ylmethyl)-5-methyl-indan-4-ol,
3-{4-[7-Hydroxy-6-(4-methyl-benzyl)-indan-4-ylmethyl]-3,5-dimethylpyrazol-1-yl}-propionic acid,
2-[4-(7-Hydroxy-6-methyl-indan-4-ylmethyl)-3,5-dimethyl-pyrazol-1-yl]-propionic acid,
3-[4-(7-Hydroxy-6-isopropyl-indan-4-ylmethyl)-3,5-dimethyl-pyrazol-1yl]-propionic acid,
{4-[7-Hydroxy-6-(4-methyl-benzyl)-indan-4-yl methyl]-3,5-dimethylpyrazol-1-yl}-acetic acid,
3-{4-[6-(4-Fluoro-benzyl)-7-hydroxy-indan-4-ylmethyl]-3,5-dimethylpyrazol-1-yl}-propionic acid,
{4-[6-(4-Fluoro-benzyl)-7-hydroxy-indan-4-yl methyl]-3,5-dimethylpyrazol-1-yl}-acetic acid,
Sodium salt of 4-[4-(7-Hydroxy-6-methyl-indan-4-ylmethyl)-3,5dimethyl-pyrazol-1-yl]-butyric acid,
Magnesium salt of 3-[4-(7-Hydroxy-6-methyl-indan-4-ylmethyl)-3,5-dimethyl-pyrazol-1-yl]-propionic acid,
Sodium salt of 3-[4-(7-Hydroxy-6-methyl-indan-4-ylmethyl)-3,5-dimethyl-pyrazol-1]-propionic acid,
3-{3,5-Diethyl-4-[6-(4-fluoro-benzyl)-7-hydroxy-indan-4-ylmethyl]-pyrazol-1-yl}-propionic acid,
3-[4-(7-Methoxy-6-methyl-indan-4-ylmethyl)-3,5-dimethyl-pyrazol-1-yl]-3-oxo-propionic acid ethyl ester,
[3,5-Diethyl-4-(7-hydroxy-6-methyl-indan-4-ylmethyl)-pyrazol-1-yl]-acetic acid hydrazide,
N-Hydroxy-2[4-(7-methoxy-6-methyl-indan-4-ylmethyl)-3,5-dimethylpyrazol-1-yl]-acetamidine,
[4-(7-Methoxy-6-methyl-indan-4-ylmethyl)-3,5-dimethyl-pyrazol-1-yl]-oxo-acetic acid ethyl ester,
[4-(7-Methoxy-6-methyl-indan-4-ylmethyl)-3,5-dimethyl-pyrazol-1-yl]-morpholin-4-yl-methanone,
1-(4-Chloro-phenyl)-4-(7-methoxy-6-methyl-indan-4-ylmethyl)-3,5-dimethyl-1H-pyrazole,
2-(4-Methanesulfonyl-phenyl)-1-[4-(7-methoxy-6-methyl-indan-4ylmethyl)-3,5-dimethyl-pyrazol-1-yl]-ethanone,
4-(7-Methoxy-6-methyl-indan-4-ylmethyl)-3,5-dimethyl-pyrazole-1-carboxylic acid ethyl ester,
Propane-2-sulfonic acid {3-[4-(7-methoxy-6-methyl-indan-4-ylmethyl)3,5-dimethyl-pyrazol-1-yl]-propionyl}-amide,
3-[5-Ethoxy-4-(7-methoxy-6-methyl-indan-4-ylmethyl)-3-methyl-pyrazol-1-yl]-propionic acid,
3-[3-Ethoxy-4-(7-methoxy-6-methyl-indan-4-ylmethyl)-5-methyl-pyrazol-yl]-propionic acid,
[4-(7-Hydroxy-3,6-dimethyl-indan-4-ylmethyl)-3,5-dimethyl-pyrazol-1-yl]-acetic acid,
2-[4-(7-Hydroxy-6-methyl-indan-4-ylmethyl)-3,5-dimethyl-pyrazol-1-ylmethyl]-pentanedioic acid,
[4-(7-Methoxy-2,2,6-trimethyl-indan-4-ylmethyl)-3,5-dimethyl-pyrazol-1-yl]-acetic acid,
N-{2-[4-(7-Methoxy-6-methyl-indan-4-ylmethyl)-3,5-dimethyl-pyrazol-1-yl]-ethyl}-acetamide,
N-{2-[4-(7-Methoxy-6-methyl-indan-4-ylmethyl)-3,5-dimethyl-pyrazol-1-yl]-ethyl}-methanesulfonamide,
4-[4-(7-Methoxy-6-methyl-indan-4-ylmethyl)-3,5-dimethyl-pyrazol-1-yl]-1-(toluene-4-sulfonyl)-piperidine,
{3,5-Diethyl-4-[6-(4-fluoro-benzyl)-7-hydroxy-indan-4-ylmethyl]-pyrazol -1-yl}-acetic acid,
3-{4-[7-Methoxy-6-(4-methoxy-phenyl)-indan-4-ylmethyl]-3,5-dimethylpyrazol-1-yl}-propionic acid,
2-[3,5-Diethyl-4-(7-hydroxy-6-methyl-indan-4-ylmethyl)-pyrazol-1-yl]-N-isopropyl-acetamide,
3-[4-(7-Ethoxycarbonyloxy-6-methyl-indan-4-ylmethyl)-3,5-dimethylpyrazol-1-yl]-propionic acid methyl ester,
Sodium salt of [3,5-Diethyl-4-(7-hydroxy-6-methyl-indan-4-ylmethyl)pyrazol-1-yl]-acetic acid,
3-[4-(7-Methoxy-6-methyl-indan-4-ylmethyl)-3-methyl-5-trifluoromethyl-pyrazol-1-yl-propionic acid, 3-[4-(7-Methoxy-6-methyl-indan-4-ylmethyl)-5-methyl-3-trifluoromethyl-pyrazol-1-yl]-propionic acid,
{4-[7-Methoxy-6-methyl-2-(4-nitro- phenoxy)-indan-4-ylmethyl]-3,5-dimethyl-pyrazol-1-yl}-acetic acid,
[5-Amino-4-(7-methoxy-6-methyl-indan-4-ylmethyl)-3-(4-methoxyphenyl)-pyrazol-1-yl]-acetic acid
[3-Amino-4-(7-methoxy-6-methyl-indan-4-ylmethyl)-5-(4-methoxyphenyl)-pyrazol-1-yl]-acetic acid,
2-[3,5-Diethyl-4-(7-hydroxy-6- methyl-indan-4-ylmethyl)- pyrazol-1-yl]-N-(1H-tetrazol-5-yl)-acetamide,
1-Carboxymethyl-5-(5-chloro-thiophen-2-yl)-4-(7-methoxy-6-methyl-indan-4-ylmethyl)-1H-pyrazole-3-carboxylic acid, 2-Carboxymethyl-5-(5-chloro-thiophen-2-yl)-4-(7-methoxy-6-methyl-indan-4-ylmethyl)-2H-pyrazole-3-carboxylic acid,
1-{2-[3,5-Diethyl-4-(7-hydroxy-6-methyl-indan-4-ylmethyl)-pyrazol-1-yl]-acetyl}-pyrrolidine-2-carboxylic acid,
[3,5-Diethyl-4-(7-hydroxy-6-pyrrolidin-1-ylmethyl-indan-4-ylmethyl)pyrazol-1-yl]-acetic acid,
3-[3,5-Diethyl-4-(7-hydroxy-6-pyrrolidin-1-ylmethyl-indan-4-ylmethyl)-pyrazol-1-yl]-propionic acid,
3-[3,5-Diethyl-4-(7-methoxy-6-methoxymethyl-indan-4-ylmethyl)pyrazol-1-yl]-propionic acid, {3,5-Diethyl-4-[7-hydroxy-6-(pyrrolidine-1-carbonyl)-indan-4-ylmethyl]-pyrazol-1-yl}-acetic acid,

[3,5-Diethyl-4-(7-methoxy-6-methoxymethyl-indan-4-ylmethyl)-pyrazol-1-yl]-acetic acid, 3-{3,5-Diethyl-4-[7-hydroxy-6-(pyrrolidine-1-carbonyl)-indan-4-ylmethyl]-pyrazol-1-yl}-propionic acid, and N-(4-Chloro-phenyl)-2-[3,5-diethyl-4-(7-hydroxy-6-methyl-indan-4-ylmethyl)-pyrazol-1-yl]-acetamide;

including their pharmaceutically acceptable salts.

3. A pharmaceutical composition comprising a therapeutically effective amount of one or more compounds as claimed in claim 1, optionally in association with a pharmaceutically acceptable diluents or carriers.

4. A method of treating obesity in a mammalian organism, comprising administering to the said mammalian organism in need thereof, a therapeutically effective amount of a compound as claimed in claim 1.

5. A method of ameliorating insulin resistance in a mammalian organism, comprising administering to the said mammalian organism in need thereof, a therapeutically effective amount of a compound as claimed in claim 1.

6. A method of treating dyslipidemia in a mammalian organism, comprising administering to the said mammalian organism in need thereof, a therapeutically effective amount of a compound as claimed in claim 1.

7. A method of treating metabolic syndrome in a mammalian organism, comprising administering to the said mammalian organism in need thereof, a therapeutically effective amount of a compound as claimed in claim 1.

8. A process for the preparation of a compound as claimed in claim 1, which comprises:

(i) reacting a compound of formula (II)

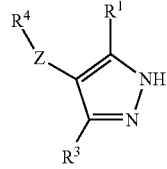

II with a compound of formula $R^2$—Y

Wherein Y is a leaving group preferably halogen in the presence of suitable base in suitable solvent or;

(ii) reacting a compound of formula (III) or (IX)

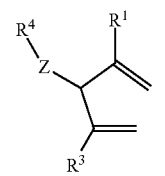

III

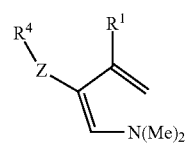

IX with hydrazine hydrate or suitably substituted hydrazine of formula $R^2$ NH NH$_2$ wherein $R^1$, $R^2$, $R^3$ and $R^4$ are as defined in claim 1.

9. A pharmaceutical composition comprising a therapeutically effective amount of one or more compounds as claimed in claim 2, optionally in association with pharmaceutically acceptable diluents or carriers.

10. A method of treating obesity in a mammalian organism, comprising administering to the said mammalian organism in need thereof, a therapeutically effective amount of a compound as claimed in claim 2.

11. A method of ameliorating insulin resistance in a mammalian organism, comprising administering to the said mammalian organism in need thereof, a therapeutically effective amount of a compound as claimed in claim 2.

12. A method of treating dyslipidemia in a mammalian organism, comprising administering to the said mammalian organism in need thereof, a therapeutically effective amount of a compound as claimed in claim 2.

13. A method of treating metabolic syndrome in a mammalian organism, comprising administering to the said mammalian organism in need thereof, a therapeutically effective amount of a compound as claimed in claim 2.

14. The compound as claimed in claim 2 wherein the compound is 3-[4-(7-Hydroxy-6-methyl-indan-4-ylmethyl)-3,5-dimethyl-pyrazol-1-yl]-propionic acid, including its pharmaceutically acceptable salts.

* * * * *